US008691222B2

(12) United States Patent
Hazen et al.

(10) Patent No.: US 8,691,222 B2
(45) Date of Patent: Apr. 8, 2014

(54) NLRR-1 ANTAGONISTS AND USES THEREOF

(75) Inventors: Meredith Hazen, Belmont, CA (US); Jo-Anne S. Hongo, Redwood City, CA (US); Victoria Smith, Burlingame, CA (US); Susanna Stinson, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 503 days.

(21) Appl. No.: 12/680,243

(22) PCT Filed: Oct. 1, 2008

(86) PCT No.: PCT/US2008/078474
§ 371 (c)(1),
(2), (4) Date: Sep. 13, 2010

(87) PCT Pub. No.: WO2009/046123
PCT Pub. Date: Apr. 9, 2009

(65) Prior Publication Data
US 2010/0330082 A1    Dec. 30, 2010

Related U.S. Application Data

(60) Provisional application No. 60/976,892, filed on Oct. 2, 2007.

(51) Int. Cl.
*A61K 39/395*    (2006.01)
(52) U.S. Cl.
USPC ..................... 424/130.1; 424/141.1
(58) Field of Classification Search
None
See application file for complete search history.

(56) References Cited

U.S. PATENT DOCUMENTS

| | | | |
|---|---|---|---|
| 2003/0186866 A1* | 10/2003 | Baker et al. | 514/12 |
| 2005/0153396 A1 | 7/2005 | Baker et al. | |
| 2006/0099214 A1* | 5/2006 | Ebner et al. | 424/155.1 |
| 2006/0210561 A1* | 9/2006 | Baughman et al. | 424/143.1 |
| 2007/0286864 A1* | 12/2007 | Buck et al. | 424/155.1 |
| 2008/0311107 A1* | 12/2008 | Bollinger et al. | 424/130.1 |

FOREIGN PATENT DOCUMENTS

WO    WO 2006130135 A1 * 12/2006
WO    2007/050798 A2    5/2007

OTHER PUBLICATIONS

PCT IPER for PCT/US2008/078474 Date of Issuance Apr. 7, 2010.
PCT ISR for PCT/US2008/078474 Date of Mailing May 13, 2009.
PCT Written Opinion of the ISA for PCT/US2008/078474 Date of Mailing May 13, 2009.
Andren et al., "How well does the Gleason score predict prostate cancer death? A 20-year followup of a population based cohort in Sweden" J Urol. 175(4):1337-40 ( 2006).
Andren et al., "MUC-1 gene is associated with prostate cancer death: a 20-year follow-up of a population-based study in Sweden" Br J Cancer 97(6):730-4 ( 2007).
Aubert et al., "Screening for mammalian neural genes via fluorescence-activated cell sorter purification of neural precursors from Sox1-gfp knock-in mice" Proc Natl Acad Sci U S A. 100(1):11836-41 ( 2003).
Bormann et al., "zfNLRR, a novel leucine-rich repeat protein is preferentially expressed during regeneration in zebrafish" Mol Cell Neurosci. 13(3):167-79 ( 1999).
Chinnaiyan et al., "Mechanisms of enhanced radiation response following epidermal growth factor receptor signaling inhibition by erlotinib (Tarceva)" Cancer Res. 65(8):3328-35 ( 2005).
Dziadziuszko et al., "Epidermal growth factor receptor messenger RNA expression, gene dosage, and gefitinib sensitivity in non-small cell lung cancer" Clin Cancer Res. 12(10):3078-84 ( 2006).
Eberhard et al., "Mutations in the epidermal growth factor receptor and in KRAS are predictive and prognostic indicators in patients with non-small-cell lung cancer treated with chemotherapy alone and in combination with erlotinib" J Clin Oncol. 23(25):5900-9 ( 2005).
Ebner and Derynck, "Epidermal growth factor and transforming growth factor-alpha: differential intracellular routing and processing of ligand-receptor complexes" Cell Regul. 2(8):599-612 ( 1991).
El-Obeid et al., "TGF-alpha-driven tumor growth is inhibited by an EGF receptor tyosine kinase inhibitor" Biochem Biophys Res Commun. 290(1):349-58 ( 2002).
Fukamachi et al., "Neuronal leucine-rich repeat protein-3 amplifies MAPK activation by epidermal growth factor through a carboxyl-terminal region containing endocytosis motifs" J Biol Chem. 277(46):43549-52 ( 2002).
Fukamachi et al., "Rat neuronal leucine-rich repeat protein-3: cloning and regulation of the gene expression" Biochem Biophys Res Commun. 287(1):257-63 ( 2001).
Gleason et al., "Prediction of prognosis for prostatic adenocarcinoma by combined histological grading and clinical staging" J Urol. 111(1):58-64 ( 1974).
Haines et al., "The NLRR gene family and mouse development: Modified differential display PCR identifies NLRR-1 as a gene expressed in early somitic myoblasts" Dev Biol. 281(2):145-59 ( 2005).
Hamano et al., "Identification of novel human neuronal leucine-rich repeat (hNLRR) family genes and inverse association of expression of Nbla 10449/hNLRR-1 and Nbla10677/hNLRR-3 with the prognosis of primary neuroblastomas" Int J Oncol. 24(6):1457-66 ( 2004).
Han et al., "Predictive and prognostic impact of epidermal growth factor receptor mutation in non-small-cell lung cancer patients treated with gefitinib" J Clin Oncol. 23(11):2493-501 ( 2005).
Haugh et al., "Effect of epidermal growth factor receptor internalization on regulation of the phospholipase C-gamma1 signaling pathway" J Biol Chem. 274(13):8958-65 ( 1999).
Haugh et al., "Internalized epidermal growth factor receptors participate in the activation of p21(ras) in fibroblasts" J Biol Chem. 274(48):34350-60 ( 1999).
Hayata et al., "Molecular cloning of XNLRR-1, a Xenopus homolog of mouse neuronal leucine-rich repeat protein expressed in the devoloping Xenopus nervous system" GENE 221(1):159-66 (Oct. 9, 1998).

(Continued)

*Primary Examiner* — Hong Sang
(74) *Attorney, Agent, or Firm* — Traci H. Ropp

(57) ABSTRACT

NLRR-1 antagonists and methods of their use in treating cancer and other disorders are provided.

16 Claims, 34 Drawing Sheets

(56) References Cited

OTHER PUBLICATIONS

Hennessy et al., "Exploiting the PI3K/AKT pathway for cancer drug discovery" Nat Rev Drug Discov. 4(12):988-1004 ( 2005).
Inoue et al., "Inhibition of the leucine-rich repeat protein LINGO-1 enhances survival, structure, and function of dopaminergic neurons in Parkinson's disease models" Proc Natl Acad Sci U S A. 104(36):14430-5 ( 2007).
Jhappan et al., "TGF alpha overexpression in transgenic mice induces liver neoplasia and abnormal development of the mammary gland and pancreas" Cell 15(61 SUPPL 6):1137-46 ( 1990).
Jiang et al., "Autocrine transforming growth factor alpha provides a growth advantage to malignant cells by facilitating re-entry into the cell cycle from suboptimal growth states" J Biol Chem. 273(47):31471-9 ( 1998).
Lapointe et al., "Gene expression profiling indentifies clinically relevant subtypes of prostate cancer" Proc Natl Acad Sci U S A. 101(3):811-6 ( 2004).
Levkowitz et al., "c-Cbl/Sli-1 regulates endocytic sorting and ubiquitination of the epidermal growth factor receptor" Genes Dev. 12(23):3663-74 ( 1998).
Lynch et al., "Activating Mutations in the Epidermal Growth Factor Receptor Underlying Responsiveness of Non-Small-Cell Lung Cancer to Gefitinib" New Engl J Med 350(21):2129-2139 (May 20, 2004).
Maeda et al., "pH-dependent receptor/ligand dissociation as a determining factor for intracellular sorting of ligands for epidermal growth factor receptors in rat hepatocytes" J Control Release. 82(1):71-82 ( 2002).
Martinez-Arca et al., "Recycling of cell surface pro-transforming growth factor- {alpha} regulates epidermal growth factor receptor activation" J Biol Chem. 280(44):36970-7 ( 2005).
Mi et al., "LINGO-1 antagonist promotes spinal cord remyelination and axonal integrity in MOG-induced experimental autoimmune encephalomyelitis" Nat Med. 13(10):1228-33 ( 2007).
Moyer et al., "Induction of apoptosis and cell cycle arrest by CP-358,774, and inhibitor of epidermal growth factor receptor tyrosine kinase" Cancer Res 57(21):4838-48 (Nov. 1997).
Ng et al., "Effects of the epidermal growth factor receptor inhibitor OSI-774, Tarceva, on downstream signaling pathways and apoptosis in human pancreatic adenocarcinoma" Mol Cancer Ther. 1(10):777-83 ( 2002).
O'Dwyer et al., "Epidermal growth factor receptor-targeted therapy in colorectal cancer" Semin Oncol. 29(5 SUPPL 14):10-17 ( 2002).
Oliveira et al., "Molecular biology of epidermal growth factor receptor inhibition for cancer therapy" Expert Opin Biol Ther. 6(6):605-17 ( 2006).
Paez et al., "EGFR Mutations in Lung Cancer: Correlation with Clinical Responses to Gefitinib Therapy" Science 304:1497 (Jun. 2004).
Qian et al., "E-cadherin-medicated adhesion inhibits ligand-dependent activation of diverse receptor tyrosine kinases" EMBO J. 23(8):1739-48 ( 2004).
Sato et al., "Overexpression of N-acetylglucosaminyltansferase III enhances the epidermal growth factor-induced phosphorylation of ERK in HeLaS3 cells by up-regulation of the internalization rate of the receptors" J Biol Chem. 276(15):11956-62 ( 2001).
Scher et al., "Changing Pattern of Expression of the Epidermal Growth Factor Receptor and Transforming Growth Factor $\alpha$ in the Progression of Prostatic Neoplasms" Clin Cancer Res 1:545-550 (May 1995).
Schoeberl et al., "Computational modeling of the dynamics of the MAP kinase cascade activated by surface and internalized EGF receptors" Nat Biotechnol. 20(4):370-5 ( 2002).
Sebastian et al., "The complexity of targeting EGFR signalling in cancer: from expression to turnover" Biochim Biophy s Acta. 1766(1):120-39 ( 2006).
Shepherd et al., "Erlotinib in previously treated non-small-cell lung cancer" N Engl J Med. 353(2):123-32 ( 2005).
Sordella et al., "Gefitinib-Sensitizing EGFR Mutations in Lung Cancer Activate Anti-Apoptotic Pathways" Science 305:1163-1167 (Aug. 20, 2004)
Tackels-Horne et al., "Identification of differentially expressed genes in hepatocellular carcinoma and metastatic liver tumors by oligonucleotide expression profiling" Cancer 92(2):395-405 ( 2001).
Taguchi et al., "Molecular Cloning of Novel Leucine-rich Repeat Proteins and Their Expression in the Developing Mouse Nervous System" Mol Brain Res 35:31-40 ( 1996).
Taniguchi et al., "Cloning and expression of a novel gene for a protein with leucine-rich repeats in the developing mouse nervous system" Brain Res Mol Brain Res. 36(1):45-52 ( 1996).
Tsao et al., "Erlotinib in lung cancer—molecular and clinical predictors of outcome" New Engl J Med 353(2):133-144 (Jul. 14, 2005).
Vivanco et al., "The Phosphatidylinositol 3-Kinase-AKT Pathway in Human Cancer" Nature Rev Cancer 2:489-501 (Jul. 2002).
Wang et al., "Autocrine TGFalpha expression in the regulation of initiation of human colon carcinoma growth" J Cell Physiol. 177(3):387-95 ( 1998).
Wang et al., "Endosomal signaling of epidermal growth factor receptor stimulates signal transduction pathways leading to cell survival" Mol Cell Biol. 22(20):7279-90 ( 2002).
Wells et al., "EGF receptor" Int J Biochem Cell Biol 31(6):637-43, 1999.
Yauch et al., "Epithelial versus mesenchymal phenotype determines in vitro sensitivity and predicts clinical activity of erlotinib in lung cancer patients" Clin Cancer Res 11:8686-8698 ( 2005).
Zhou et al., "Synergy of epidermal growth factor receptor kinase inhibitor AG1478 and ErbB2 kinase inhibitor AG879 in human colon carcinoma cells is associated with induction of apoptosis" Cancer Res. 65(13):5848-56 ( 2005).

* cited by examiner

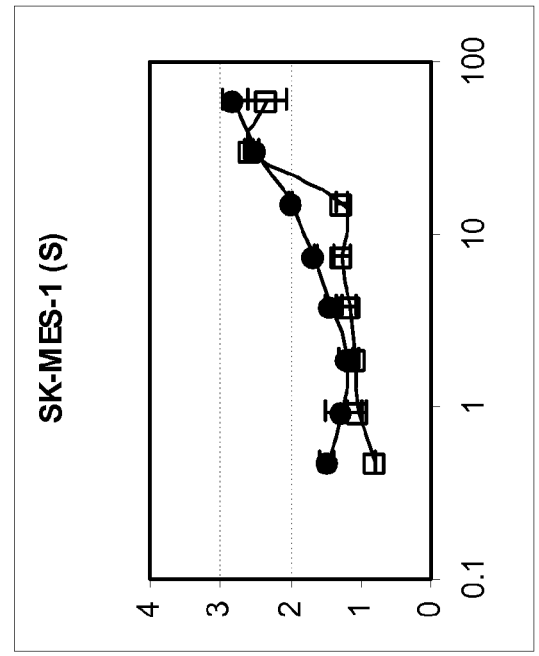
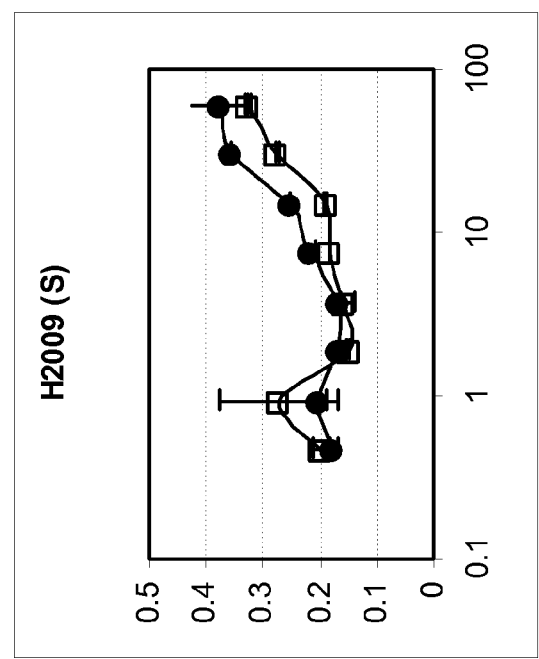
Figure 8E
Figure 8F

MARMSFVIAACQLVLGLLMTSLTESSIQNSECPQLCVCEIRPWFTPQSTYREATTVDCNDLRL
TRIPSNLSSDTQVLLQSNNIAKTVDELQQLFNLTELDFSQNNFTNIKEVGLANLTQLTTLHL
EENQITEMTDYCLQDLSNLQELYINHNQISTISAHAFAGLKNLLRLHLNSNKLKVIDSRWFDS
TPNLEILMIGENPVIGILDMNFKPLANLRSLVLAGMYLTDIPGNALVGLDSLESLSFYDNKLVK
VPQLAQKVPNLKFLDLNKNPIHKIQEGDFKNMLRLKELGINNMGELVSVDRYALDNLPELT
KLEATNNPKLSYIHRLAFRSVPALESLMLNNNALNAIYQKTVESLPNLREISHSNPLRCDCV
IHWINSNKTNIRFMEPLSMFCAMPPEYKGHQVKEVLQDSSEQCLPMISHDSFPNRLNVDIGT
TVFLDCRAMAEPEPEIYWVTPIGNKITVETLSDKYKLSSEGTLEISNIQIEDSGRYTCVAQNV
QGADTRVATIKVNGTLLDGTQVLKIYVKQTESHSILVSWKVNSNVMTSNLKSSATMKIDNPH
ITYTARVPVDVHEYNLTHLQPSTDYEVCLTVSNIHQTQKSCVNVTTKNAAFAVDISDQETST
ALAAVMGSMFAVISLASIAVYFAKRFKRKNYHHSLKKYMQKTSSIPLNELYPPLINLWEGDSE
KDKDGSADTKPTQVDTSRSYYMW [SEQ ID NO: 1]

Figure 15

NLRR-1 ANTAGONISTS AND USES THEREOF

CROSS REFERENCE TO RELATED APPLICATIONS

This application is a national stage application filed under 35 USC §371 of International Application No. PCT/US2008/078474, filed on Oct. 1, 2008, which claims priority under 35 USC §119(e) to U.S. provisional application No. 60/976,892, filed Oct. 2, 2007, the entire disclosures of which are incorporated by reference herein.

FIELD OF THE INVENTION

The present invention relates to compositions and methods useful for the treatment of cancer and other disorders, and in particular to Neuronal Leucine Rich Repeat Protein-1 antagonists useful for treating cancers.

BACKGROUND OF THE INVENTION

Neuronal Leucine Rich Repeat (NLRR) proteins were first identified from a mouse brain cDNA library and are encoded by a three-gene family in mammals (Taguchi et al., 1996; Taniguchi et al., 1996). They constitute a novel LRR protein family containing 11 or 12 LRRs, an immunoglobulin domain, and a type III fibronectin domain (Bormann et al., 1999; Fukamachi et al., 2001; Hayata et al., 1998). From their structural features, these glycosylated transmembrane proteins are postulated to play roles in cell adhesion, migration, morphogenesis or signaling. The regulated embryonic expression and cellular location of NLRR family proteins suggest important roles during development in the control of cell adhesion, movement or signaling (Haines et al., 2005), but their functions have remained elusive. NLRR-3 has been shown to have a role in potentiating EGFR signaling in response to low concentrations of EGF, probably by promoting association of EGFR and EGF in clathrin-coated pits and endosomes as there is no evidence for physical association with EGFR (Fukamachi et al., 2002). Endocytosis of EGFR has long been recognized as an attenuation mechanism, but several studies have revealed that endosomal complexes retain signaling potency and that EGFR internalization can even serve to amplify MAP kinase phosphorylation, and stimulate pathways leading to cell survival (Haugh et al., 1999a; Haugh et al., 1999b; Sato et al., 2001; Schoeberl et al., 2002; Wang et al., 2002)

NLRR-1 (as known as LRRN1) shares homology with NLRR-3, including complete conservation of the C-terminal endocytosis motif. NLRR-1 was identified as an early neuroectodermal developmental marker (Aubert et al., 2003) and has also been found in a subset of myogenic precursors during somite development (Haines et al., 2005), but its function remains unknown.

Data regarding expression of NLRR proteins in human disease states is limited, but in neuroblastoma, expression of NLRR-1, unlike NLRR-3, is significantly associated with short survival and poor prognostic factors (Hamano et al., 2004).

The epidermal growth factor receptor (EGFR) family comprises four closely related receptors (HER1/EGFR, HER2, HER3 and HER4). The EGFR family and associated ligands trigger a series of intracellular signaling events regulating cell proliferation, migration, differentiation and survival (Wells, 1999). EGFR pathway activation plays a fundamental role in malignancy, and recent advances in EGFR-targeted tumor therapy have highlighted several aspects of EGFR signaling and activation in tumorigenesis, including contributions of such factors as genomic amplification, protein expression, mutations, and downstream effectors (Dziadziuszko et al., 2006; Eberhard et al., 2005; Han et al., 2005; Lynch et al., 2004; Oliveira et al., 2006; Paez et al., 2004; Shepherd et al., 2005; Tsao et al., 2005).

Over-expression of the EGFR kinase, or its ligand TGF-alpha, is frequently associated with many cancers, including breast, lung, colorectal, ovarian, renal cell, bladder, head and neck cancers, glioblastomas, and astrocytomas, and is believed to contribute to the malignant growth of these tumors. A specific deletion-mutation in the EGFR gene (EGFRvIII) has also been found to increase cellular tumorigenicity. Activation of EGFR stimulated signaling pathways promote multiple processes that are potentially cancer-promoting, e.g. proliferation, angiogenesis, cell motility and invasion, decreased apoptosis and induction of drug resistance. Increased HER1/EGFR expression is frequently linked to advanced disease, metastases and poor prognosis. For example, in NSCLC and gastric cancer, increased HER1/EGFR expression has been shown to correlate with a high metastatic rate, poor tumor differ.

Intense research efforts are being made to develop anti-tumor agents that directly inhibit the kinase activity of the EGFR and antibodies that reduce EGFR kinase activity by blocking EGFR activation (de Bono J. S. and Rowinsky, E. K. (2002) Trends in Mol. Medicine 8:S19-S26; Dancey, J. and Sausville, E. A. (2003) Nature Rev. Drug Discovery 2:92-313). Several studies have demonstrated, disclosed, or suggested that some EGFR kinase inhibitors might improve tumor cell or neoplasia killing when used in combination with certain other anti-cancer or chemotherapeutic agents or treatments (e.g. Herbst, R. S. et al. (2001) Expert Opin. Biol. Ther. 1:719-732; Solomon, B. et al (2003) Int. J. Radiat. Oncol. Biol. Phys. 55:713-723; Krishnan, S. et al. (2003) Frontiers in Bioscience 8, e1-13; Grunwald, V. and Hidalgo, M. (2003) J. Nat. Cancer Inst. 95:851-867; Seymour L. (2003) Current Opin. Investig. Drugs 4(6):658-666; Khalil, M. Y. et al. (2003) Expert Rev. Anticancer Ther. 3:367-380; Bulgaru, A. M. et al. (2003) Expert Rev. Anticancer Ther. 3:269-279; Dancey, J. and Sausville, E. A. (2003) Nature Rev. Drug Discovery 2:92-313; Ciardiello, F. et al. (2000) Clin. Cancer Res. 6:2053-2063; and Patent Publication No: US 2003/0157104).

Erlotinib (e.g. erlotinib HCl, also known as TARCEVA® or OSI-774) is an orally available inhibitor of EGFR kinase. In vitro, erlotinib has demonstrated substantial inhibitory activity against EGFR kinase in a number of human tumor cell lines, including colorectal and breast cancer (Moyer J. D. et al. (1997) Cancer Res. 57:4838), and preclinical evaluation has demonstrated activity against a number of EGFR-expressing human tumor xenografts (Pollack, V. A. et al (1999) J. Pharmacol. Exp. Ther. 291:739). Erlotinib has demonstrated activity in clinical trials in a number of indications, including head and neck cancer (Soulieres, D., et al. (2004) J. Clin. Oncol. 22:77), NSCLC (Perez-Soler R, et al. (2001) Proc. Am. Soc. Clin. Oncol. 20:310a, abstract 1235), CRC (Oza, M., et al. (2003) Proc. Am. Soc. Clin. Oncol. 22:196a, abstract 785) and MBC (Winer, E., et al. (2002) Breast Cancer Res. Treat. 76:5115a, abstract 445; Jones, R. J., et al. (2003) Proc. Am. Soc. Clin. Oncol. 22:45a, abstract 180). In a phase III trial, erlotinib monotherapy significantly prolonged survival, delayed disease progression and delayed worsening of lung cancer-related symptoms in patients with advanced, treatment-refractory NSCLC (Shepherd, F. et al. (2004) J. Clin. Oncology, 22:14S (July 15 Supplement), Abstract 7022). In November 2004 the U.S. Food and Drug Administration (FDA) approved TARCEVA® for the treatment of patients with locally advanced or metastatic non-small cell lung cancer (NSCLC) after failure of at least one prior chemotherapy regimen.

Despite the significant advancement in the treatment of cancer, improved therapies are still being sought.

SUMMARY OF THE INVENTION

One aspect of the invention provides for a method of inhibiting EGFR signaling in a mammalian cell comprising contacting the cell with a composition comprising an effective amount of a Neuronal Leucine Rich Repeat Protein-1 (NLRR-1) antagonist. In some embodiments the antagonist is an anti-NLRR-1 antibody or an antigen binding fragment thereof, an siRNA, or a small molecule. In some embodiments the antibody is a monoclonal antibody, such as the monoclonal antibody 3D1.6.9, produced from hybridoma cells having ATCC accession number PTA-8732. In other embodiments, the antibody competes for binding with the monoclonal antibody 3D1.6.9 produced from hybridoma cells having ATCC accession number PTA-8732. In yet other embodiments, the antibody binds to the same epitope as the monoclonal antibody 3D1.6.9 produced from hybridoma cells having ATCC accession number PTA-8732. In yet other embodiments, the antibody is a chimeric, human, or humanized antibody. In some embodiments, the chimeric or humanized antibody comprises a fragment from the monoclonal antibody 3D1.6.9 produced from hybridoma cells having ATCC accession number PTA-8732.

In some embodiments, the cell is a cancer cell. In some embodiments, the cell is a breast cancer cell, colorectal cancer cell, lung cancer cell, prostate cancer cell, liver cancer cell, pancreatic cancer cell, or ovarian cancer cell.

Another aspect of the invention provides for a method of inhibiting EGFR signaling in a mammalian cell comprising contacting the cell with a composition comprising an effective amount of an agent that inhibits the interaction of EGFR and NLRR-1. In some embodiments the antagonist is an anti-NLRR-1 antibody or an antigen binding fragment thereof, an siRNA, or a small molecule. In some embodiments the antibody is a monoclonal antibody, such as the monoclonal antibody 3D1.6.9, produced from hybridoma cells having ATCC accession number PTA-8732. In other embodiments, the antibody competes for binding with the monoclonal antibody 3D1.6.9 produced from hybridoma cells having ATCC accession number PTA-8732. In yet other embodiments, the antibody binds to the same epitope as the monoclonal antibody 3D1.6.9 produced from hybridoma cells having ATCC accession number PTA-8732. In yet other embodiments, the antibody is a chimeric, human, or humanized antibody. In some embodiments, the chimeric or humanized antibody comprises a fragment from the monoclonal antibody 3D1.6.9 produced from hybridoma cells having ATCC accession number PTA-8732.

In some embodiments, the cell is a cancer cell. In some embodiments, the cell is a breast cancer cell, colorectal cancer cell, lung cancer cell, prostate cancer cell, liver cancer cell, pancreatic cancer cell, or ovarian cancer cell.

Yet another aspect of the invention provides for a method of inhibiting the growth of tumor cells in a subject, comprising administering to the subject a therapeutically effective amount of a NLRR-1 antagonist. In some embodiments the antagonist is an anti-NLRR-1 antibody or an antigen binding fragment thereof, an siRNA, or a small molecule. In some embodiments the antibody is a monoclonal antibody, such as the monoclonal antibody 3D1.6.9, produced from hybridoma cells having ATCC accession number PTA-8732. In other embodiments, the antibody competes for binding with the monoclonal antibody 3D1.6.9 produced from hybridoma cells having ATCC accession number PTA-8732. In yet other embodiments, the antibody binds to the same epitope as the monoclonal antibody 3D1.6.9 produced from hybridoma cells having ATCC accession number PTA-8732. In yet other embodiments, the antibody is a chimeric, human, or humanized antibody. In some embodiments, the chimeric or humanized antibody comprises a fragment from the monoclonal antibody 3D1.6.9 produced from hybridoma cells having ATCC accession number PTA-8732.

In some embodiments, EGFR is not amplified in the tumor cells. In some embodiments, the subject is further administered a therapeutically effect amount of an EGFR antagonist. In some embodiments, the EGFR antagonist is an anti-EGFR antibody or an antigen binding fragment thereof, an siRNA, or a small molecule. In some embodiments the small molecule is erlotinib. In some embodiments, the tumor cells of the subject are EGFR antagonist resistant. In some embodiments, the tumor cells of the subject are erlotinib resistant. In some embodiments the administration of the NLRR-1 antagonist and the EGFR antagonist increases the inhibition of tumor cell growth as compared to administration of the EGFR antagonist without administration of the NLRR-1 antagonist.

In some embodiments, the tumor cell is a breast cancer cell, a colorectal cancer cell, a lung cancer cell, a prostate cancer cell, a liver cancer cell, a pancreatic cancer cell, or an ovarian cancer cell.

Another aspect of the invention provides for a method of treating cancer in a subject comprising administering to the subject an effective amount of a NLRR-1 antagonist. In some embodiments the antagonist is an anti-NLRR-1 antibody or an antigen binding fragment thereof, an siRNA, or a small molecule. In some embodiments the antibody is a monoclonal antibody, such as the monoclonal antibody 3D1.6.9, produced from hybridoma cells having ATCC accession number PTA-8732. In other embodiments, the antibody competes for binding with the monoclonal antibody 3D1.6.9 produced from hybridoma cells having ATCC accession number PTA-8732. In yet other embodiments, the antibody binds to the same epitope as the monoclonal antibody 3D1.6.9 produced from hybridoma cells having ATCC accession number PTA-8732. In yet other embodiments, the antibody is a chimeric, human, or humanized antibody. In some embodiments, the chimeric or humanized antibody comprises a fragment from the monoclonal antibody 3D1.6.9 produced from hybridoma cells having ATCC accession number PTA-8732.

In some embodiments, EGFR is not amplified in the cancer. In some embodiments, the subject is further administered a therapeutically effect amount of an EGFR antagonist. In some embodiments, the EGFR antagonist is an anti-EGFR antibody or an antigen binding fragment thereof, an siRNA, or a small molecule. In some embodiments the small molecule is erlotinib. In some embodiments, the cancer is EGFR antagonist resistant. In some embodiments, the cancer is erlotinib resistant. In some embodiments the administration of the NLRR-1 antagonist and the EGFR antagonist increases the inhibition of cancer growth as compared to administration of the EGFR antagonist without administration of the NLRR-1 antagonist.

In some embodiments, the cancer is selected from the group consisting of breast cancer, colorectal cancer, lung cancer, prostate cancer, liver cancer, pancreatic cancer, and ovarian cancer.

Another aspect of the invention provides for a method for treating cancer in a patient whose cancer is resistant to treatment with an EGFR antagonist comprising administering to the subject an effective amount of a NLRR-1 antagonist. In some embodiments the antibody is a monoclonal antibody, such as the monoclonal antibody 3D1.6.9, produced from hybridoma cells having ATCC accession number PTA-8732. In other embodiments, the antibody competes for binding with the monoclonal antibody 3D1.6.9 produced from hybridoma cells having ATCC accession number PTA-8732. In yet other embodiments, the antibody binds to the same epitope as the monoclonal antibody 3D1.6.9 produced from hybridoma cells having ATCC accession number PTA-8732. In yet other embodiments, the antibody is a chimeric, human, or humanized antibody. In some embodiments, the chimeric or humanized antibody comprises a fragment from the monoclonal antibody 3D1.6.9 produced from hybridoma cells having ATCC accession number PTA-8732.

In some embodiments, EGFR is not amplified in the cancer. In some embodiments, the subject is further administered a therapeutically effect amount of an EGFR antagonist. In some embodiments, the EGFR antagonist is an anti-EGFR antibody or an antigen binding fragment thereof, an siRNA, or a small molecule. In some embodiments the small molecule is erlotinib. In some embodiments, the cancer is EGFR antagonist resistant. In some embodiments, the cancer is erlotinib resistant. In some embodiments the administration of the NLRR-1 antagonist and the EGFR antagonist increases the inhibition of cancer growth as compared to administration of the EGFR antagonist without administration of the NLRR-1 antagonist.

In some embodiments, the cancer is selected from the group consisting of breast cancer, colorectal cancer, lung cancer, prostate cancer, liver cancer, pancreatic cancer, and ovarian cancer.

Yet another aspect of the invention provides for a method for identifying patients that could benefit from treatment with an NLRR-1 antagonist comprising comparing the level of NLRR-1 present in a test cell population isolated from a patient and a reference cell population wherein an increase in NLRR-1 expression level in the test cell population indicates that the patient could benefit from treatment with an NLRR-1 antagonist.

Another aspect of the invention provides for a method for identifying patients that could benefit from a combination treatment with an NLRR-1 antagonist and an EGFR antagonist comprising comparing the level of NLRR-1 present in a test cell population isolated from a patient and a reference cell population, wherein the test cell population does not comprise EGFR amplification, and wherein an increase in NLRR-1 expression level in the test cell population indicates that the patient could benefit from a combination treatment of an NLRR-1 antagonist and an EGFR antagonist.

or NLRR-1 siRNA (□). R, resistant to erlotinib (IC50>8 μM); S, sensitive to erlotinib (IC50<2 μM).

FIG. 9 shows NLRR-1 and NLRR-3 transcript expression. 9A: RT-PCR analysis of NLRR-1 in Multiple Myeloma (MM). Multiple myeloma RNA was isolated from CD138+ purified cells from bone marrow. Data represents quantity calculated using a human genomic DNA standard curve. hu BM, human bone marrow (Clontech); hu spleen, human spleen (Clontech); normal B, normal B cells (Clontech); LnCAP, prostate tumor cell line. 9B: NLRR-3 expression in normal (N) vs. tumor (T) tissues as measured by microarray analysis.

FIG. 10 shows transcript level comparison in various tumors. 10A: CBL vs. EGFR in 2003 tumors as measured by microarray analysis. 10B: E-cadherin (CDH1) vs. EGFR in 2003 tumors as measured by microarray analysis.

Figure 11A:
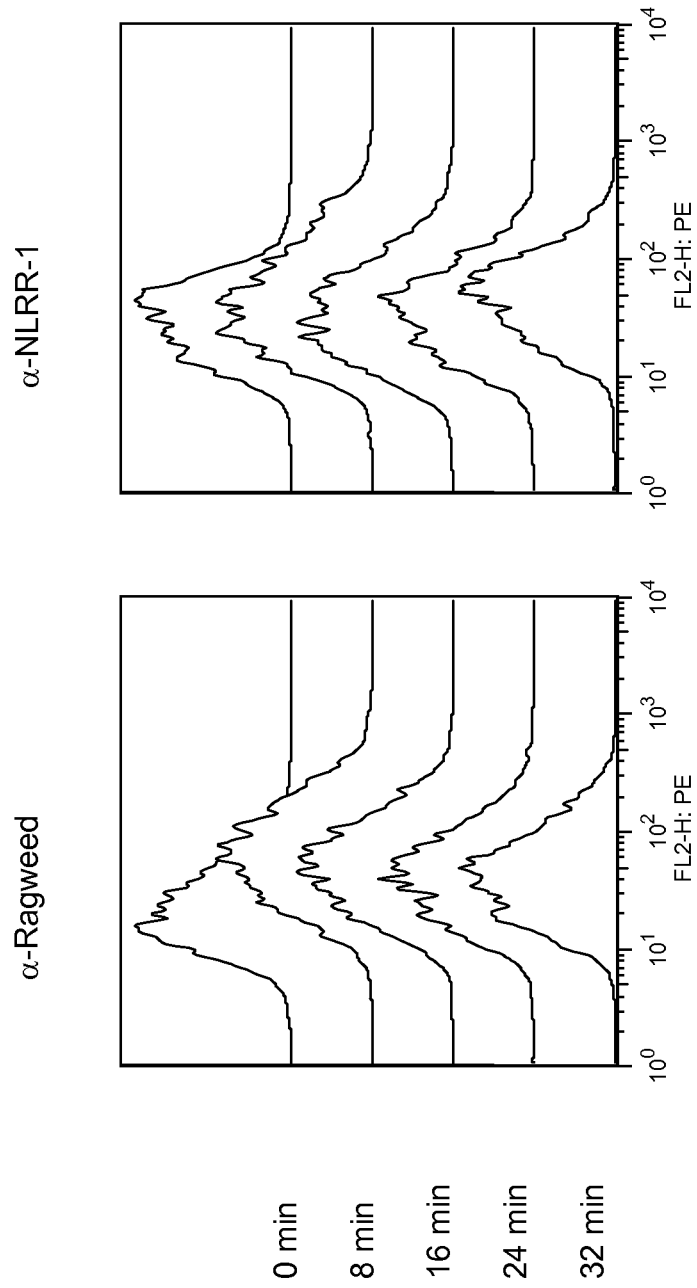

FIG. 11 shows ERK phosphorylation with α-ragweed and α-NLRR-1 antibodies. 11A: Flow cytometry plots of phosphorylated ERK following treatment with α-ragweed or α-NLRR-1 monoclonal antibody, starvation, and stimulation with 10% serum. 5,000 to 10,000 events were collected and cells were gated on FSC and SSC. 11B: Summary of α-NLRR-1 antibody inhibition of ERK phosphorylation with 10% serum stimulation over 5 independently conducted experiments graphed as a percentage of α-ragweed control. Data represents mean±SE. One tailed T-test results are statistically significant (*) at 8 minutes, p=0.013 and at 16 minutes p=0.023. 11C: NCI-H520 ERK phosphorylation with serum stimulation as measured by flow cytometry. α-ragweed (ϒ); α-NLRR-1 (▲).

FIG. 12 shows NLRR-1 and ΔC YFP fusions. 12A: Diagram of fusion protein constructs: white box: NLRR-1 extracellular domain, hatched box: transmembrane region, black box: clathrin mediated endocytosis motif, shaded box: YFP. 12B: Detection of NLRR-1 by flow cytometry of fusion proteins: HEK293 cells were transiently transfected with pEYFP vector, NLRR-1.YFP, or NLRR-1ΔC.YFP and stained with α-NLRR-1 monoclonal antibody followed by α-mouse Ig-alexa 647 secondary. 10,000 events were collected and cells were gated FSC, SSC, PI, and YFP.

Figure 13A:
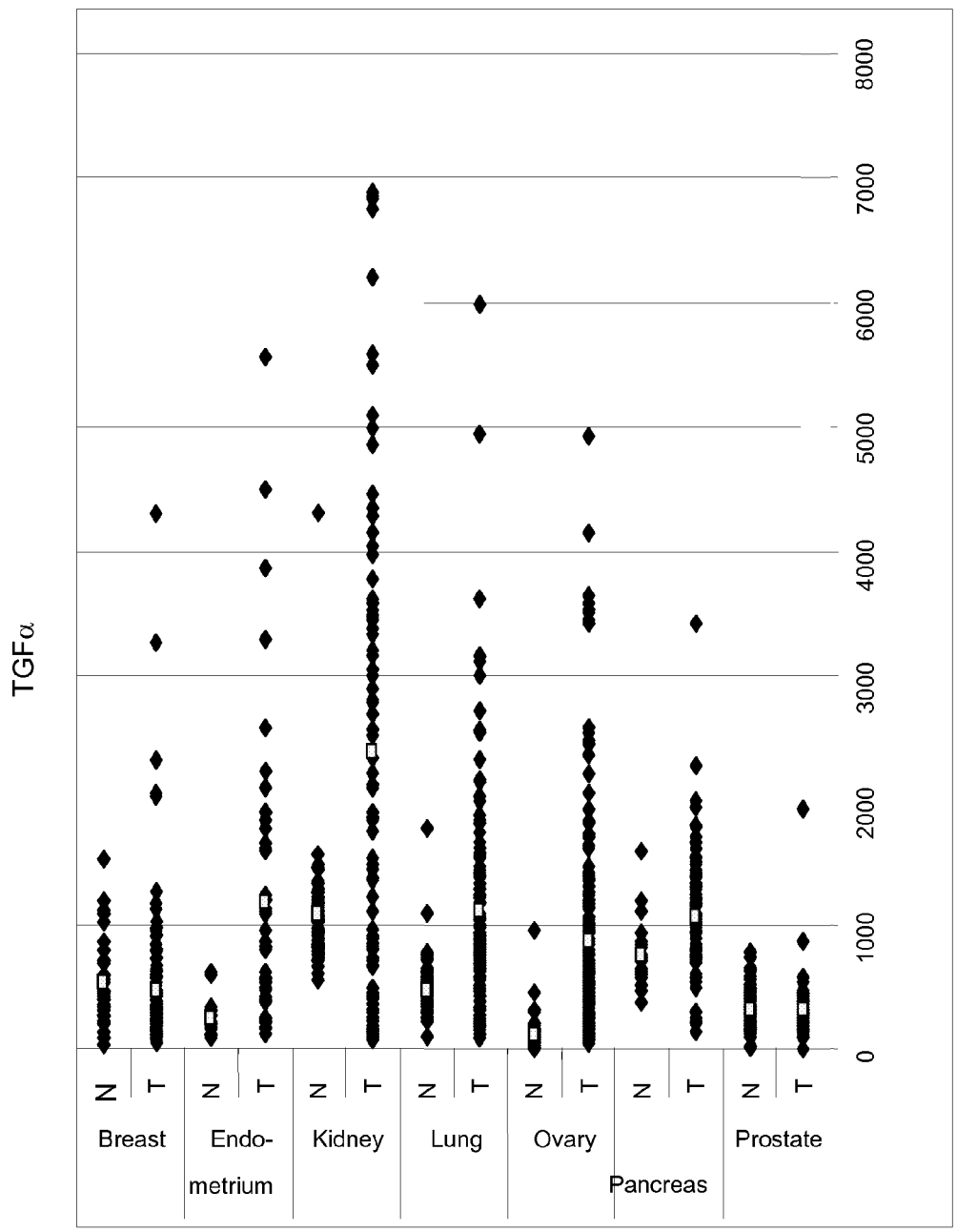
Figure 13B:
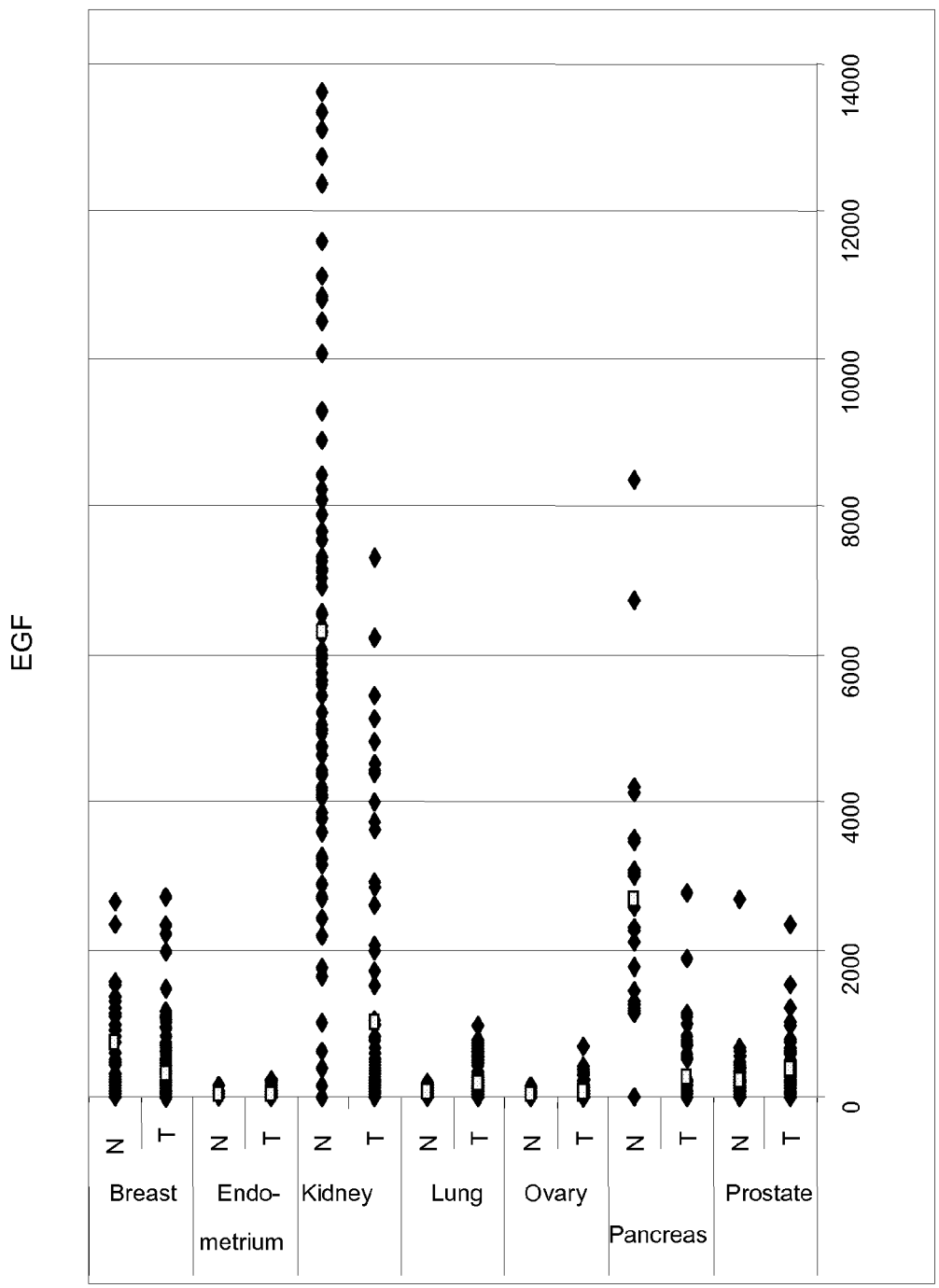

FIG. 13 shows transcript levels of TGFα (13A) and EGF (13B) in normal (N) and tumor (T) tissues as measured by microarray analysis.

Figure 14:
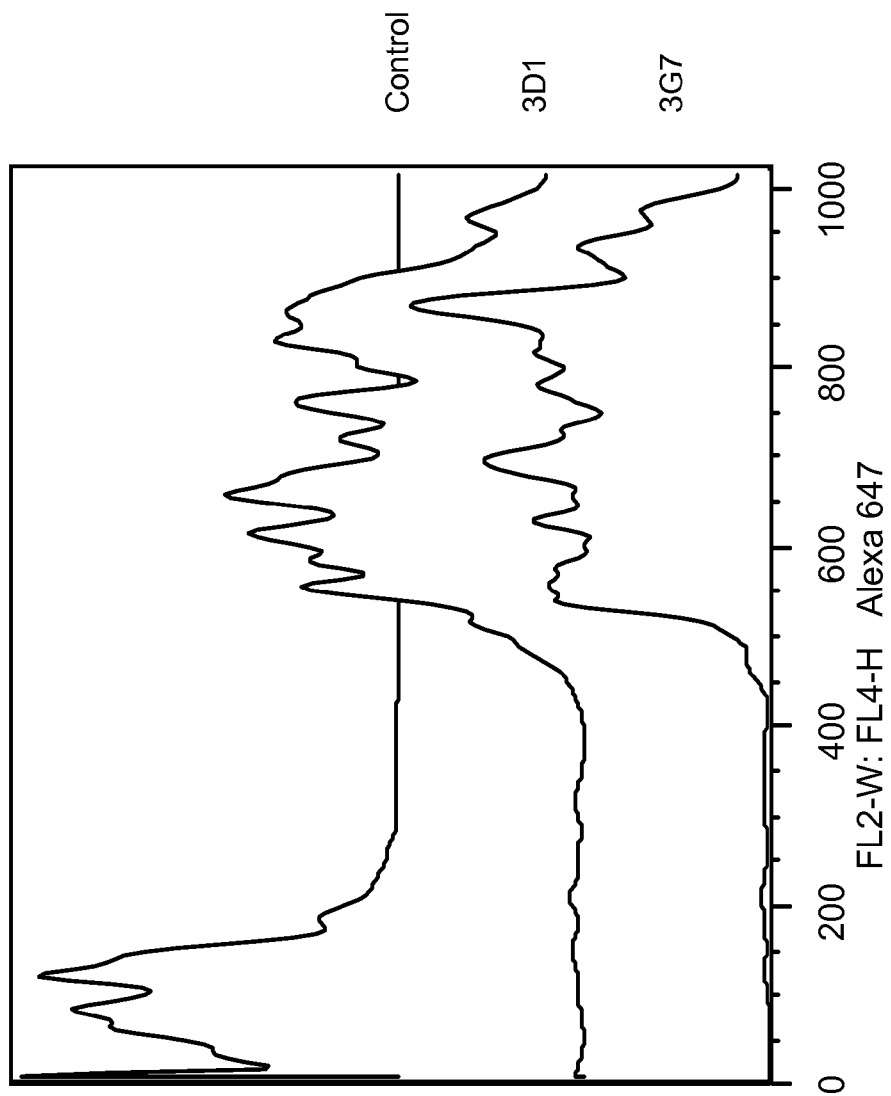

FIG. 14 shows HEK293 cells transiently transfected with NLRR-1.YFP stained with α-NLRR-1 monoclonal antibodies followed by α-mouse Ig-alexa 647 secondary, and analyzed by flow cytometry. 10,000 events were collected and cells were gated on FSC, SSC, PI, and YFP.

FIG. 15 shows the amino acid sequence (SEQ ID NO: 1) of human NLRR-1.

DETAILED DESCRIPTION

Definitions

The term "Neuronal Leucine Rich Repeat" or "NLRR", as used herein, refers, unless indicated otherwise, to any native or variant (whether native or synthetic) NLRR polypeptide. In general, the NLRR protein family contains 11 or 12 LRRs, an immunoglobulin domain, and a type III fibronectin domain (Bormann et al., 1999; Fukamachi et al., 2001; Hayata et al., 1998). Members of the NLRR family include NLRR-1, NLRR-2, NLRR-3, NLRR-4, NLRR-5, and NLRR-6. Human NLRR-1 has been isolated and characterized. See, for example, Genebank accession number AAQ88679, U.S. Pat. No. 7,189,813, and US Patent Publication No. 20050208523, and US Patent Publication No. 20060002943, the disclosures of which are incorporated by reference in their entirety herein. The nucleic acid sequence and amino acid sequence of human NLRR-1 are presented in FIG. 15.

The term "wild type NLRR" generally refers to a polypeptide comprising the amino acid sequence of a naturally occurring NLRR protein. The term "wild type NLRR sequence" generally refers to an amino acid sequence found in a naturally occurring NLRR.

The term "NLRR variant" as used herein refers to a NLRR polypeptide which includes one or more amino acid mutations in the native NLRR sequence. Optionally, the one or more amino acid mutations include amino acid substitution(s).

A "native sequence" polypeptide comprises a polypeptide having the same amino acid sequence as a polypeptide derived from nature. Thus, a native sequence polypeptide can have the amino acid sequence of naturally-occurring polypeptide from any mammal. Such native sequence polypeptide can be isolated from nature or can be produced by recombinant or synthetic means. The term "native sequence" polypeptide specifically encompasses naturally-occurring truncated or secreted forms of the polypeptide (e.g., an extracellular domain sequence), naturally-occurring variant forms (e.g., alternatively spliced forms) and naturally-occurring allelic variants of the polypeptide.

A polypeptide "variant" means a biologically active polypeptide having at least about 80% amino acid sequence identity with the native sequence polypeptide. Such variants include, for instance, polypeptides wherein one or more amino acid residues are added, or deleted, at the N- or C-terminus of the polypeptide. Ordinarily, a variant will have at least about 80% amino acid sequence identity, more preferably at least about 90% amino acid sequence identity, and even more preferably at least about 95% amino acid sequence identity with the native sequence polypeptide.

By "EGFR" is meant the receptor tyrosine kinase polypeptide Epidermal Growth Factor Receptor which is described in Ullrich et al, Nature (1984) 309:418425, alternatively referred to as Her-1 and the c-erbB gene product, as well as variants thereof such as EGFRvIII. Variants of EGFR also include deletional, substitutional and insertional variants, for example those described in Lynch et al (New England Journal of Medicine 2004, 350:2129), Paez et al (Science 2004, 304: 1497), Pao et al (PNAS 2004, 101:13306).

A "biological sample" (interchangeably termed "sample" or "tissue or cell sample") encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

A "NLRR-1 antagonist" (interchangeably termed "NLRR-1 inhibitor") is an agent that interferes with NLRR-1 function. Examples of NLRR-1 antagonists include antibodies that bind to NLRR-1 ("anti-NLRR-1 antibodies"); small molecule NLRR-1 antagonists; antisense and inhibitory RNA (e.g., shRNA or siRNA) molecules. Preferably, the NLRR-1 antagonist is an antibody or small molecule which binds to NLRR-1. In a particular embodiment, a NLRR-1 antagonist has a binding affinity (dissociation constant) to NLRR-1 of about 1,000 nM or less. In another embodiment, a NLRR-1 antagonist has a binding affinity to NLRR-1 of about 100 nM or less. In another embodiment, a RLL-1 antagonist has a binding affinity to NLRR-1 of about 50 nM or less. In a particular embodiment, a NLRR-1 antagonist inhibits NLRR-1 with an IC50 of 1,000 nM or less. In another embodiment, a NLRR-1 antagonist inhibits NLRR-1 with an IC50 of 500 nM or less. In another embodiment, a NLRR-1 antagonist inhibits NLRR-1 with an IC50 of 50 nM or less.

An "EGFR antagonist" (interchangeably termed "EGFR inhibitor") is an agent that interferes with EGFR activation or function. Examples of EGFR antagonists include EGFR antibodies that bind to EGFR ("anti-EGFR antibodies"); EGFR ligand antibodies; small molecule EGFR antagonists; EGFR tyrosine kinase inhibitors; antisense and inhibitory RNA (e.g., shRNA and siRNA) molecules (see, for example, WO2004/87207). Preferably, the EGFR antagonist is an antibody or small molecule which binds to EGFR. In some embodiments, the EGFR antagonist is an EGFR-targeted drug. In a particular embodiment, an EGFR antagonist has a binding affinity (dissociation constant) to EGFR of about 1,000 nM or less. In another embodiment, an EGFR antagonist has a binding affinity to EGFR of about 100 nM or less. In another embodiment, an EGFR antagonist has a binding affinity to EGFR of about 50 nM or less. In a particular embodiment, an EGFR antagonist inhibits EGFR signaling with an IC50 of 1,000 nM or less. In another embodiment, an EGFR antagonist inhibits EGFR signaling with an IC50 of 500 nM or less. In another embodiment, an EGFR antagonist inhibits EGFR signaling with an IC50 of 50 nM or less.

EGFR antagonists include therapeutic agents that bind to EGFR and inhibit EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., J. Biol. Chem. 279(29):30375-30384 (2004)). The anti-EGFR antibody may be conjugated with a cytotoxic agent, thus generating an immunoconjugate (see, e.g., EP659,439A2, Merck Patent GmbH).

EGFR antagonists also include small molecules such as compounds described in U.S. Pat. No. 5,616,582, U.S. Pat. No. 5,457,105, U.S. Pat. No. 5,475,001, U.S. Pat. No. 5,654, 307, U.S. Pat. No. 5,679,683, U.S. Pat. No. 6,084,095, U.S. Pat. No. 6,265,410, U.S. Pat. No. 6,455,534, U.S. Pat. No. 6,521,620, U.S. Pat. No. 6,596,726, U.S. Pat. No. 6,713,484, U.S. Pat. No. 5,770,599, U.S. Pat. No. 6,140,332, U.S. Pat. No. 5,866,572, U.S. Pat. No. 6,399,602, U.S. Pat. No. 6,344,459, U.S. Pat. No. 6,602,863, U.S. Pat. No. 6,391,874, WO9814451, WO9850038, WO9909016, WO9924037, WO9935146, WO0132651, U.S. Pat. No. 6,344,455, U.S. Pat. No. 5,760,041, U.S. Pat. No. 6,002,008, U.S. Pat. No. 5,747,498. Particular small molecule EGFR antagonists include OSI-774 (CP-358774, erlotinib, OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); Iressa® (ZD1839, gefitinib, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide); lapatinib (Tykerb, GlaxoSmithKline); ZD6474 (Zactima, AstraZeneca); CUDC-101 (Curis); canertinib (CI-1033); AEE788 (6-[4-[(4-ethyl-1-piperazinyl)methyl]phenyl]-N-[(1R)-1-phenylethyl]-7H-pyrrolo[2,3-d]pyrimidin-4-amine, WO2003013541, Novartis) and PKI166 4-[4-[[(1R)-1-phenylethyl]amino]-7H-pyrrolo[2,3-d]pyrimidin-6-yl]-phenol, WO9702266 Novartis).

"EGFR activation" refers to activation, or phosphorylation, of EGFR. Generally, EGFR activation results in signal transduction (e.g. that caused by an intracellular kinase domain of EGFR receptor phosphorylating tyrosine residues in EGFR or a substrate polypeptide). EGFR activation may be mediated by EGFR ligand binding to a EGFR dimer comprising EGFR. EGFR ligand binding to a EGFR dimer may activate a kinase domain of one or more of the EGFR in the dimer and thereby results in phosphorylation of tyrosine residues in one or more of the EGFR and/or phosphorylation of tyrosine residues in additional substrate polypeptides(s).

By "EGFR antagonist resistant" cancer or a cancer that is "resistant to treatment with an EGFR antagonist" is meant that the cancer patient has progressed while receiving an EGFR antagonist therapy (i.e., the patient is "EGFR refractory"), or the patient has progressed within 12 months (for instance, within one, two, three, or six months) after completing an EGFR antagonist-based therapy regimen. For example, cancers which incorporate T790M mutant EGFR are resistant to erlotinib and gefitinib therapy. An "EGFR antagonist resistant" tumor cell means a tumor cell that does not respond to treatment with an EGFR antagonist. For example, the tumor cell continues to survive after treatment with the EGFR antagonist and does not undergo apoptosis.

By "erlotinib resistant" cancer or cancer that is "resistant to treatment with erlotinib" is meant that the cancer patient has progressed while receiving erlotinib-based therapy (i.e., the patient is "erlotinib refractory"), or the patient has progressed within 12 months (for instance, within one, two, three, or six months) after completing an erlotinib-based therapy regimen. A "erlotinib resistant" tumor cell means a tumor cell that does not respond to treatment with erlotinib. For example, the tumor cell continues to survive after treatment with erlotinib and does not undergo apoptosis.

The term "ligand-independent" as used herein, as for example applied to receptor signaling activity, refers to signaling activity that is not dependent on the presence of a ligand. For example, EGFR signaling may result from dimerization with other members of the HER family such as HER2. A receptor having ligand-independent kinase activity will not necessarily preclude the binding of ligand to that receptor to produce additional activation of the kinase activity.

The term "constitutive" as used herein, as for example applied to receptor kinase activity, refers to continuous signaling activity of a receptor that is not dependent on the presence of a ligand or other activating molecules. For example, EGFR variant III (EGFRvIII) which is commonly found in glioblastoma multiforme has deleted much of its extracellular domain. Although ligands are unable to bind EGFRvIII it is nevertheless continuously active and is associated with abnormal proliferation and survival. Depending on the nature of the receptor, all of the activity may be constitutive or the activity of the receptor may be further activated by the binding of other molecules (e.g. ligands). Cellular events that lead to activation of receptors are well known among those of ordinary skill in the art. For example, activation may include oligomerization, e.g., dimerization, trimerization, etc., into higher order receptor complexes. Complexes may comprise a single species of protein, i.e., a homomeric complex. Alternatively, complexes may comprise at least two different protein species, i.e., a heteromeric complex. Complex formation may be caused by, for example, overexpression of normal or mutant forms of receptor on the surface of a cell. Complex formation may also be caused by a specific mutation or mutations in a receptor.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

A cancer or biological sample which "displays EGFR expression, amplification, or activation" is one which, in a diagnostic test, expresses (including overexpresses) EGFR, has amplified EGFR gene, and/or otherwise demonstrates activation or phosphorylation of EGFR.

A cancer or biological sample which "does not display EGFR expression, amplification, or activation" is one which, in a diagnostic test, does not express (including overexpress) EGFR, does not have amplified EGFR gene, and/or otherwise does not demonstrate activation or phosphorylation of EGFR.

A cancer or biological sample which "displays EGFR activation" is one which, in a diagnostic test, demonstrates activation or phosphorylation of EGFR. Such activation can be determined directly (e.g. by measuring EGFR phosphorylation by ELISA) or indirectly.

A cancer or biological sample which "does not display EGFR activation" is one which, in a diagnostic test, does not demonstrate activation or phosphorylation of EGFR. Such activation can be determined directly (e.g. by measuring EGFR phosphorylation by ELISA) or indirectly.

A cancer or biological sample which "displays EGFR amplification" is one which, in a diagnostic test, has amplified EGFR gene.

A cancer cell with "EGFR overexpression or amplification" is one which has significantly higher levels of EGFR protein or gene compared to a noncancerous cell of the same tissue type. Such overexpression may be caused by gene amplification or by increased transcription or translation. EGFR overexpression or amplification may be determined in a diagnostic or prognostic assay by evaluating increased levels of the EGFR protein present on the surface of a cell (e.g. via an immunohistochemistry assay; IHC). Alternatively, or additionally, one may measure levels of EGFR-encoding nucleic acid in the cell, e.g. via fluorescent in situ hybridization (FISH; see WO98/45479 published October, 1998), southern blotting, or polymerase chain reaction (PCR) techniques, such as quantitative real time PCR (qRT-PCR). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

A cancer cell which "does not overexpress or amplify EGFR" is one which does not have higher than normal levels of EGFR protein or gene compared to a noncancerous cell of the same tissue type.

The term "mutation", as used herein, means a difference in the amino acid or nucleic acid sequence of a particular protein or nucleic acid (gene, RNA) relative to the wild-type protein or nucleic acid, respectively. A mutated protein or nucleic acid can be expressed from or found on one allele (heterozygous) or both alleles (homozygous) of a gene, and may be somatic or germ line. In the instant invention, mutations are generally somatic. Mutations include sequence rearrangements such as insertions, deletions, and point mutations (including single nucleotide/amino acid polymorphisms).

To "inhibit" is to decrease or reduce an activity, function, and/or amount as compared to a reference.

Protein "expression" refers to conversion of the information encoded in a gene into messenger RNA (mRNA) and then to the protein.

Herein, a sample or cell that "expresses" a protein of interest is one in which mRNA encoding the protein, or the protein, including fragments thereof, is determined to be present in the sample or cell.

An "immunoconjugate" (interchangeably referred to as "antibody-drug conjugate," or "ADC") means an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. The Fc sequence of an immunoglobulin generally comprises two constant domains, a CH2 domain and a CH3 domain, and optionally comprises a CH4 domain. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

By "Fc polypeptide" herein is meant one of the polypeptides that make up an Fc region. An Fc polypeptide may be obtained from any suitable immunoglobulin, such as $IgG_1$, $IgG_2$, $IgG_3$, or $IgG_4$ subtypes, IgA, IgE, IgD or IgM. In some embodiments, an Fc polypeptide comprises part or all of a wild type hinge sequence (generally at its N terminus). In some embodiments, an Fc polypeptide does not comprise a functional or wild type hinge sequence.

The "hinge region," "hinge sequence", and variations thereof, as used herein, includes the meaning known in the art, which is illustrated in, for example, Janeway et al., Immuno Biology: the immune system in health and disease, (Elsevier Science Ltd., NY) (4th ed., 1999); Bloom et al., Protein Science (1997), 6:407-415; Humphreys et al., J. Immunol. Methods (1997), 209:193-202.

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

The term "antibody" is used in the broadest sense and specifically covers monoclonal antibodies (including full length monoclonal antibodies), polyclonal antibodies, multispecific antibodies (e.g., bispecific antibodies), monovalent antibodies, multivalent antibodies, and antibody fragments so long as they exhibit the desired biological activity.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment. In one embodiment, an antibody of the invention is a one-armed antibody as described in WO2005/063816. In one embodiment, the one-armed antibody comprises Fc mutations constituting "knobs" and "holes" as described in WO2005/063816. For example, a hole mutation can be one or more of T366A, L368A and/or Y407V in an Fc polypeptide, and a cavity mutation can be T366W.

A "blocking" antibody or an antibody "antagonist" is one which inhibits or reduces biological activity of the antigen it binds. Preferred blocking antibodies or antagonist antibodies completely inhibit the biological activity of the antigen.

Unless indicated otherwise, the expression "multivalent antibody" is used throughout this specification to denote an antibody comprising three or more antigen binding sites. The multivalent antibody is preferably engineered to have the three or more antigen binding sites and is generally not a native sequence IgM or IgA antibody.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). In some instances, a complementarity determining region can include amino acids from both a CDR region defined according to Kabat and a hypervariable loop. For example, the CDRH1 of the heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

The "Fab" fragment contains a variable and constant domain of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the V$_H$ and V$_L$ domains of antibody, wherein these domains are present in a single polypeptide chain. Generally the Fv polypeptide further comprises a polypeptide linker between the V$_H$ and V$_L$ domains, which enables the scFv to form the desired structure for antigen binding. For a review of scFv, see Pluckthun in *The Pharmacology of Monoclonal Antibodies*, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain (V$_H$) connected to a light chain variable domain (V$_L$) in the same polypeptide chain (V$_H$ and V$_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The expression "linear antibodies" refers to the antibodies described in Zapata et al., *Protein Eng.*, 8(10):1057-1062 (1995). Briefly, these antibodies comprise a pair of tandem Fd segments (V$_H$-C$_H$1-V$_H$-C$_H$1) which, together with complementary light chain polypeptides, form a pair of antigen binding regions. Linear antibodies can be bispecific or monospecific.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. *Nature Biotechnology* 14:309-314 (1996): Sheets et al. *Proc. Natl. Acad. Sci.* 95:6157-6162 (1998)); Hoogenboom and Winter, *J. Mol. Biol.*, 227:381 (1991); Marks et al., *J. Mol. Biol.*, 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10: 779-783 (1992); Lonberg et al., *Nature* 368: 856-859 (1994); Morrison, *Nature* 368:812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., *J. Immunol.*, 147 (1):86-95 (1991); and U.S. Pat. No. 5,750,373.

A "naked antibody" is an antibody that is not conjugated to a heterologous molecule, such as a cytotoxic moiety or radiolabel.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al., *J. Mol. Biol.* 226:889-896 (1992).

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in Antibodies, A Laboratory Manual, Cold Spring Harbor Laboratory, Ed Harlow and David Lane (1988), can be performed.

To increase the half-life of the antibodies or polypeptide containing the amino acid sequences of this invention, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence of this invention so that the fusion protein expressed by the engineered nucleic acid molecule comprises the salvage receptor binding epitope and a polypeptide sequence of this invention. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule (e.g., Ghetie et al., *Ann. Rev. Immunol.* 18:739-766 (2000), Table 1). Antibodies with substitutions in an Fc region thereof and increased serum half-lives are also described in WO00/42072, WO 02/060919; Shields et al., *J. Biol. Chem.* 276: 6591-6604 (2001); Hinton, *J. Biol. Chem.* 279:6213-6216 (2004)). In another embodiment, the serum half-life can also be increased, for example, by attaching other polypeptide sequences. For example, antibodies or other polypeptides useful in the methods of the invention can be attached to serum albumin or a portion of serum albumin that binds to the FcRn receptor or a serum albumin binding peptide so that serum albumin binds to the antibody or polypeptide, e.g., such polypeptide sequences are disclosed in WO01/45746.

An "isolated" polypeptide or "isolated" antibody is one that has been identified and separated and/or recovered from a component of its natural environment. Contaminant components of its natural environment are materials that would interfere with diagnostic or therapeutic uses for the polypeptide or antibody, and may include enzymes, hormones, and other proteinaceous or nonproteinaceous solutes. In preferred embodiments, the polypeptide or antibody will be purified (1) to greater than 95% by weight of polypeptide or antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide or antibody includes the polypeptide or antibody in situ within recombinant cells since at least one component of the polypeptide's natural environment will not be present. Ordinarily, however, isolated polypeptide or antibody will be prepared by at least one purification step.

By "fragment" is meant a portion of a polypeptide or nucleic acid molecule that contains, preferably, at least 10%, 20%, 30%, 40%, 50%, 60%, 70%, 80%, 90%, 95%, 98%, or more of the entire length of the reference nucleic acid molecule or polypeptide. A fragment may contain 10, 20, 30, 40, 50, 60, 70, 80, 90, or 100, 200, 300, 400, 500, 600, or more nucleotides or 10, 20, 30, 40, 50, 60, 70, 80, 90, 100, 120, 140, 160, 180, 190, 200 amino acids or more.

"Treatment" refers to both therapeutic treatment and prophylactic or preventative measures. Those in need of treatment include those already having a benign, precancerous, or non-metastatic tumor as well as those in which the occurrence or recurrence of cancer is to be prevented.

The term "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, I, or II cancer. Examples of cancer include, but are not limited to, carcinoma, lymphoma, myeloma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer.

The term "cancer" includes hematopoietic cancers or blood-related cancers, such as lymphoma, leukemia, myeloma or lymphoid malignancies, and also cancers of the spleen and cancers of the lymph nodes. More particular examples of such B-cell associated cancers, including for example, high, intermediate and low grade lymphomas (including B cell lymphomas such as, for example, mucosα-associated-lymphoid tissue B cell lymphoma and non-Hodgkin's lymphoma, mantle cell lymphoma, Burkitt's lymphoma, small lymphocytic lymphoma, marginal zone lymphoma, diffuse large cell lymphoma, follicular lymphoma, and Hodgkin's lymphoma and T cell lymphomas) and leukemias (including secondary leukemia, chronic lymphocytic leukemia, such as B cell leukemia (CD5+B lymphocytes), myeloid leukemia, such as acute myeloid leukemia, chronic myeloid leukemia, lymphoid leukemia, such as acute lymphoblastic leukemia and myelodysplasia), multiple myeloma, such as plasma cell malignancy, and other hematological and/or B cell- or T-cell-associated cancers. Also included are cancers of additional hematopoietic cells, including polymorphonuclear leukocytes, such as basophils, eosinophils, neutrophils and monocytes, dendritic cells, platelets, erythrocytes and natural killer cells. The origins of B-cell cancers are as follows: marginal zone B-cell lymphoma origins in memory B-cells in marginal zone, follicular lymphoma and diffuse large B-cell lymphoma originates in centrocytes in the light zone of germinal centers, multiple myeloma originates in plasma cells, chronic lymphocytic leukemia and small lymphocytic leukemia originates in B1 cells (CD5+), mantle cell lymphoma originates in naive B-cells in the mantle zone and Burkitt's lymphoma originates in centroblasts in the dark zone of germinal centers. Tissues which include hematopoietic cells referred herein to as "hematopoietic cell tissues" include thymus and bone marrow and peripheral lymphoid tissues, such as spleen, lymph nodes, lymphoid tissues associated with mucosa, such as the gut-associated lymphoid tissues, tonsils, Peyer's patches and appendix and lymphoid tissues associated with other mucosa, for example, the bronchial linings.

The term "pre-cancerous" refers to a condition or a growth that typically precedes or develops into a cancer. A "pre-cancerous" growth will have cells that are characterized by abnormal cell cycle regulation, proliferation, or differentiation, which can be determined by markers of cell cycle regulation, cellular proliferation, or differentiation.

By "dysplasia" is meant any abnormal growth or development of tissue, organ, or cells. Preferably, the dysplasia is high grade or precancerous.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass.

Both stimulatory and inhibitory molecular pathways within the tumor cell regulate this behavior, and interactions between the tumor cell and host cells in the distant site are also significant.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

By "primary tumor" or "primary cancer" is meant the original cancer and not a metastatic lesion located in another tissue, organ, or location in the subject's body.

By "benign tumor" or "benign cancer" is meant a tumor that remains localized at the site of origin and does not have the capacity to infiltrate, invade, or metastasize to a distant site.

By "tumor burden" is meant the number of cancer cells, the size of a tumor, or the amount of cancer in the body. Tumor burden is also referred to as tumor load.

By "tumor number" is meant the number of tumors.

By "subject" or "patient" is meant a mammal, including, but not limited to, a human or non-human mammal, such as a bovine, equine, canine, ovine, or feline. Preferably, the subject or patient is a human.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem. Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N. J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery,* Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

Methods and Compositions

The invention identifies certain novel properties and activities of NLRR-1 that may be exploited using the methods of the invention for therapeutic purposes.

As disclosed herein, NLRR-1 associates with the EGFR signaling complex and promotes MAP kinase activation in response to TGFα, indicting that NLRR-1 plays a significant role in EGFR signaling. Furthermore, association with NLRR-1 promotes internalization of EGFR. Signaling from the internalized EGFR complex can amplify MAP kinase phosphorylation and stimulate pathways leading to cell survival (Haugh et al., 1999a; Haugh et al., 1999b; Sato et al., 2001; Schoeberl et al., 2002; Wang et al., 2002), consistent with the observations of increased apoptosis on depletion of NLRR-1 from tumor cells. Additionally, NLRR-1 may associate with the EGFR/ERBB2 heterodimer.

Accordingly, one aspect of the invention provides for a method of inhibiting EGFR signaling in a mammalian cell comprising contacting the cell with a NLRR-1 antagonist. The level of EGFR signaling is reduced upon contact with the NLRR-1 antagonist.

Another aspect of the invention provides for a method of inhibiting EGFR signaling in a mammalian cell comprising contacting the cell with an agent that inhibits the interaction of EGFR with NLRR-1. Inhibition of the interaction between EGFR and NLRR-1 by the agent results in a reduction of EGFR signaling.

Figure 9A:
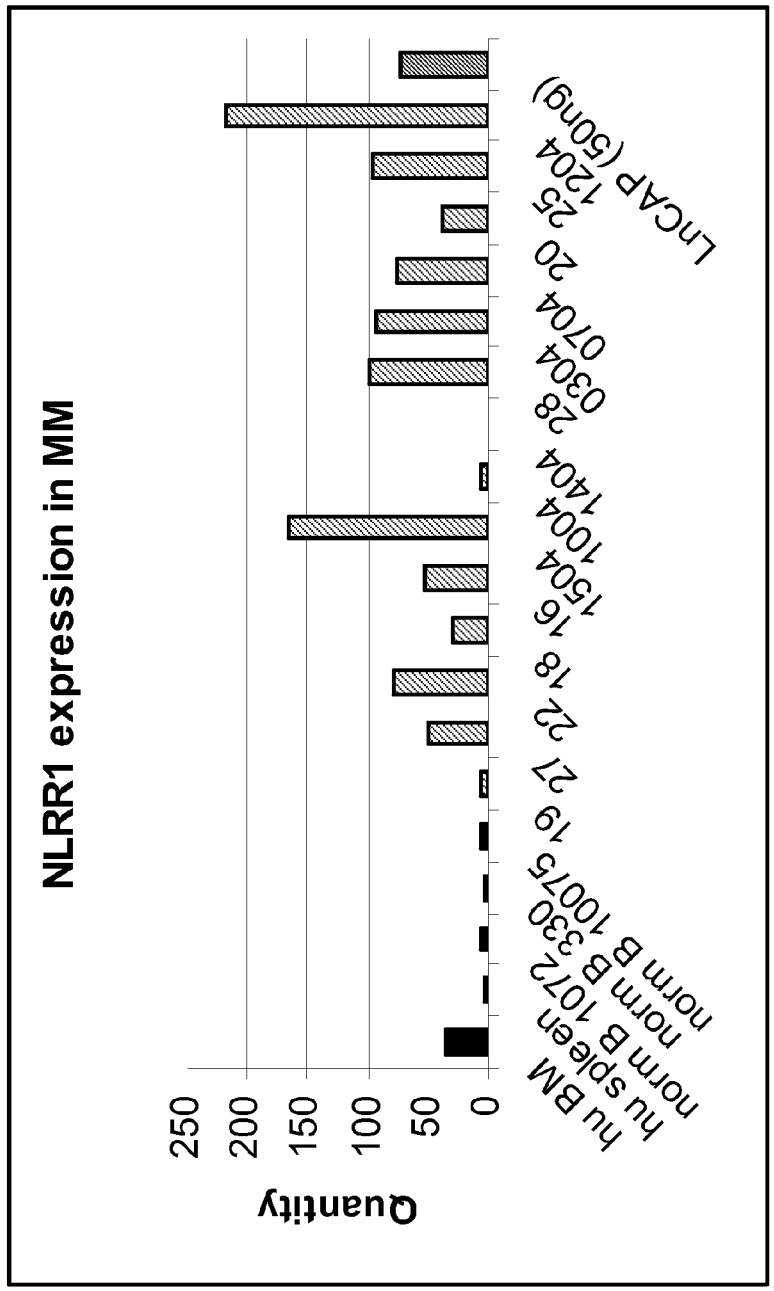

Widespread expression of NLRR-1, a homolog of NLRR-3, is observed in a variety of tumors, and, in a more detailed transcript analysis of prostate tumors, expression was correlated with high Gleason score and an independently-characterized marker of poor prognosis, MUC1 (Andren et al., 2006a; Lapointe et al., 2004). As set forth in the Examples, NLRR-1 is expressed not only in prostate tumors but across a range of epithelial tumors, and even some aggressive hematological malignancies such as multiple myeloma and mantle cell lymphoma (FIG. 2A,B; FIG. 9A) as well as in pancreatic, breast, lung, and metastatic colon.

TGFα is frequently found to be over-expressed across a variety of tumor types, is correlated with more aggressive disease and poor prognosis, can function in either autocrine or paracrine modalities, and is a potent activator of EGFR signaling (Ebner and Derynck, 1991; El-Obeid et al., 2002; Jhappan et al., 1990; Jiang et al., 1998; Maeda et al., 2002; Martinez-Arca et al., 2005; O'Dwyer P and Benson, 2002; Scher et al., 1995; Wang et al., 1998) (FIG. 13A,B). The attenuation of both MAP kinase and PI3 kinase pathway activation using a monoclonal antibody specific for NLRR-1, in response to serum or TGFα, indicates an important role for NLRR-1 in EGFR pathway activation in tumor cells.

As shown in the Examples, depletion of NLRR-1 in lung tumor cell lines results in decreased growth and increased apoptosis at all levels of endogenous NLRR-1 expression, indicating that cancerous cells have significant dependence on NLRR-1 for their viability. The expression of NLRR-1 is inversely correlated to elevated EGFR across tumors indicating that NLRR-1 activates EGFR pathway signaling in tumor cells in the absence of amplified EGFR. Additionally, depletion of NLRR-1 in lung tumor cell lines promotes apoptosis upon treatment with the EGFR inhibitor Erlotinib. A significant increase in sensitivity was apparent for the otherwise erlotinib-resistant cell line NCI-H647 and synergy between the NLRR-1 knockdown and erlotinib was observed for resistant cell lines. This data indicates that NLRR-1 plays a significant role in EGFR signaling and that NLRR-1 could contribute to the resistance exhibited by some tumors to EGFR kinase inhibitors such as erlotinib.

Accordingly, another aspect of the invention provides for a method of inhibiting the growth of tumor cells in a subject, comprising administering to the subject a therapeutically effective amount of a NLRR-1 antagonist. In some embodiments, the tumor cells express EGFR. In other embodiments, the tumor cells express EGFR but the expression of EGFR is not amplified.

Yet another aspect of the invention provides for a method of treating cancer in a subject comprising administering to the subject an effective amount of a NLRR-1 antagonist. In some embodiments, the cells of the cancer express EGFR. In other embodiments, the cells of the cancer express EGFR but the expression of EGFR is not amplified.

In certain embodiments, an EGFR antagonist is administered to the subject in addition to the NLRR-1 antagonist. In some embodiments, the tumor cell or the cancer to be treated is resistant to treatment with an EGFR antagonist. In another embodiment, the EGFR antagonist administered with the NLRR-1 antagonist is erlotinib. In another embodiment, the tumor cell or the cancer to be treated is resistant to treatment with erlotinib. In other embodiments, the administration of the NLRR-1 antagonist and the EGFR antagonist increases the inhibition of tumor cell or cancer growth as compared to administration of either antagonist alone. In other embodiments, the increase in inhibition of tumor growth or cancer with the combination treatment is synergistic as compared to treatment with the NLRR-1 antagonist or EGFR antagonist alone.

The term cancer embraces a collection of proliferative disorders, including but not limited to pre-cancerous growths, benign tumors, and malignant tumors. The cancers to be treated by the above methods include those cancers that comprise a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia), myeloma (multiple myeloma), or lymphoma (e.g., non-Hodgkin's lymphoma, cutaneous T-cell lymphoma, mantle cell lymphoma, or Hodgkin's disease). A solid tumor includes any cancer of body tissues other than blood, bone marrow, or the lymphatic system. Solid tumors can be further divided into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors.

The invention also provides compositions comprising the above compounds, both singly and in combination, as described further herein. The compositions are useful for treating a pathological condition, such as tumor, in a subject.

NLRR-1 Antagonists

NLRR-1 antagonists useful in the methods of the invention include polypeptides that specifically bind to NLRR-1, NLRR-1 antibodies (anti-NLRR-1 antibodies), small molecules, receptor molecules and derivatives, such as immunoadhesins, which bind specifically to NLRR-1, and fusions proteins. NLRR-1 antagonists also include antagonistic variants of NLRR-1 polypeptides, RNA aptamers and peptibodies against NLRR-1. Examples of each of these are described below.

Anti-NLRR-1 antibodies that are useful in the methods of the invention include any antibody that binds with sufficient affinity and specificity to NLRR-1 and can reduce or inhibit NLRR-1 activity or inhibit the association of NLRR-1 with EGFR or any member of the EGFR pathway, including, HER2, HER3, and HER4. The antibody selected will normally have a sufficiently strong binding affinity for NLRR-1, for example, the antibody may bind human NLRR-1 with a Kd value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. Preferably, the anti-NLRR-1 antibody of the invention can be used as a therapeutic agent in targeting and interfering with diseases or conditions wherein NLRR-1/EGFR activity is involved. Also, the antibody may be subjected to other biological activity assays, e.g., in order to evaluate its effectiveness as a therapeutic. Such assays are known in the art and depend on the target antigen and intended use for the antibody.

In certain embodiments, the anti-NLRR-1 antibody is the monoclonal antibody produced by the hybridoma cell line deposited under American Type Culture Collection Accession Number ATCC PTA-8732 (hybridoma 3D1.6.9). In other embodiments, the antibody comprises a fragment of the monoclonal antibody produced by the hybridoma cell line deposited under American Type Culture Collection Accession Number ATCC PTA-8732 (hybridoma 3D1.6.9). In other embodiments, the antibody comprises one or more of the CDR sequences of the monoclonal antibody produced by the hybridoma cell line deposited under American Type Culture Collection Accession Number ATCC PTA-8732 (hybridoma 3D1.6.9). In other embodiments, the antibody competes for binding monoclonal antibody produced by the hybridoma cell line deposited under American Type Culture Collection Accession Number ATCC PTA-8732 (hybridoma 3D1.6.9). In other embodiments, the antibody binds to the same epitope as the monoclonal antibody produced by the hybridoma cell line deposited under American Type Culture Collection Accession Number ATCC PTA-8732 (hybridoma 3D1.6.9).

NLRR-1 polypeptides or fragments thereof that specifically bind to EGFR, or other members of the EGFR pathway, can be used in the methods of the invention, e.g., to bind to and sequester the EGFR protein, thereby preventing it from signaling. Preferably, the NLRR-1 polypeptides or fragment thereof, is a soluble form. In some embodiments, a soluble form of the polypeptide exerts an inhibitory effect on the biological activity of the EGFR protein by binding to EGFR, thereby preventing it from associating with its natural ligands.

Aptamers are nucleic acid molecules that form tertiary structures that specifically bind to a target molecule, such as a NLRR-1 polypeptide. The generation and therapeutic use of aptamers are well established in the art. See, e.g., U.S. Pat. No. 5,475,096. Additional information on aptamers can be found in U.S. Patent Application Publication No. 20060148748.

A peptibody is a peptide sequence linked to an amino acid sequence encoding a fragment or portion of an immunoglobulin molecule. Polypeptides may be derived from randomized sequences selected by any method for specific binding, including but not limited to, phage display technology. In a preferred embodiment, the selected polypeptide may be linked to an amino acid sequence encoding the Fc portion of an immunoglobulin. Peptibodies that specifically bind to and antagonize NLRR-1 are also useful in the methods of the invention.

EGFR Antagonists

EGFR antagonists include antibodies such as humanized monoclonal antibody known as nimotuzumab (YM Biosciences), fully human ABX-EGF (panitumumab, Abgenix Inc.) as well as fully human antibodies known as E1.1, E2.4, E2.5, E6.2, E6.4, E2.11, E6.3 and E7.6.3 and described in U.S. Pat. No. 6,235,883; MDX-447 (Medarex Inc). Pertuzumab (2C4) is a humanized antibody that binds directly to HER2 but interferes with HER2-EGFR dimerization thereby inhibiting EGFR signaling. Other examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., *J. Biol. Chem.* 279(29):30375-30384 (2004)). The anti-EGFR antibody may be conjugated with a cytotoxic agent, thus generating an immunoconjugate (see, e.g., EP659, 439A2, Merck Patent GmbH).

Anti-EGFR antibodies that are useful in the methods of the invention include any antibody that binds with sufficient affinity and specificity to EGFR and can reduce or inhibit EGFR activity. The antibody selected will normally have a sufficiently strong binding affinity for EGFR, for example, the antibody may bind human EGFR with a Kd value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. Preferably, the anti-EGFR antibody of the invention can be used as a therapeutic agent in targeting and interfering with diseases or conditions wherein EGFR/EGFR ligand activity is involved. Also, the antibody may be subjected to other biological activity assays, e.g., in order to evaluate its effectiveness as a therapeutic. Such assays are known in the art and depend on the target antigen and intended use for the antibody.

Bispecific antibodies are antibodies that have binding specificities for at least two different epitopes. Exemplary bispecific antibodies may bind to EGFR and to NLRR-1. In another example, an exemplary bispecific antibody may bind to two different epitopes of the same protein, e.g., NLRR-1 protein. Alternatively, a NLRR-1 or EGFR arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the NLRR-1 or EGFR-expressing cell. Bispecific antibodies may also be used to localize cytotoxic agents to cells which express EGFR or NLRR-1. These antibodies possess a EGFR or NLRR-1-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

EGFR antagonists also include small molecules such as compounds described in U.S. Pat. No. 5,616,582, U.S. Pat. No. 5,457,105, U.S. Pat. No. 5,475,001, U.S. Pat. No. 5,654,307, U.S. Pat. No. 5,679,683, U.S. Pat. No. 6,084,095, U.S. Pat. No. 6,265,410, U.S. Pat. No. 6,455,534, U.S. Pat. No. 6,521,620, U.S. Pat. No. 6,596,726, U.S. Pat. No. 6,713,484, U.S. Pat. No. 5,770,599, U.S. Pat. No. 6,140,332, U.S. Pat. No. 5,866,572, U.S. Pat. No. 6,399,602, U.S. Pat. No. 6,344,459, U.S. Pat. No. 6,602,863, U.S. Pat. No. 6,391,874, WO9814451, WO9850038, WO9909016, WO9924037, WO9935146, WO0132651, U.S. Pat. No. 6,344,455, U.S. Pat. No. 5,760,041, U.S. Pat. No. 6,002,008, U.S. Pat. No. 5,747,498. Particular small molecule EGFR antagonists include OSI-774 (CP-358774, erlotinib, OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); Iressa® (ZD1839, gefitinib, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide); lapatinib (Tykerb, GlaxoSmithKline); ZD6474 (Zactima, AstraZeneca); CUDC-101 (Curis); canertinib (CI-1033); AEE788 (6-[4-[(4-ethyl-1-piperazinyl)methyl]phenyl]-N-[(1R)-1-phenyl-ethyl]-7H-pyrrolo[2,3-d]pyrimidin-4-amine, WO2003013541, Novartis) and PKI166 4-[4-[[(1R)-1-phenylethyl]amino]-7H-pyrrolo[2,3-d]pyrimidin-6-yl]-phenol, WO9702266 Novartis).

Antibodies

Antibodies of the invention include antibodies the specifically binds to a protein of the invention and antibody fragment of such antibodies. Exemplary antibodies include, e.g., polyclonal, monoclonal, humanized, fragment, bispecific, multispecific, heteroconjugated, multivalent, effector function-containing, etc., antibodies.

Polyclonal Antibodies

The antibodies of the invention can comprise polyclonal antibodies. Methods of preparing polyclonal antibodies are known to the skilled artisan. For example, polyclonal antibodies against an antibody of the invention are raised in animals by one or multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

In one embodiment, animals are immunized against a molecule of the invention, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Typically, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies against an antigen described herein can be made using the hybridoma method first described by Kohler et al., *Nature*, 256:495 (1975), or may be made by recombinant DNA methods (see, e.g., U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that typically contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Typical myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the target of interest. The binding specificity of monoclonal antibodies produced by hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107: 220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. The monoclonal antibodies may also be made by recombinant DNA methods, such as those described in U.S. Pat. No. 4,816,567. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In another embodiment, antibodies or antibody fragments can be isolated from antibody phage libraries generated using the techniques described in McCafferty et al., *Nature*, 348: 552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized and Human Antibodies

Antibodies of the invention can comprise humanized antibodies or human antibodies. A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a typical method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992). Human antibodies can also be derived from phage-display libraries (Hoogenboom et al., *J. Mol. Biol.*, 227:381 (1991); Marks et al., *J. Mol. Biol.*, 222:581-597 (1991); Vaughan et al. *Nature Biotech* 14:309 (1996)).

Human antibodies can also be produced using various techniques known in the art, including phage display libraries (Hoogenboom and Winter, *J. Mol. Biol.*, 227:381 (1991); Marks et al., *J. Mol. Biol.*, 222:581 (1991)). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, K S. and Chiswell, D J., *Cur Opin*

*in Struct Biol* 3:564-571 (1993). Several sources of V-gene segments can be used for phage display. For example, Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated, e.g., by essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.,* 147(1):86-95 (1991)). Human antibodies may also be generated by in vitro activated B cells (see U.S. Pat. Nos. 5,567,610 and 5,229,275).

Antibody Fragments

Antibody fragments are also included in the invention. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science,* 229: 81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to one of ordinary skill in the art. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. SFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

Multispecific Antibodies (e.g., Bispecific)

Antibodies of the invention also include, e.g., multispecific antibodies, which have binding specificities for at least two different antigens. While such molecules normally will only bind two antigens (i.e. bispecific antibodies, BsAbs), antibodies with additional specificities such as trispecific or other multispecific (i.e., four or more specificities encompassed in one molecule) antibodies are encompassed by this expression when used herein. Examples of BsAbs known in the art include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptor: CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. In certain aspects of the invention one of the antibodies in the bispecific antibody can be coupled to a macrophage-specific cellular marker and the other to a dendritic cell-specific cellular marker. In certain embodiments, such an antibody would bind more tightly to a cell bearing both the given macrophage-specific cellular marker and the given dendritic cell-specific cellular marker than to a cell bearing only one or the other marker.

Bispecific antibodies can be prepared as full length antibodies or antibody fragments (e.g. F(ab')$_2$ bispecific antibodies). Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described, e.g., in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Techniques for generating bispecific antibodies from antibody fragments are also known in the art. For example, bispecific antibodies can be prepared using chemical linkage. Brennan et al., *Science,* 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al., *J. Exp. Med.,* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the VEGF receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are also contemplated. For example, trispecific antibodies can be prepared. Tutt et al. *J. Immunol.* 147: 60 (1991).

Heteroconjugate Antibodies

Bispecific antibodies include cross-linked or "heteroconjugate" antibodies, which are antibodies of the invention. Such bispecific antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in, e.g., U.S. Pat. No. 4,676,980, along with a number of cross-linking techniques.

Multivalent Antibodies

Antibodies of the invention include a multivalent antibody. A multivalent antibody may be internalized (and/or catabolized) faster than a bivalent antibody by a cell expressing an antigen to which the antibodies bind. The antibodies of the invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. Multivalent antibodies may have multiple binding sites for the same antigen, or binding sites for two or more different antigens.

Effector Function Engineering

It may be desirable to modify the antibody of the invention with respect to effector function, so as to enhance the effectiveness of the antibody in treating a particular disorder or disease. For example, a cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Immunoconjugates

The invention also pertains to immunoconjugates comprising an antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate). A variety of radionuclides are available for the production of radioconjugate antibodies. Examples include, but are not limited to, e.g., $^{212}Bi$, $^{131}I$, $^{131}In$, $^{90}Y$ and $^{186}Re$.

Chemotherapeutic agents useful in the generation of such immunoconjugates have been described above. For example, BCNU, streptozoicin, vincristine, 5-fluorouracil, the family of agents known collectively LL-E33288 complex described in U.S. Pat. Nos. 5,053,394, 5,770,710, esperamicins (U.S. Pat. No. 5,877,296), etc. (see also the definition of chemotherapeutic agents herein) can be conjugated to antibodies of the invention or fragments thereof.

For selective destruction of the tumor, the antibody may comprise a highly radioactive atom. A variety of radioactive isotopes are available for the production of radioconjugated antibodies or fragments thereof. Examples include, but are not limited to, e.g., $^{211}At$, $^{131}I$, $^{125}I$, $^{90}Y$, $^{186}Re$, $^{188}Re$, $^{153}Sm$, $^{212}Bi$, $^{32}P$, $^{212}Pb$, $^{111}In$, radioactive isotopes of Lu, etc. When the conjugate is used for diagnosis, it may comprise a radioactive atom for scintigraphic studies, for example $^{99m}tc$ or $^{123}I$, or a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $^{99m}tc$ or $^{123}I$, $^{186}Re$, $^{188}Re$ and $^{111}In$ can be attached via a cysteine residue in the peptide. Yttrium-90 can be attached via a lysine residue. The IODOGEN method (Fraker et al (1978) *Biochem. Biophys. Res. Commun.* 80: 49-57 can be used to incorporate iodine-123. See, e.g., *Monoclonal Antibodies in Immunoscintigraphy* (Chatal, CRC Press 1989) which describes other methods in detail.

Enzymatically active toxins and fragments thereof which can be used include diphtheria A chain, nonbinding active fragments of diphtheria toxin, anthrax toxin protective antigen, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, neomycin, and the tricothecenes. See, e.g., WO 93/21232 published Oct. 28, 1993.

Conjugates of the antibody and cytotoxic agent can be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208, 020) may be used.

Alternatively, a fusion protein comprising the anti-VEGF, and/or the anti-protein of the invention antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In certain embodiments, the antibody is conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In certain embodiments, an immunoconjugate is formed between an antibody and a compound with nucleolytic activity (e.g., a ribonuclease or a DNA endonuclease such as a deoxyribonuclease; Dnase).

Maytansine and Maytansinoids

The invention further provides an antibody of the invention conjugated to one or more maytansinoid molecules. Maytansinoids are mitotic inhibitors which act by inhibiting tubulin polymerization. Maytansine was first isolated from the east African shrub *Maytenus serrata* (U.S. Pat. No. 3,896, 111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256, 746; 4,260,608; 4,265,814; 4,294,757; 4,307,016; 4,308,268; 4,308,269; 4,309,428; 4,313,946; 4,315,929; 4,317,821;

4,322,348; 4,331,598; 4,361,650; 4,364,866; 4,424,219; 4,450,254; 4,362,663; and 4,371,533.

An antibody of the invention can be conjugated to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208, 020 and in the other patents and nonpatent publications referred to hereinabove. In one embodiment, maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Typical coupling agents include N-succinimidyl-3-(2-pyridyldithio) propionate (SPDP) (Carlsson et al., *Biochem. J.* 173:723-737 [1978]) and N-succinimidyl-4-(2-pyridylthio) pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. The linkage is formed at the C-3 position of maytansinol or a maytansinol analogue.

Calicheamicin

Another immunoconjugate of interest comprises an antibody of the invention conjugated to one or more calicheamicin molecules. The calicheamicin family of antibiotics is capable of producing double-stranded DNA breaks at subpicomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Antibody Modifications

Other modifications of an antibody of the invention are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules, or in macroemulsions. Such techniques are disclosed in *Remington's Pharmaceutical Sciences,* 16th edition, Oslo, A., Ed., (1980).

Combination Therapies

The present invention provides for a combination use of a NLRR-1 antagonist and an EGFR antagonist as part of a specific treatment regimen intended to provide a beneficial effect or synergistic effect from the combined activity of these therapeutic agents. The beneficial effect of the combination includes, but is not limited to, pharmacokinetic or pharmacodynamic co-action resulting from the combination of therapeutic agents.

In some embodiments, the tumor cell or the cancer to be treated with the NLRR-1 antagonist and the EGFR antagonist is resistant to treatment with an EGFR antagonist in the absence of treatment with a NLRR-1 antagonist. In another embodiment, the EGFR antagonist administered with the NLRR-1 antagonist is erlotinib. In another embodiment, the tumor cell or the cancer to be treated with the NLRR-1 antagonist and erlotinib is resistant to treatment with erlotinib in the absence of treatment with a NLRR-1 antagonist. In other embodiments, the administration of the NLRR-1 antagonist and the EGFR antagonist increases the inhibition of tumor cell or cancer growth as compared to administration of the EGFR antagonist without administration of the NLRR-1 antagonist. In other embodiments, the increase in inhibition of tumor or cancer growth using the combination therapy is synergistic as compared to treatment with either the NLRR-1 antagonist or EGFR antagonist alone.

The combined administration includes coadministration or concurrent administration, using separate formulations or a single pharmaceutical formulation, and consecutive administration in either order, wherein preferably there is a time period while both (or all) active agents simultaneously exert their biological activities.

Diagnostics

NLRR-1 is expressed in many different tumors and its expression anti-correlates with elevated EGFR expression indicating that NLRR-1 facilitates EGFR pathway signaling and provides a means of increasing pathway activation without requiring amplification of EGFR. Furthermore, NLRR-1 expression is correlated to the resistance encountered in some tumors to EGFR antagonists, such as erlotinib. Knockdown of NLRR-1 expression in EGFR antagonist resistant cancer cells results in increased sensitivity to treatment with EGFR-targeted drug therapy.

Accordingly, one aspect of the invention also provides for methods and compositions for diagnosing cell proliferative disorders, such as cancer. In some embodiments, the method comprises comparing the level of NLRR-1 present in a test cell population and reference cell population wherein an increase in NLRR-1 expression level in the test cell population indicates that it contains cancerous cells.

Another aspect of the invention provides for a method of determining whether a test cell population has an activated EGFR pathway in the absence of EGFR amplification. In some embodiments, the method comprises comparing the level of NLRR-1 present in a test cell population that does not have EGFR amplification and a reference cell population wherein an increase in NLRR-1 expression level indicates that the EGFR pathway is activated. This method is useful in identifying patients likely to be resistant to treatment with an EGFR antagonist due to the lack of EGFR amplification but that could benefit from a combination treatment of an NLRR-1 antagonist and an EGFR antagonist.

In the above methods, the test cell population can be any number of cells, i.e., one or more cells, and can be provided in vitro, in vivo, or ex vivo. In certain embodiments, cells in the reference cell population are derived from a tissue type as similar as possible to that of the test sample, e.g., tumor cell population. In some embodiments, the reference cell population is derived from the same subject as the test cell population, e.g., from a region proximal to the region of origin of the test cell population. In some embodiments, the reference cell population is derived from the same tissue type as the test cell population, but was collected from the subject at a different time (e.g., from a time earlier than the test cell population). In some embodiments, a series of reference cell population samples are collected at regular time intervals from the subject (e.g., daily, weekly, monthly, or yearly). In one embodiment of the invention, the reference cell population is derived from a plurality of cells. For example, the reference cell population can be a database of NLRR-1 expression patterns from previously tested cells.

Alternatively, a control can be generated by determining the expression of a housekeeping gene (such as an actin family member) in a reference cell population. The housekeeping gene acts as a comparative control on which to determine overexpression of the NLRR-1 gene.

In other embodiments, the levels of EGFR are also determined in the test and reference cell population.

Protein and Nucleic Acid Detection Methods

Detecting the presence, activity, or amount of a protein of the invention can be readily performed using methods known in the art. Expression can be measured at the protein level, i.e., by measuring the levels of polypeptides. Such methods are well known in the art and include, e.g., immunoassays based on antibodies to the proteins. Expression levels of one or more of the protein sequences in the test cell population can be compared to expression levels of the sequences in one or more cells from a reference cell population. Expression of sequences in test and control populations of cells can be compared using any art-recognized method for comparing expression of nucleic acid sequences. For example, expression can be compared using GENECALLING™ methods as described in U.S. Pat. No. 5,871,697 and in Shimkets et al., Nat. Biotechnol. 17:798-803. In certain embodiments of the invention, expression of one, two or more, three or more, four or more, five or more, six or more, seven or more, eight or more, nine or more, ten or more, eleven or more, twelve or more, thirteen or more, fourteen or more, fifteen or more, 20 or more, 25 or more protein sequences are measured.

Various assay techniques known in the art may also be employed, such as competitive binding assays, direct or indirect sandwich assays and immunoprecipitation assays conducted in either heterogeneous or homogeneous phases (Zola, *Monoclonal Antibodies: A Manual of Techniques*, CRC Press, Inc. (1987) pp. 147-158). Antibodies or antigen-binding fragments thereof used in the assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. And Cytochem.*, 30:407 (1982).

Nucleic acid detection techniques are also well known in the art, and may be employed to assess the presence of mRNA encoding NLRR-1 and thus to determine the presence or amount of NLRR-1 in a cell population from which the cell sample was drawn. Methods commonly known in the art of recombinant DNA technology which can be used to assess the presence, amount, or activity of nucleic acids are described, e.g., in Ausubel et al. eds. (1993) *Current Protocols in Molecular Biology*, John Wiley & Sons, NY; and Kriegler (1990) *Gene Transfer and Expression, A Laboratory Manual*, Stockton Press, NY. Examples of such techniques include fluorescent in situ hybridization (FISH; see WO98/45479 published October, 1998), southern blotting, or polymerase chain reaction (PCR) techniques, such as quantitative real time PCR (qRT-PCR).

Optionally, comparison of differentially expressed sequences between a test cell population and a reference cell population can be done with respect to a control nucleic acid whose expression is independent of the parameter or condition being measured. Expression levels of the control nucleic acid in the test and reference nucleic acid can be used to normalize signal levels in the compared populations. Suitable control nucleic acids can readily be determined by one of ordinary skill in the art.

Chemotherapeutic Agents

The combination therapy of the invention can further comprise one or more chemotherapeutic agent(s). The combined administration includes coadministration or concurrent administration, using separate formulations or a single pharmaceutical formulation, and consecutive administration in either order, wherein preferably there is a time period while both (or all) active agents simultaneously exert their biological activities.

The chemotherapeutic agent, if administered, is usually administered at dosages known therefor, or optionally lowered due to combined action of the drugs or negative side effects attributable to administration of the antimetabolite chemotherapeutic agent. Preparation and dosing schedules for such chemotherapeutic agents may be used according to manufacturers' instructions or as determined empirically by the skilled practitioner.

Various chemotherapeutic agents that can be combined are disclosed above. Preferred chemotherapeutic agents to be combined are selected from the group consisting of a taxoid (including docetaxel and paclitaxel), vinca (such as vinorelbine or vinblastine), platinum compound (such as carboplatin or cisplatin), aromatase inhibitor (such as letrozole, anastrazole, or exemestane), anti-estrogen (e.g. fulvestrant or tamoxifen), etoposide, thiotepa, cyclophosphamide, methotrexate, liposomal doxorubicin, pegylated liposomal doxorubicin, capecitabine, gemcitabine, COX-2 inhibitor (for instance, celecoxib), or proteosome inhibitor (e.g. PS342).

Formulations, Dosages and Administrations

The therapeutic agents used in the invention will be formulated, dosed, and administered in a fashion consistent with good medical practice. Factors for consideration in this context include the particular disorder being treated, the particular subject being treated, the clinical condition of the individual patient, the cause of the disorder, the site of delivery of the agent, the method of administration, the scheduling of administration, the drug-drug interaction of the agents to be combined, and other factors known to medical practitioners.

Therapeutic formulations are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The therapeutic agents of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In the case of VEGF antagonists, local administration is particularly desired if extensive side effects or toxicity is associated with VEGF antagonism. An ex vivo strategy can also be used for therapeutic applications. Ex vivo strategies involve transfecting or transducing cells obtained from the subject with a polynucleotide encoding a NLRR-1 or EGFR antagonist. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

For example, if the NLRR-1 or EGFR antagonist is an antibody, the antibody is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic.

In another example, the NLRR-1 or EGFR antagonist compound is administered locally, e.g., by direct injections, when the disorder or location of the tumor permits, and the injections can be repeated periodically. The NLRR-1 or EGFR antagonist can also be delivered systemically to the subject or directly to the tumor cells, e.g., to a tumor or a tumor bed following surgical excision of the tumor, in order to prevent or reduce local recurrence or metastasis.

Administration of the therapeutic agents in combination typically is carried out over a defined time period (usually minutes, hours, days or weeks depending upon the combination selected). Combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner.

The therapeutic agent can be administered by the same route or by different routes. For example, the NLRR-1 antagonist in the combination may be administered by intravenous injection while the EGFR inhibitor in the combination may be administered orally. Alternatively, for example, both of the therapeutic agents may be administered orally, or both therapeutic agents may be administered by intravenous injection, depending on the specific therapeutic agents. The sequence in which the therapeutic agents are administered also varies depending on the specific agents.

Depending on the type and severity of the disease, about 1 μg/kg to 100 mg/kg (e.g., 0.1-20 mg/kg) of each therapeutic agent is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until the cancer is treated, as measured by the methods described above. However, other dosage regimens may be useful. In one example, if the NLRR-1 or EGFR antagonist is an antibody, the antibody of the invention is administered every two to three weeks, at a dose ranging from about 5 mg/kg to about 15 mg/kg. If the NLRR-1 or EGFR antagonist is an oral small molecule compound, the drug is administered daily at a dose ranging from about 25 mg/kg to about 50 mg/kg. Moreover, the oral compound of the invention can be administered either under a traditional high-dose intermittent regimen, or using lower and more frequent doses without scheduled breaks (referred to as "metronomic therapy"). When an intermittent regimen is used, for example, the drug can be given daily for two to three weeks followed by a one week break; or daily for four weeks followed by a two week break, depending on the daily dose and particular indication. The progress of the therapy of the invention is easily monitored by conventional techniques and assays.

The present application contemplates administration of the NLRR-1 or EGFR antagonist by gene therapy. See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429-4432 (1987); and Wagner et al., *Proc. Natl. Acad. Sci. USA* 87:3410-3414 (1990). For review of the currently known gene marking and gene therapy protocols see Anderson et al., *Science* 256:808-813 (1992). See also WO 93/25673 and the references cited therein.

Articles of Manufacture

In another embodiment of the invention, an article of manufacture containing materials useful for the treatment of the disorders or diagnosing the disorders described above is provided. The article of manufacture comprises a container, a label and a package insert. Suitable containers include, for example, bottles, vials, syringes, etc. The containers may be formed from a variety of materials such as glass or plastic. In one embodiment, the container holds a composition which is effective for treating the condition and may have a sterile access port (for example the container may be an intravenous solution bag or a vial having a stopper pierceable by a hypodermic injection needle). In one embodiment, at least one active agent in the composition is a NLRR-1 antagonist. In certain embodiments, the composition further includes an EGFR antagonist. In another embodiment the composition includes a NLRR-1 antagonist and at least a second active molecule including, but not limited to, a chemotherapeutic agent, a cytokine, a chemokine, an anti-angiogenic agent, an immunosuppressive agent, a cytotoxic agent, and a growth inhibitory agent. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. The articles of manufacture of the invention may further include other materials desirable from a commercial and user standpoint, including additional active agents, other buffers, diluents, filters, needles, and syringes. The article of manufacture may further include instructions that the NLRR-1 antagonist is to be used in connection with a diagnostic that has identified the patient as having a cancer that does not have amplified EGFR. The article of manufacture may further include instructions that the composition is for use on patients whose cancers are resistant to EGFR-targeted therapies.

Deposit of Material

Cultures of the monoclonal antibody mumab 3D1.6.9 have been deposited with the American Type Culture Collection, 10801 University Blvd., Manassas, Va., USA (ATCC) on Oct. 24, 2007, and designated PTA-8732.

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of the deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S.

Commissioner of Patents and Trademarks to be entitled thereto according to 35 USC §122 and the Commissioner's rules pursuant thereto (including 37 CFR §1.12 with particular reference to 886 OG 638).

In respect of those designations in which a European patent is sought, a sample of the deposited microorganism will be made available until the publication of the mention of the grant of the European patent or until the date on which the application has been refused or withdrawn or is deemed to be withdrawn, only by the issue of such a sample to an expert nominated by the person requesting the sample. (Rule 28(4) EPC)

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiments are intended to illustrate only certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that they represent. Indeed, various modifications of the invention in addition to those shown and described herein will become apparent to those skilled in the art from the foregoing description and fall within the scope of the appended claims.

The following examples are included to demonstrate specific embodiments of the present invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited throughout the specification are expressly incorporated by reference in their entirety herein.

EXAMPLES

Example 1

Materials and Methods

Microarray and RT-PCR Analysis

Microarray analysis: NLRR-1 transcript was analyzed in tumor and normal tissues on Affymetrix microarrays as described by Tackels-Horne et al. (Tackels-Horne et al., 2001). RT-PCR anaylsis: Prostate tumors were obtained from Bio-Options (Fullerton, Calif.) and Ardais (Lexington, Mass.). Multiple Myeloma samples, consisting of CD138-purified cells using coated beads (Miltenyi Biotec Inc, Auburn, Calif.) were procured from Cureline (South San Francisco, Calif.). RNA was extracted using standard cesium chloride procedure followed by phenol chloroform extraction. Extracted RNA was reverse transcribed and quantified using the Taqman Gold kit (Applied Biosystems, Warrington, UK) and the following primers and probes: NLRR-1 forward: TCAATC CCACTAAATGAGCTGTA (SEQ ID NO: 2), reverse: GTCTGCAGAACCATCTTTGTCT (SEQ ID NO: 3), probe: CCACCACTCATTAACCTCTGGGAAGG (SEQ ID NO: 4); MUC1 forward: TGGCAGCAGCCTCTCTTA (SEQ ID NO: 5), reverse: CCCCTACAAGTTGGCAGAA (SEQ ID NO: 6), probe: CACAAACCCAGCAGTGGCAGC (SEQ ID NO: 7); RPL19 forward: GCGGATTCTCATG-GAACACA (SEQ ID NO: 8), reverse: GGTCAGCCAG-GAGCTTCTTG (SEQ ID NO: 9), probe: CACAAGCT-GAAGGCAGACAAGGCCC (SEQ ID NO: 10). All experiments were performed in duplicate. Human genomic DNA (BD Biosciences, San Jose, Calif.) was used as a standard to convert Ct (cycle threshold) to quantity and data were normalized to RPL19.

NLRR-1 Plasmid Constructions and Transfections

Figure 12A:
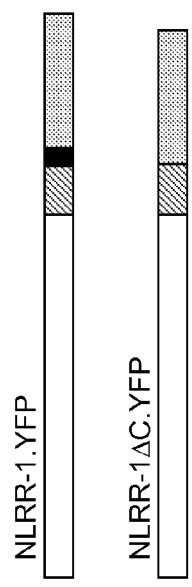
Figure 12B:
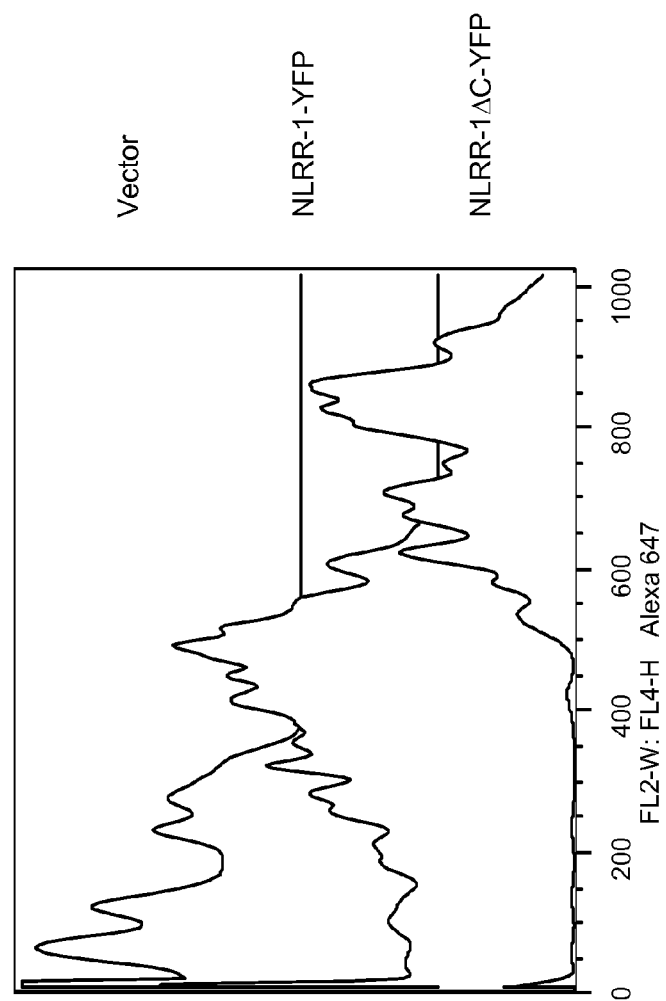

NLRR-1.ECD.HIS construct for CHO expression: The C-terminal His tagged extracellular domain of NLRR-1 protein was generated by standard cloning techniques and was transfected into CHO cells using Fugene 6 (Roche Diagnostics, Indianapolis, Ind.) per manufacturer's instructions. After 48 hr of transfection, high-expressing clones were selected in medium containing 200 nM methotrexate and without GHT. NLRR-1 protein was purified from the transfected CHO cell culture media by using Ni-NTA superflow column (Qiagen, Valencia, Calif.) for generation of monoclonal antibodies. NLRR-1.ECD.HIS construct for Baculovirus expression: The C-terminal His tagged extracellular domain of NLRR-1 was cloned into a modified pVL1393 (BD Pharmingen, San Jose, Calif.) baculovirus expression vector using standard cloning techniques and expressed in SF9 insect cells. Protein was purified on a Q Sepharose column for polyclonal antibody production in rabbits. NLRR-1.YFP and NLRR-1ΔC.YFP constructs: Full-length and ΔC YFP fusion constructs were generated by overlapping PCR cloning into the pEYFP-N1 vector (Clontech Laboratories, Mountain View, Calif.), which encodes an enhanced yellow-green fluorescent protein. HEK293 cells were transfected using Polyfect (Qiagen) per manufacturer's instructions and Cos-7 cells were serially transfected twice using Fugene 6 per manufacturer's instructions. NLRR-1ΔC was truncated at amino acid 681, deleting the clathrin-mediated endocytosis motif. (FIG. 12A-B).

Generation of NLRR-1 Antibodies and Flow Cytometry

The NLRR-1.ECD.HIS protein expressed and purified from Baculovirus was used to generate polyclonal antibody in rabbits (Invitrogen). Five Balb/c mice (Charles River Laboratories, Hollister, Calif.) were hyperimmunized with the Baculovirus or CHO expressed polyhistidine-tagged human extracellular NLRR-1 protein in Ribi adjuvant (Ribi Immunochem Research, Inc., Hamilton, Mo.) for generation of monoclonal antibodies. B-cells from these mice, all of which demonstrated high anti-NLRR antibody titers by direct ELISA and specific binding to NLRR expressed on transfected 293, DP-12 CHO and endogenously expressing LnCAP cells by flow cytometry, were fused with mouse myeloma cells (X63.Ag8.653; American Type Culture Collection, Rockville, Md.) using a modified protocol analogous to one previously described (Kohler and Milstein, 1975; Hongo et al., 1995). After 10-12 days, the supernatants were harvested and screened for antibody production by direct ELISA and flow cytometry. A total of eight positive clones, showing the highest immunobinding after the second round of subcloning by limiting dilution, were expanded and cultured for further characterization. The supernatants harvested from each hybridoma lineage were purified by affinity chromatography (Pharmacia fast protein liquid chromatography [FPLC]; Pharmacia, Uppsala, Sweden) using a modified protocol analogous to one previously described (Hongo et al., 1995). The purified antibody preparations were then sterile filtered (0.2-μm pore size; Nalgene, Rochester N.Y.) and stored at 4° C. in phosphate buffered saline (PBS).

Purified monoclonal antibodies were tested by flow cytometry on HEK293 cells transiently transfected with vector or NLRR-1.YFP constructs. Cells were stained with α-NLRR-1 monoclonal antibodies followed by α-mouse Ig-alexa 647 secondary for 30 minutes each on ice and analyzed on FACScan (BD Biosciences). Cells were gated on forward scatter (FSC), side scatter (SSC), propidium iodide (PI), and YFP and analyzed with Flowjo (Treestar, Ashland, Oreg.). (FIG. 14)

Cell Culture

Human tumor cell lines NCI-H2009, NCI-H647, NCI-H520, NCI-H1781, NCI-H226, and SK-MES-1 were maintained in RPMI1640 medium. HEK293 cells were maintained in F12:DMEM high glucose 50:50 medium. CHO DP12 cells were maintained in F12:DMEM 50:50 medium with GHT. Cos-7 cells were maintained in F12:DMEM 50:50 medium. All media were supplemented with 10% FBS, L-glutamine and penicillin-streptomycin.

Immunofluorescence

HEK293 cells transiently transfected with NLRR-1.YFP or NLRR-1ΔC.YFP were seeded onto 8 chamber glass slides. Cells were fixed in 4% paraformaldehyde for 20 minutes at room temperature. For NLRR-1 antibody staining, cells were permeabilized in 0.4% saponin buffer for 20 minutes at room temperature. Cells were then stained with α-NLRR-1 rabbit polyclonal antibody followed by α-rabbit-Cy-3 secondary. Slides were mounted with Vectashield mounting media with Dapi (Vector Lab, Burlingame, Calif.). Images were acquired using a 60× magnification on a microscope equipped with a camera. Image overlays were generated using Adobe Photoshop software.

Immunohistochemistry

Tissue microarrays were purchased from Cybrdi (Frederick, Md.). Antigen retrieval was performed by boiling in Borg Decloaker, Reveal, or Universal Reveal (Biocare Medical, Concord, Calif.). α-NLRR-1 polyclonal antibody and control rabbit Ig antibody was used at 6 ug/ml. Signal was detected using the MACH 3 system from Biocare Medical.

Co-Immunoprecipitation and Western Blot Analysis

Cells were lysed on ice for ten minutes in 0.5% NP40 in TBS with protease inhibitor cocktail (Roche, Basel, Switzerland) and PMSF. DNA was sheared through an 18 gauge needle and debris was removed by centrifugation. Lysates were pre-cleared with 10 μg/ml α-GP120 monoclonal antibody (Genentech, Inc) for 30 minutes at 4C with rotation. Pre-cleared lysates were incubated with α-NLRR-1 monoclonal antibody, α-EGFR (Cell Signaling, Danvers, Mass.), or α-ragweed (Genentech, Inc., South San Francisco, Calif.) antibodies at 10 μg/ml for 2 hours at 4C with rotation and precipitated with protein G agarose beads. Precipitates were washed 4 times in lysis buffer and resolved on a 4-12% Bis-Tris gel (Invitrogen, Carlsbad, Calif.). Proteins were transferred onto PVDF membrane (Invitrogen) and detected by Western analysis with α-NLRR-1 polyclonal at 1/500 (Genentech, Inc.), α-EGFR monoclonal antibody at 1/1000 (MBL Corporation, Woburn, Mass.), α-ERBB2 at 1/1000 (LabVision, Fremont, Calif.), α-Her3 at 1/1000 (Santa Cruz Biotechnology, Santa Cruz, Calif.), α-IGF1R at 1/1000 (Cell Signaling), and α-βadaptin at 1/500 (Santa Cruz Biotechnology).

Erk Phosphorylation (P-ERK) and AKT Phosphorylation (P-AKT) Assays

Cells were seeded in 60 mm plates at 75-85% confluency and allowed to recover overnight. Cells were starved in Optimem I (Invitrogen) for 6 to 8 hours before incubation with antibodies at 2 μg/ml in Optimem I overnight. Cells were stimulated with 10% serum, EGF, or TGFα at 37C and placed immediately on ice. A cell scraper was used to harvest the cells in phospho-buffer (1 mM sodium orthovanadate, 1 mM sodium azide, 1 μg/ml microcystin, 1 mM β-glycerol phosphate in PBS). Cells were fixed in 1% formaldehyde in phospho-buffer at 37 C for 10 minutes before permeabilization in ice cold 90% methanol for 20 minutes on ice. Cells were stained with P-ERK and P-AKT antibodies from Cell Signaling Technologies (Danvers, Mass.) as directed, followed by fluorescently conjugated secondary α-rabbit or α-mouse Ig. 5,000 to 10,000 events were collected for flow cytometry and gated on FSC and SSC. HEK293 and Cos-7 cells transfected with YFP constructs were starved overnight before stimulating, harvesting, and staining as above. 10,000 to 50,000 events were collected for flow cytometry and cells were gated on FSC, SSC, and YFP.

siRNA Knockdown of NLRR-1 and Assays

The NLRR-1 siRNA duplex was designed and synthesized by Dharmacon (Lafayette, Colo.). The sense sequence is GCCAGAACCUGAAAUUUACUU (SEQ ID NO: 11) and the antisense sequence is 5'-PGUAAAUUUCAGGUUCUG-GCUU (SEQ ID NO: 12). NCI-H2009, NCI-H647, NCI-H226, and SK-MES-1 cells were seeded at 2830/cm$^2$ and NCI-H520 and NCI-H1781 cells were seeded at 5660/cm$^2$. 100 nM of siRNA was transfected with DharmaFECT 4 for 6 to 8 hours before the transfectant was replaced with fresh media. A non-targeting siRNA sequence (Dharmacon) was used as a negative control. RT-PCR was performed on RNA extracted from 60 mm plates using RNeasy (Qiagen, Valencia, Calif.) per manufacturer's instructions. EGFR flow cytometry and immunoblot: After siRNA transfection for 24 hours, cells were harvested and stained with α-EGFR antibody conjugated to PE (BD Pharmingen) and propidium iodide for flow cytometry analysis. 10,000 events were collected and cells were gated on FSC, SSC, and PI. For immunoblot analysis, lysates were immunoblotted with α-EGFR (MBL) or α-βtubulin (Santa Cruz Biotechnology). Proliferation assay: siRNA knockdown was performed as described in 96 well plates. Cell growth was assessed after 4 days by Cell Titer Glo (Promega, Madison, Wis.) per manufacturer's instructions. Apoptosis and erlotinib synergy assay: siRNA transfection was performed as described in 60 mm plates. Cells were then seeded into 96 well plates at 1200/well. For erlotinib assay, cells were treated with erlotinib diluted in media containing 2 mg/ml BSA. For apoptosis assay with starvation, cells were starved in Optimem I. For both assays, cell viability was measured with Cell Titer Glo (Promega, Madison, Wis.) and apoptosis was measured with Caspase-Glo 3/7 (Promega) after 2 days. Data are graphed as mean±standard deviation (SD) or standard error (SE) as indicated on the figure legends.

Example 2

Figure 1A:
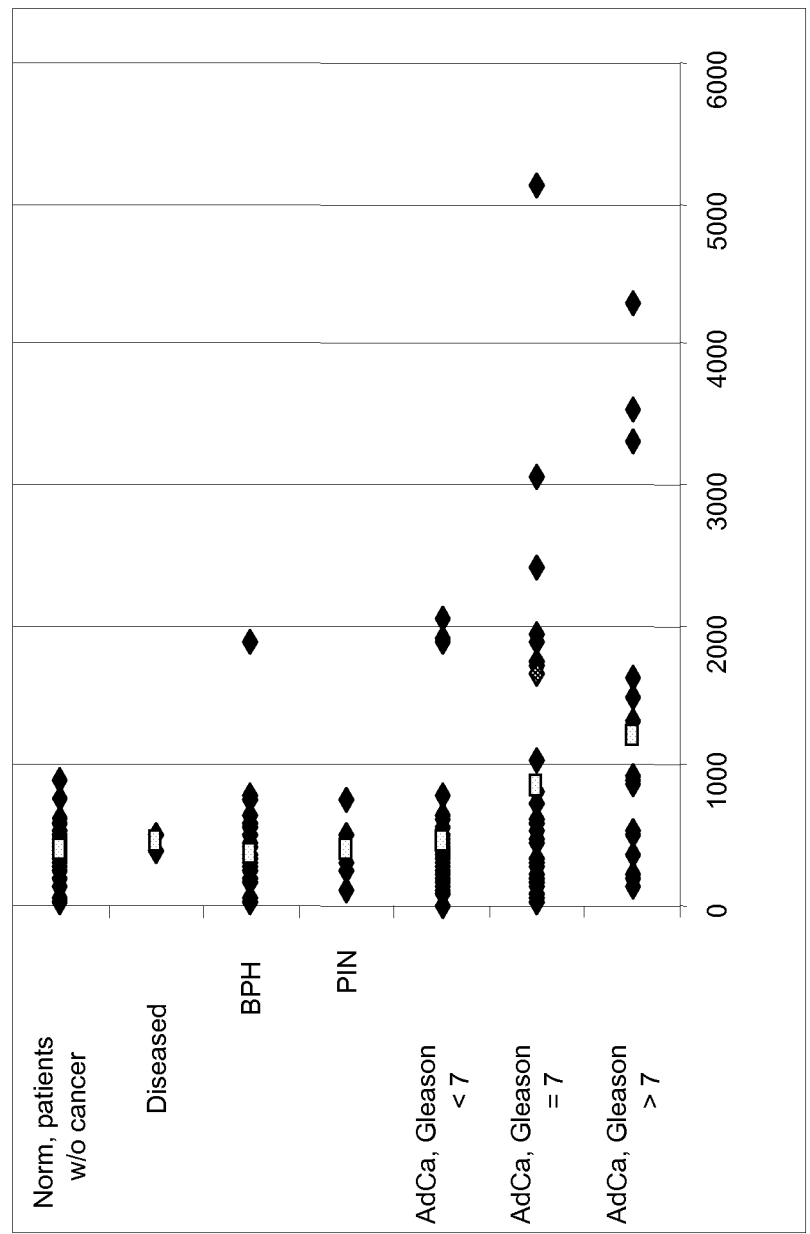
FIG. 1 shows NLRR-1 expression in high grade prostate cancer. 1A: NLRR-1 transcript levels in prostate cancers (diamonds) and mean expression (squares) as determined by microarray analysis. Norm, normal; BPH, benign prostatic hyperplasia; PIN, prostatic intraepithelial neoplasia; AdCa, adenocarcinoma. 1B: NLRR-1 transcript levels from laser capture microdissection of prostate tumors as determined by microarray analysis. 1C: RT-PCR analysis of MUC1 and NLRR-1 transcript in prostate tumors. Quantities were determined using a human genomic DNA standard curve.
Figure 1B:
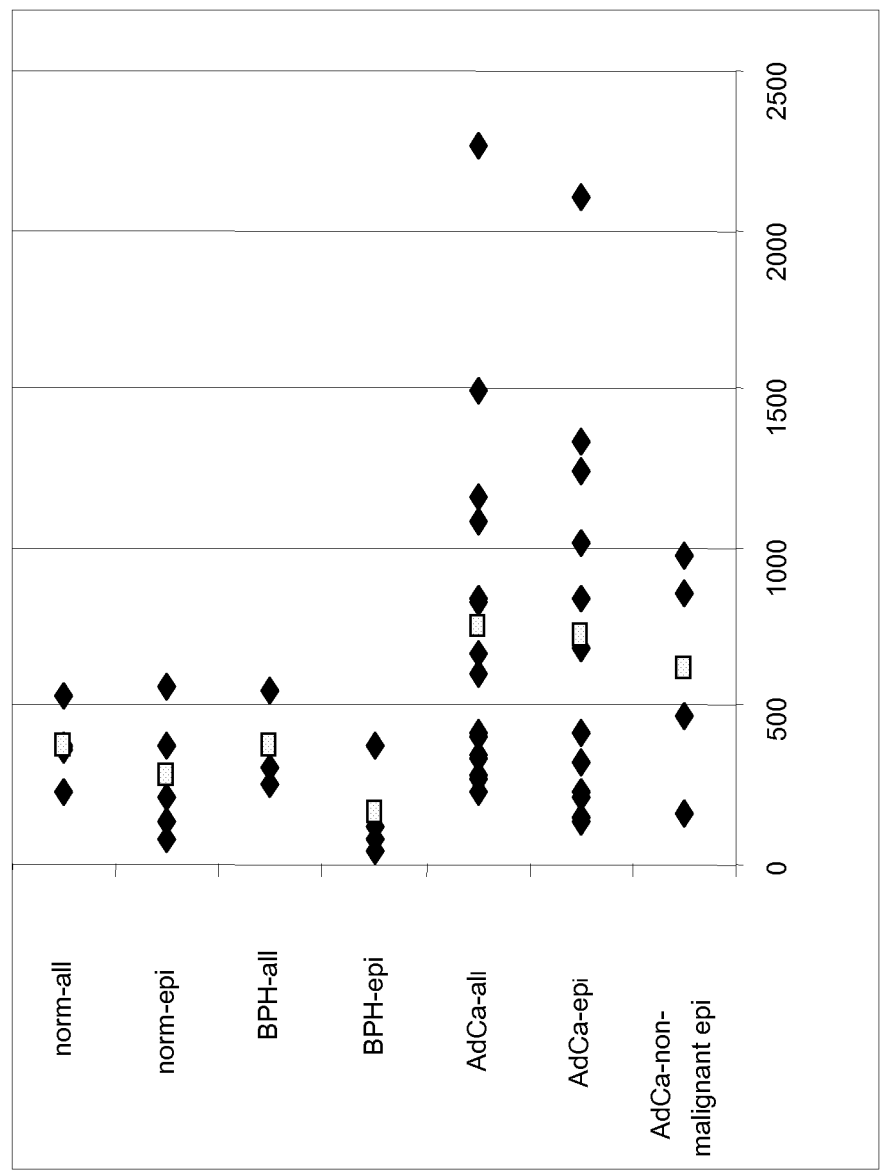
Figure 2A:
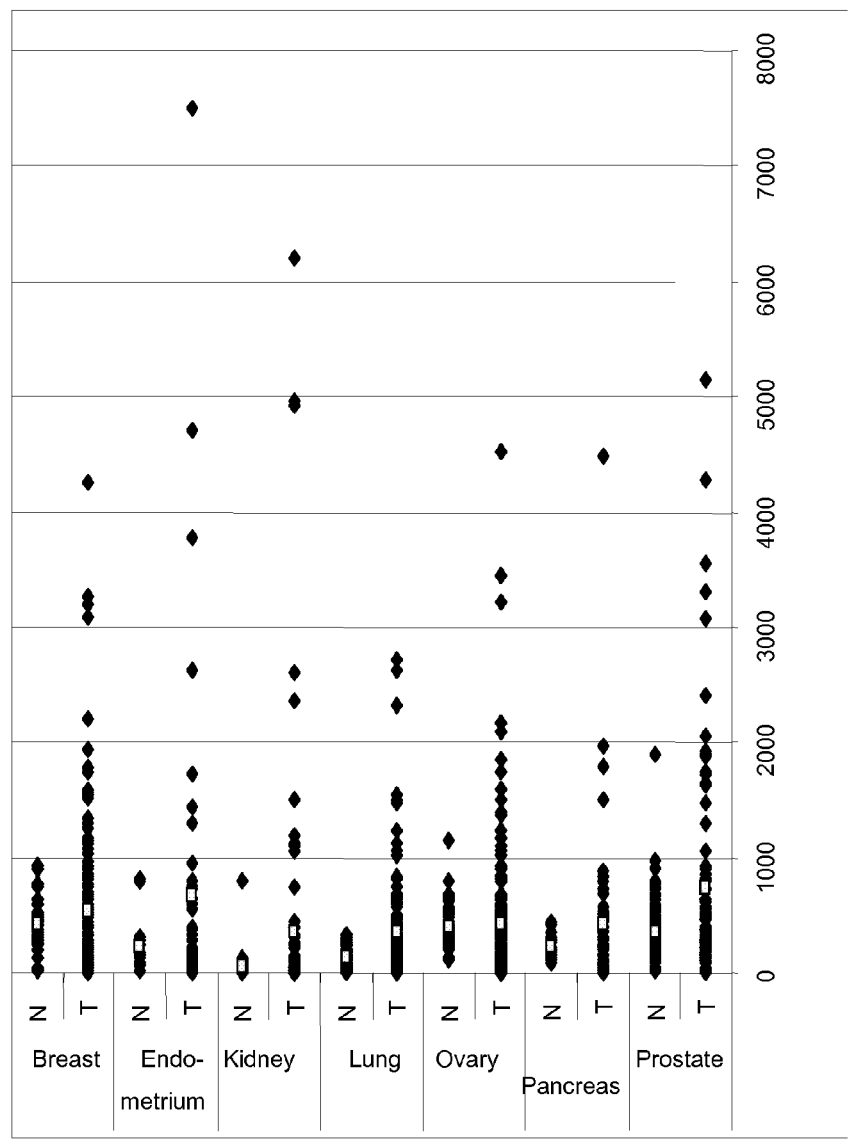
FIG. 2 shows NLRR-1 expression across a broad spectrum of cancers. 2A: NLRR-1 transcript in normal (N) vs. tumor (T) as determined by microarray analysis. 2B: NLRR-1 transcript expression in multiple myeloma and mantle cell lymphoma as determined by microarray analysis. 2C: ERBB2 vs. EGFR transcript in 2003 tumors as determined by microarray analysis. 2D: NLRR-1 vs. EGFR transcript in 2003 tumors as determined by microarray analysis.
Figure 2B:
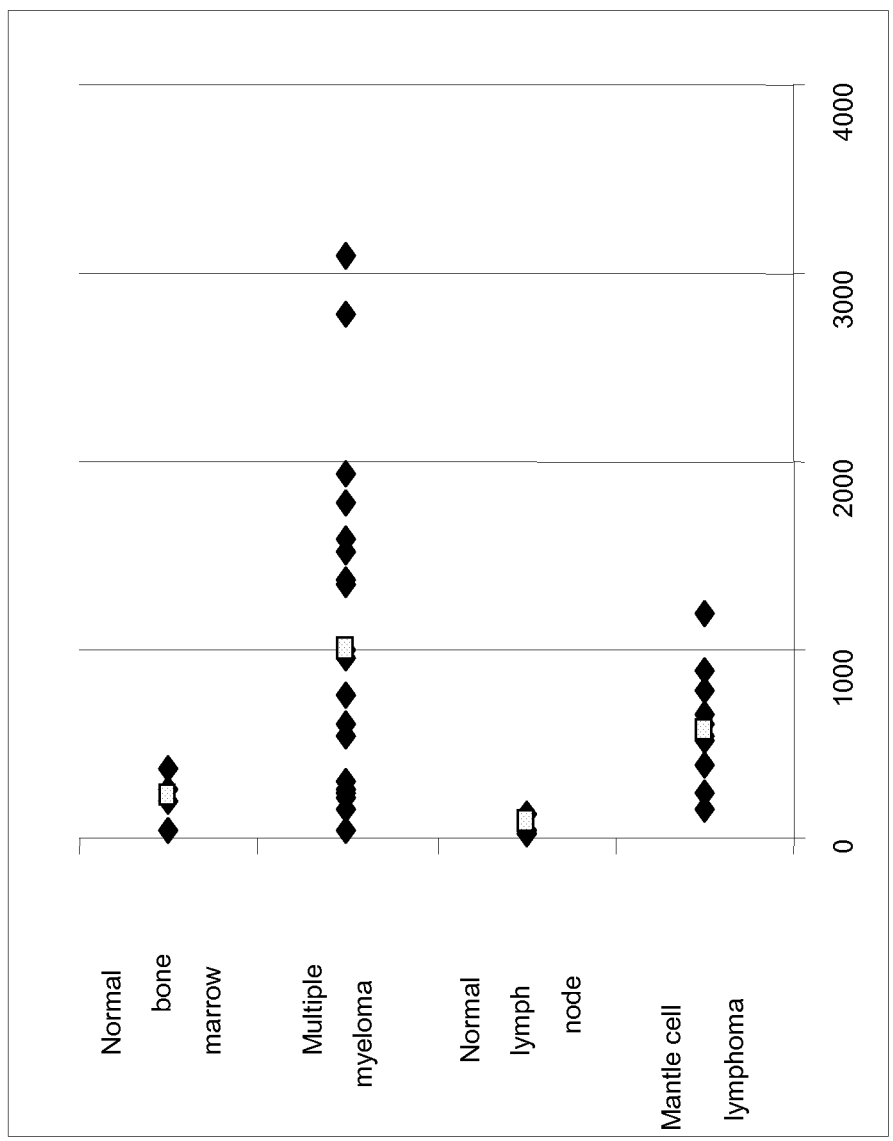

NLRR-1 is Expressed in Prostate Tumors and is Associated with High-Grade Disease NLRR-1 expression has been associated with early development and neuroblastoma (Aubert et al., 2003; Haines et al., 2005; Hamano et al., 2004). NLRR-1 was found to be expressed in prostate tumors, along with several other tumor types (FIG. 1A, B, FIG. 2A). Laser capture microdissection and expression profiling confirmed expression in prostate epithelium (FIG. 1B) and staining of prostate tumors with a polyclonal antibody specific to the extracellular domain of NLRR-1 revealed plasma membrane staining of prostate tumors.

Figure 1C:
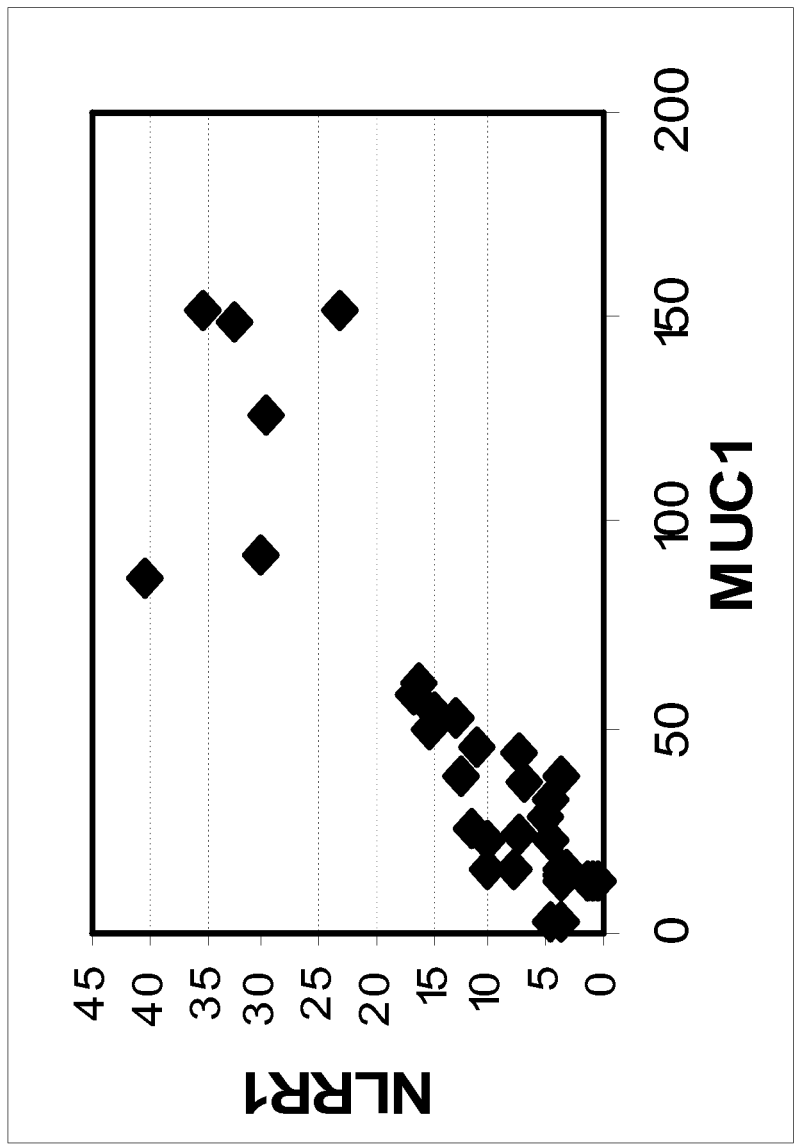

Expression of NLRR-1 in prostate tumors was particularly associated with high-grade disease, with higher transcript levels apparent in cases with Gleason score of 7 and above, and less transcript in cases of Gleason <7, prostatic intraepithelial neoplasia, and benign prostatic hyperplasia. Higher Gleason score is one clinical parameter associated with a poorer prognosis in prostate cancer (Andren et al., 2006b; Gleason and Mellinger, 1974). As an independent test of the association of NLRR-1 with high-grade disease and poor outcome, transcript quantification of MUC1 and NLRR-1 were performed using RT-PCR analysis of RNA isolated from prostate tumors (FIG. 1D). MUC1 has been associated with a greatly increased risk of death from prostate cancer, and with prostate cancer progression, independent of other clinical parameters (Andren et al., 2006b; Lapointe et al., 2004). The expression of MUC1 and NLRR-1 were highly correlated, with an $r^2$ of 0.93 (FIG. 1C), further supporting association of elevated NLRR-1 expression with high grade, poor outcome disease.

Example 3

Figure 9B:
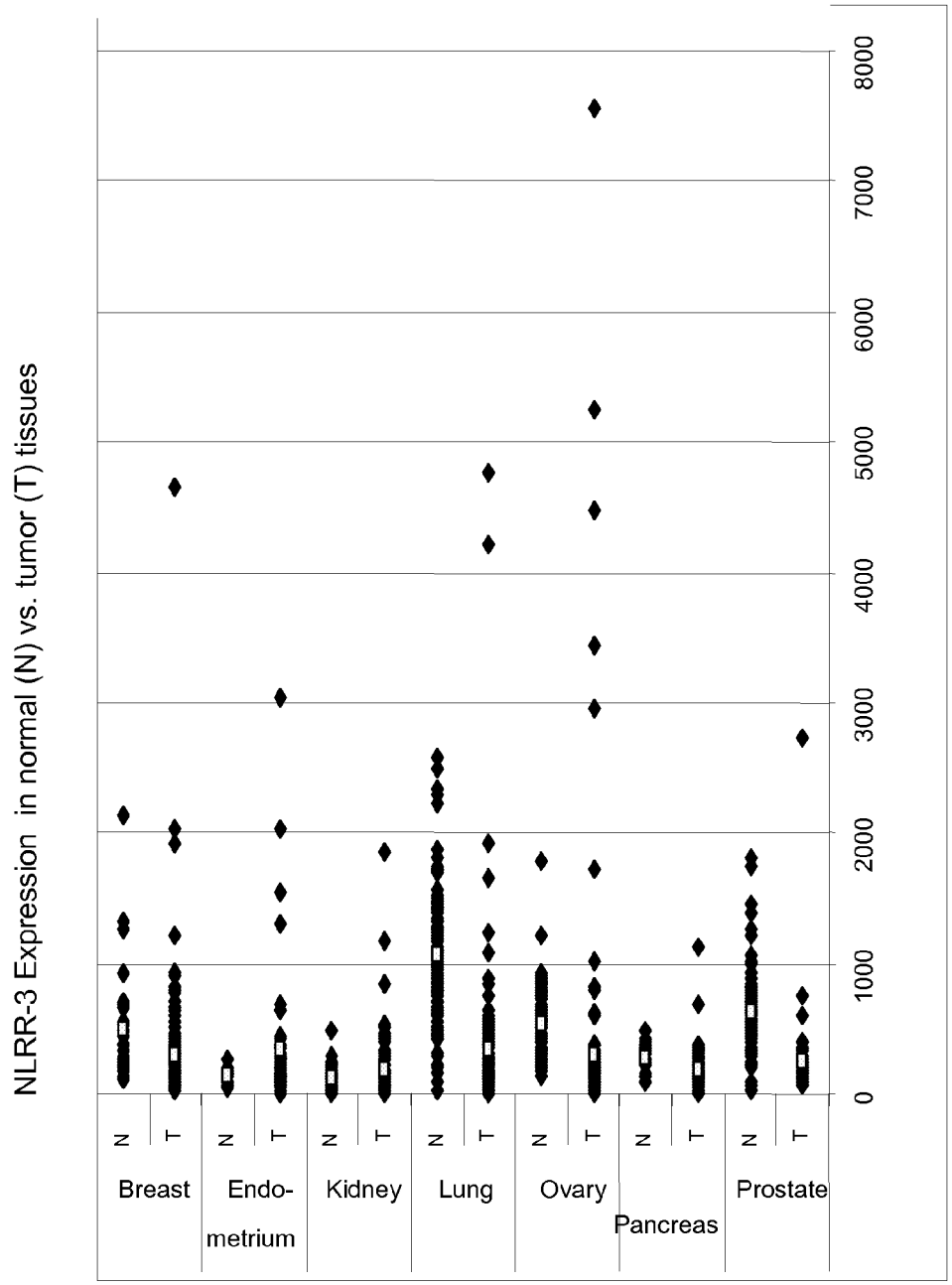

NLRR-1 is Expressed in Many Different Tumors and its Expression Anti-Correlates with Elevated EGFR Transcript analysis revealed NLRR-1 was expressed not only in prostate tumors but across a range of epithelial tumors, and even some aggressive hematological malignancies such as multiple myeloma and mantle cell lymphoma (FIG. 2A,B; FIG. 9A). In comparison, elevated NLRR-3 transcript was detected in a much smaller subset of tumor samples (FIG. 9B). Expression of NLRR-1 in the corresponding normal tissues was more restricted, with little or no transcript detected (FIG. 2A). Immunohistochemistry using an NLRR-1 polyclonal antibody confirmed protein expression in several of these different tumor types (pancreatic, breast, lung, and metastatic colon.

Figure 2C:
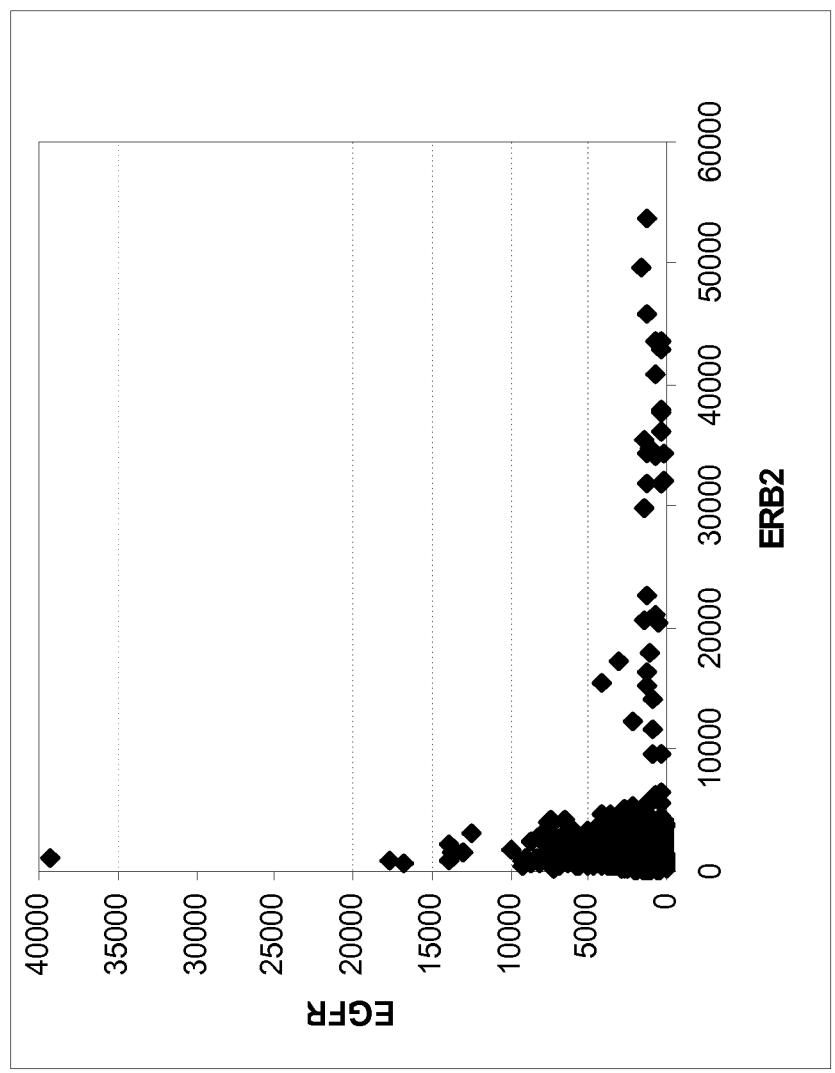
Figure 2D:
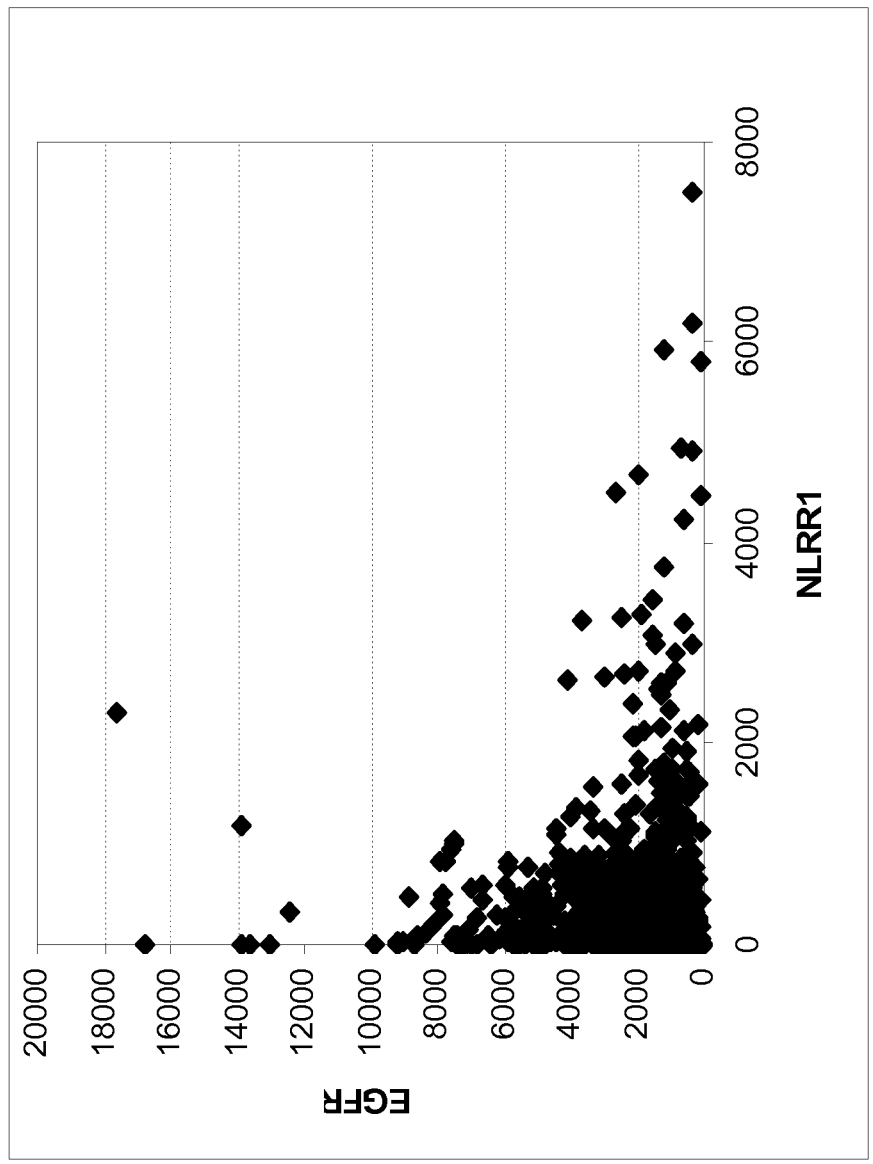
Figures 10A, 10B:
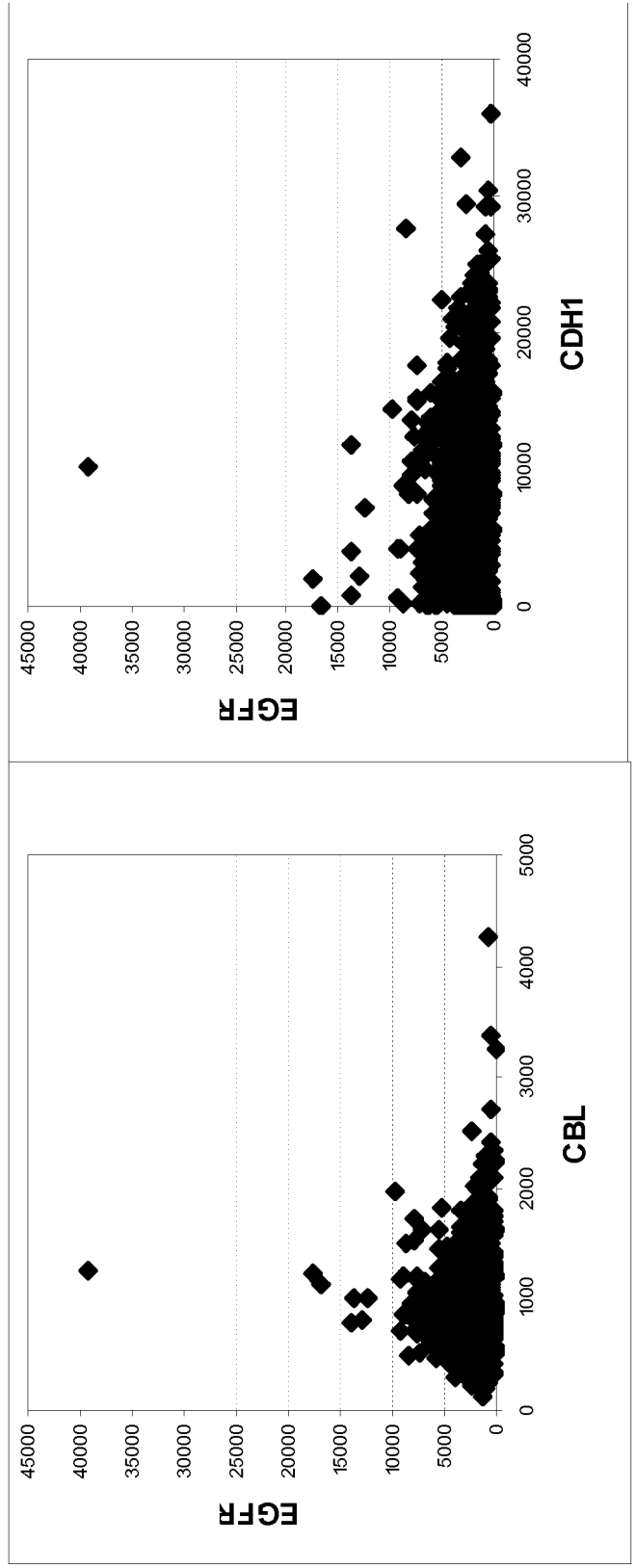

This data indicates that NLRR-1 facilitates EGFR pathway signaling and provides a means of increasing pathway activation without requiring amplification of EGFR. As elevated expression of one or other gene in tumors would suffice for pathway stimulation, a somewhat anti-correlated expression pattern across tumors might be expected. Such a pattern was observed, for example, for EGFR and ERBB2 (HER2) transcripts, due largely to ERBB2 amplification in a subset of breast tumors (FIG. 2C), and was also evident when comparing NLRR-1 and EGFR transcript data collectively across prostate, lung, breast, colon, pancreatic, kidney, stomach, endometrial and ovarian tumors (FIG. 2D). Most tumors expressing elevated levels of EGFR showed little or no NLRR-1 expression, and tumors with high NLRR-1 transcript levels had at best moderate, and generally low, levels of EGFR. Other proteins such as CBL and CDH1, which are associated with EGFR in a repressor capacity but not directly involved in forward signaling (Levkowitz et al., 1998; Qian et al., 2004), did not show this pattern of transcript anti-correlation in the same tumor data (FIG. 10A,B).

Example 4

NLRR-1 Physically Associates with EGFR and Promotes MAP Kinase Activation

Figure 3:
FIG. 3 shows co-immunoprecipitation of NLRR-1 and EGFR. 3A: BT549 cell lysates treated with α-NLRR-1, α-EGFR, or α-ragweed monoclonal antibody, precipitated with protein G agarose beads, and immunoblotted with α-NLRR-1 polyclonal or α-EGFR monoclonal antibody. 3B: NC1-H2009 cell lysates treated with α-NLRR-1 or α-ragweed monoclonal antibody, precipitated with protein G agarose beads, and immunoblotted with α-EGFR, α-ERBB2, α-ERBBr3, α-IGF1R, and α-βadaptin.

A possible physical interaction between NLRR-1 and EGFR was investigated by co-immunoprecipitation analysis. Anti-NLRR-1 or EGFR monoclonal antibodies were used to precipitate proteins from cell lines that endogenously express NLRR-1 and analyzed by immunoblot for presence of EGFR or NLRR-1. In breast tumor cell line BT549, treating cells with an anti-NLRR-1 monoclonal antibody effectively co-precipitated EGFR and in the reciprocal experiment, an anti-EGFR antibody was capable of precipitating NLRR-1 (FIG. 3A). Neither protein was precipitated when cells were treated under the same conditions with an antibody directed against an irrelevant protein (ragweed). This analysis was extended to lung tumor cell line NCI-H2009, which expresses higher levels of NLRR-1. Probing blots of lysates treated with an anti-NLRR-1 antibody with antibodies against NLRR-1, EGFR and ERBB2 all produced bands of the appropriate size, whereas no signal was detected for ERBB3 or a different receptor tyrosine kinase family member, IGF1R (FIG. 3B). These data suggest that NLRR-1 physically associates either directly with EGFR or indirectly via other components of the EGFR signaling complex. An association between NLRR-1 and the clathrin coat formation protein β-adaptin (AP2B1) would also be expected, due to the conserved clathrin-mediated endocytosis motif (Fukamachi et al., 2002), and this was also detected by co-immunoprecipitation in NCI-H2009 cells and immunoblot analysis (FIG. 3B).

Figure 4A:
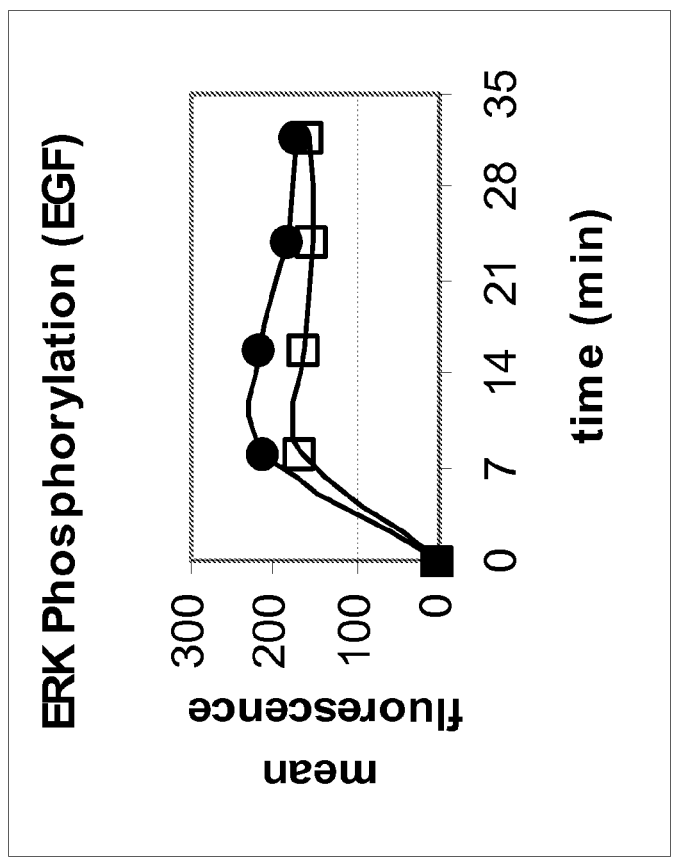
FIG. 4 shows ERK phosphorylation with NLRR-1 transfection. Cos-7 cells were transfected with pEYFP vector or NLRR-1.YFP, starved and stimulated with 100 ng/ml EGF (4A) or 50 nM TGFα (4B), then analyzed by flow cytometry for P-ERK. 50,000 events were collected and gated on FSC, SSC, and YFP. Vector (●); NLRR-1-YFP (□).
Figure 4B:
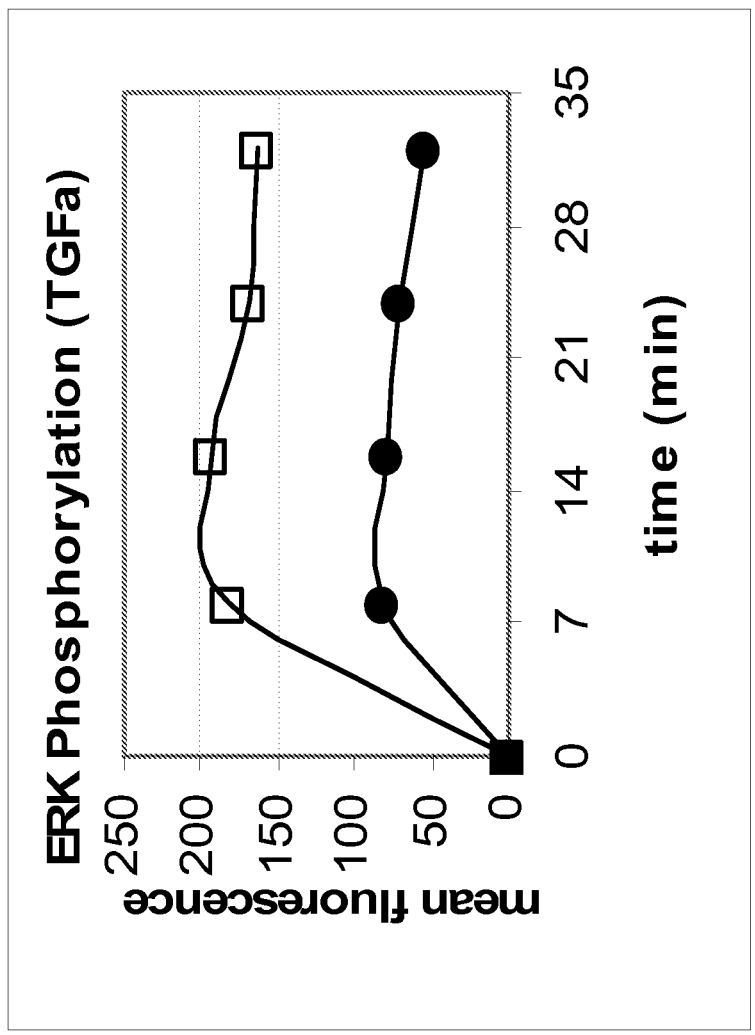

A role for NLRR-1 in promoting MAP kinase signaling was investigated using C-terminal YFP tagged NLRR-1. Transfected cells were gated for YFP-expressing cells and subjected to quantitative flow cytometry analysis for phosphorylated ERK upon stimulation with either EGF or TGFα (see FIG. 11A,B for additional data on this methodology). No enhancement of signaling was detected upon EGF stimulation in Cos-7 cells (FIG. 4A). However, stimulation using TGFα produced a significant increase in the magnitude of MAP kinase activation in cells transfected with NLRR-1 as compared to vector-transfected controls (FIG. 4B). These findings suggest that NLRR-1 serves as a facilitator of TGFα mediated EGFR signaling.

Figure 5A:
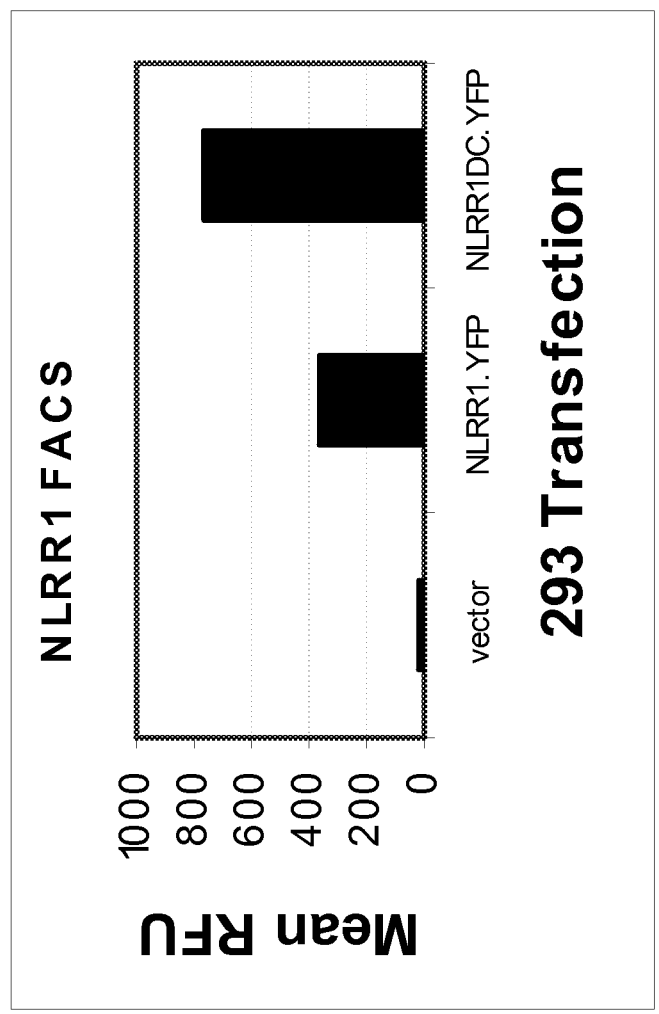
FIG. 5 shows NLRR1 and EGFR cell surface expression. 5A: Detection of NLRR-1 by flow cytometry of NLRR-1 transfected cells. HEK293 cells were transiently transfected with pEYFP vector, NLRR-1.YFP, or NLRR-1ΔC.YFP and stained with monoclonal antibody followed by α-mouse Ig-alexa 647 secondary. NLRR-1ΔC is truncated at amino acid 681, deleting the clathrin-mediated endocytosis motif 10,000 events were collected and cells were gated on FSC, SSC, PI, and YFP. Data represent mean relative fluorescence units. 5B: Detection of EGFR by flow cytometry following NLRR-1 siRNA knockdown. 10,000 events were collected and gated on FSC, SSC, and PI. Median fluorescence units are graphed.
Figure 5B:
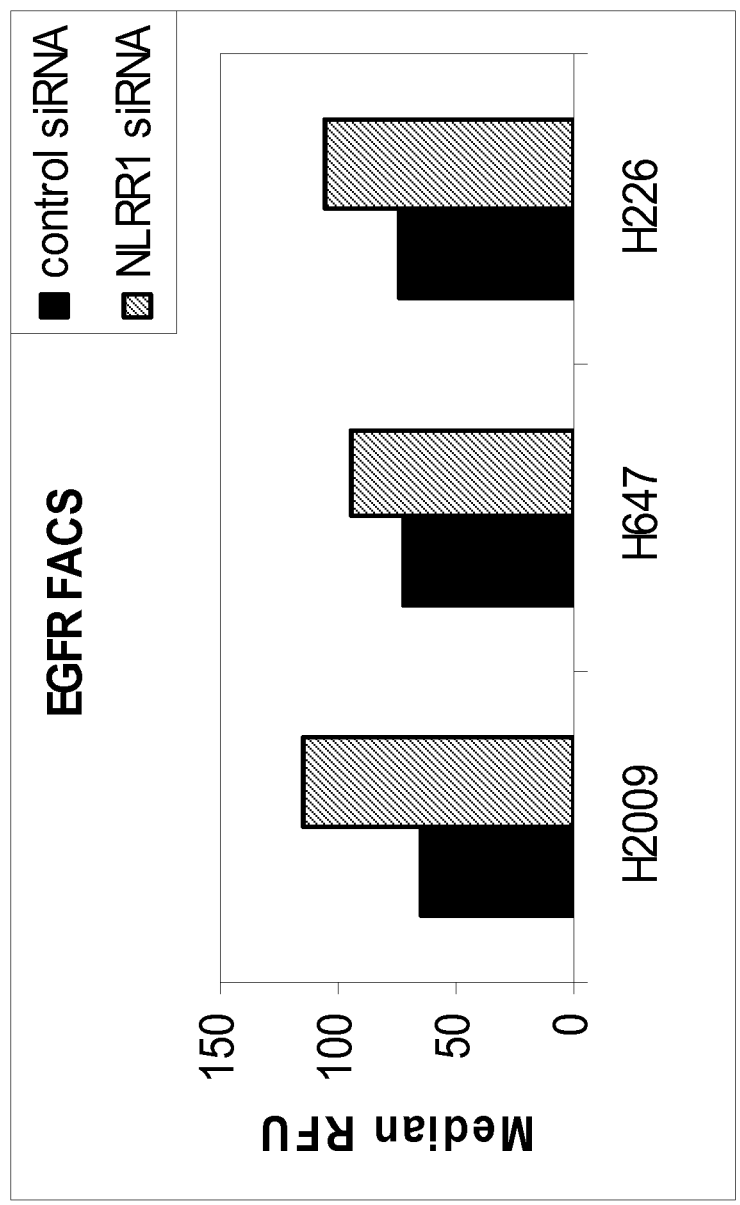

NLRR-1 shares significant sequence homology with NLRR-3, including complete conservation of the C-terminal region containing the clathrin-mediated endocytosis motif that in NLRR-3 is responsible for facilitating signaling in response to low concentrations of EGF, presumably by promoting clustering of signaling components at the cell membrane, and signaling of the internalized complex. Flow cytometry of YFP-tagged deletion constructs transfected into normal cells indicated that the endocytosis motif in NLRR-1 also serves to promote internalization of NLRR-1 (FIG. 5A), although NLRR-1 was still internalized without this motif. To more directly address the effects of NLRR-1 expression on EGFR internalization in tumor cells, NLRR-1 was depleted using siRNA knockdown in endogenously-expressing tumor cell lines (FIG. 6A), and surface EGFR protein levels analyzed by flow cytometry and compared to a non-targeting siRNA control (FIG. 5B). In 3 tumor cell lines with sufficient EGFR for quantitative flow cytometry (NCI-H2009, NCI-H226, NCI-H647), an increase in surface EGFR was detected in the NLRR-1 depleted cells, the magnitude of which was greatest in cells which expressed the highest endogenous level of NLRR-1 (NCI-H2009, FIG. 6A; FIG. 5B). These data support a role for NLRR-1 in promoting uptake of the EGFR signaling complex. The levels of total EGFR protein were unchanged in NLRR-1 depleted and control-depleted cells, indicating that the decreased surface expression was not a result of increased degradation.

Example 5

Figure 6A:
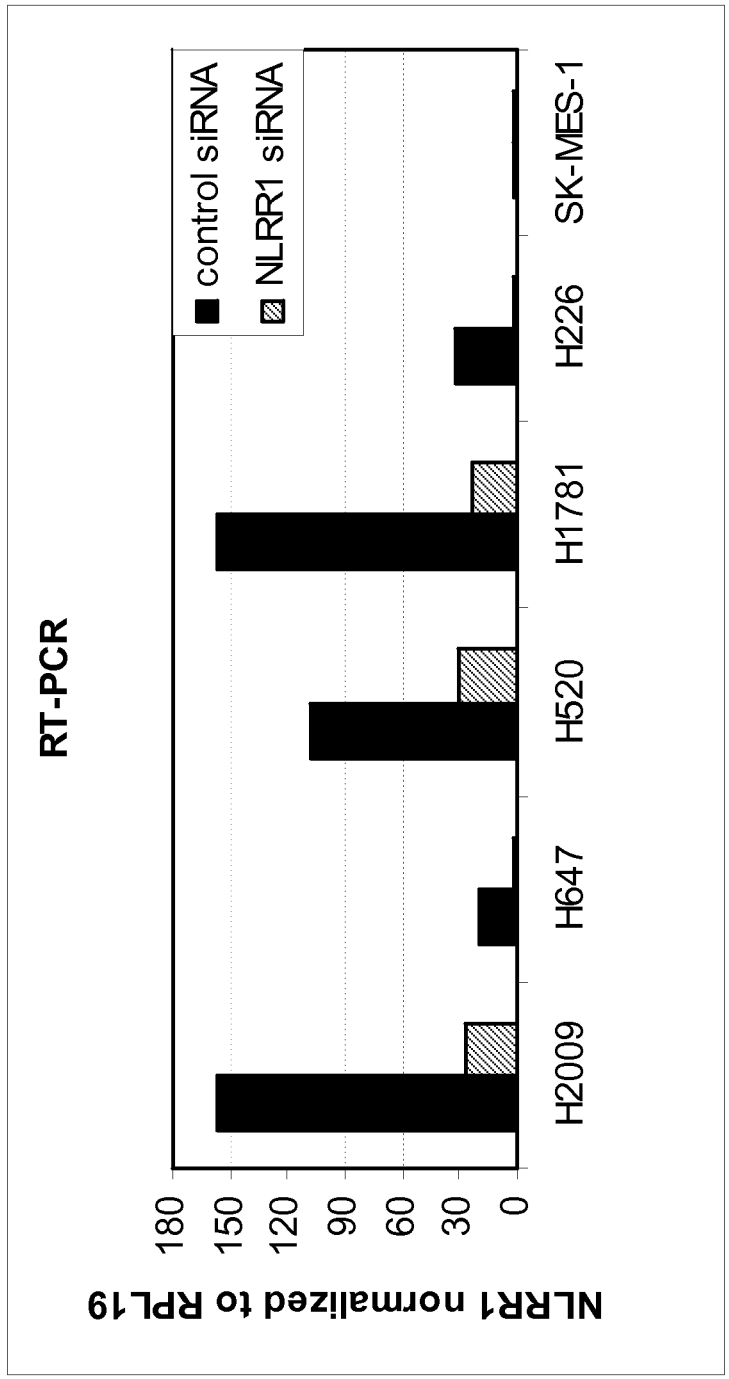
FIG. 6 shows siRNA knockdown of NLRR-1 in tumor cell lines. 6A: NLRR-1 transcript analysis using RT-PCR on control and NLRR-1 siRNA knockdowns in tumor cell lines. Data are normalized using RPL19 expression. 6B: Cell viability defect in tumor cell lines with NLRR-1 siRNA knockdown graphed as a percentage of control. Data represent mean of triplicates±SD. 6C: Apoptosis induced by starvation in tumor cell lines with NLRR-1 siRNA knockdown. Apoptosis was measured by caspase 3/7 activity and normalized for viable cells on matched replicates. Data represent mean of triplicates±SD.
Figure 6B:
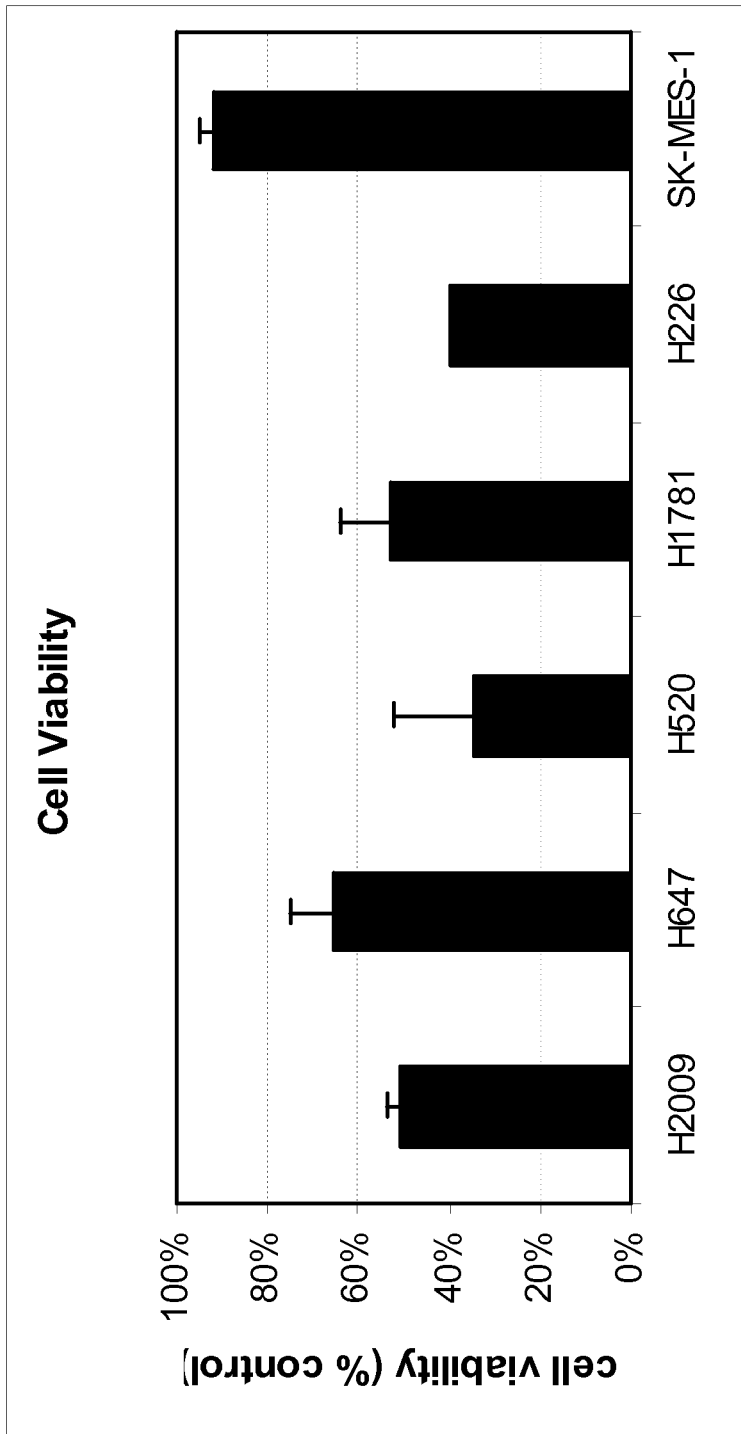

NLRR-1 is Important for Cell Viability and Resistance to Apoptosis in Endogenously-Expressing Tumor Cell Lines The role of NLRR-1 in tumor cells was further investigated using a panel of 5 non-small cell lung carcinoma cell lines in which NLRR-1 was endogenously expressed at various transcript levels (NCI-H2009, NCI-H520, NCI-H647, NCI-H1781, NCI-H226; FIG. 6A). Knockdown of NLRR-1 using siRNA resulted in similar proliferation defects in all these lines as compared to a control non-targeting siRNA, when analyzed using an ATP-based quantitative cell viability assay (FIG. 6A, B). By contrast, no significant defect in proliferation was observed with the NLRR-1 siRNA knockdown in SK-MES1, a lung carcinoma cell line that did not express NLRR-1 (FIG. 6A,B).

Figure 6C:
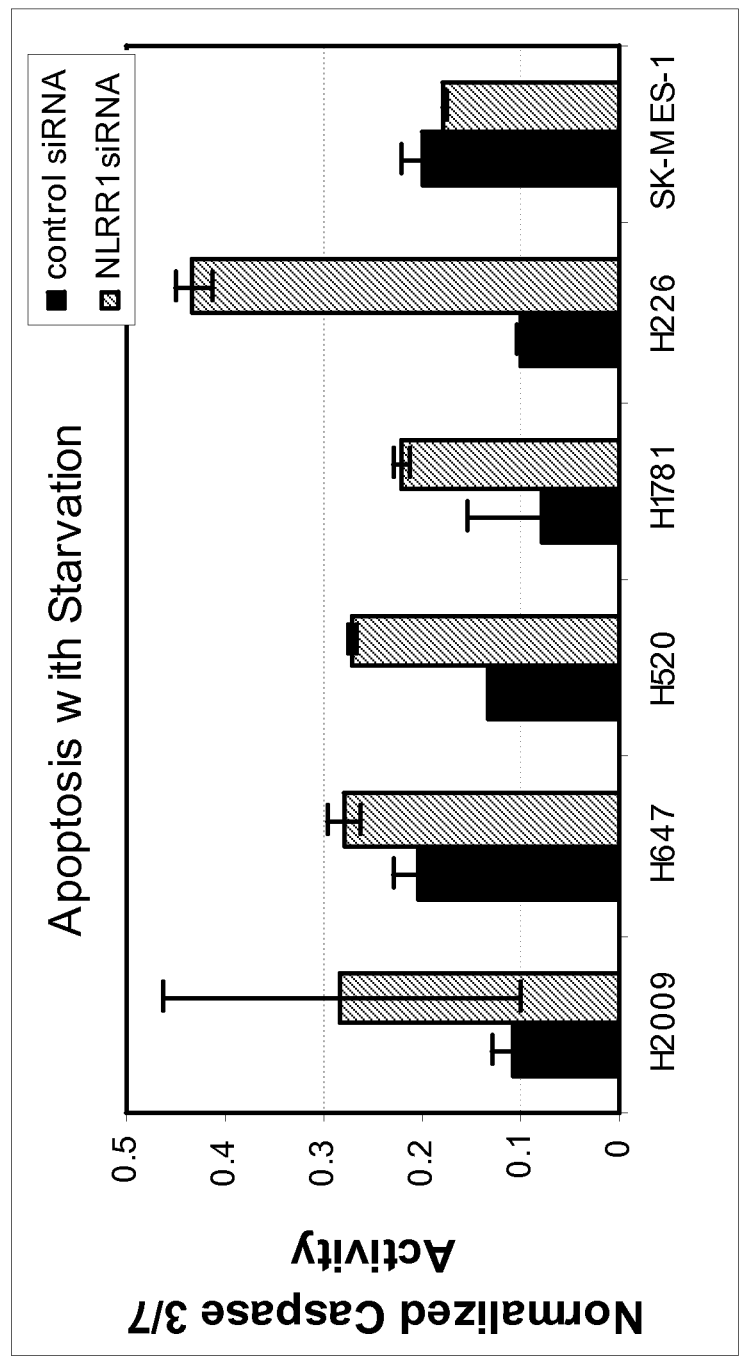

EGFR pathway activation in tumor cells has consequences for many important cellular processes, including cell survival. EGFR signaling occurs both at the cell surface and from the internalized complex, and endosome-associated EGFR signaling has been implicated in the stimulation of signal transduction pathways leading to cell survival (Wang et al., 2002). Given a possible role for NLRR-1 in promoting clustering and internalization of the EGFR signaling complex, the viability defect observed with the NLRR-1 knockdown was further investigated to determine if the apparent reduction in viability resulted from reduced growth only, or if apoptotic cell death was playing a role. NLRR-1 was knocked down using siRNA, cells were subjected to starvation to promote apoptosis, and apoptosis was measured by caspase 3/7 activity and normalized for viable cells (FIG. 6C). All cell lines that endogenously expressed NLRR-1 showed an increase in apoptosis upon knockdown of NLRR-1 as compared to a non-targeting control RNA. These data indicate that NLRR-1 is important for viability in these endogenously expressing tumor cell lines, and contributes to the resistance of apoptotic cell death.

Example 6

Figures 7A, 7B:
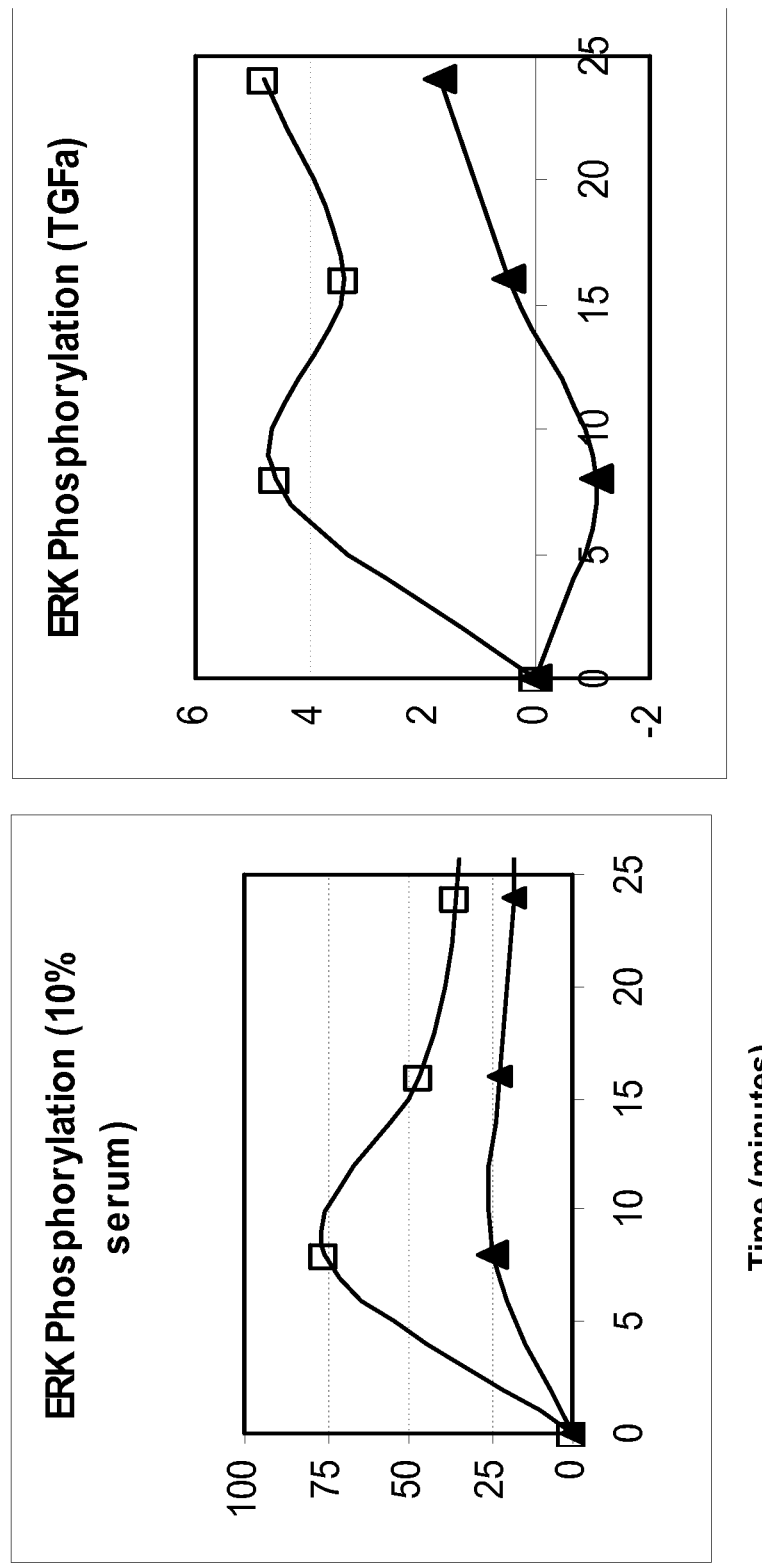
FIG. 7 shows ERK and AKT phosphorylation. 7A-E: ERK phosphorylation measured by flow cytometry. Cells were starved and treated with either α-ragweed or α-NLRR-1 monoclonal antibody and then stimulated for a time course with A: 10% serum B: 50 nM TGFα C: 100 ng/ml EGF D: 1 ng/ml EGF E: 0.01 ng/ml EGF. α-ragweed (□); α-NLRR-1 (▲). 7F-I: AKT phosphorylation measured by flow cytometry. Cells were starved and treated with either α-ragweed or α-NLRR-1 monoclonal antibody and then stimulated for a time course with F: 10% serum G: 50 nM TGFα H: 1 ng/ml EGF I: 0.01 ng/ml EGF. α-ragweed (□); α-NLRR-1 (▲). 7J-K: ERK phosphorylation following 50 nM TGFα stimulation comparing α-ragweed monoclonal antibody, α-NLRR-1 monoclonal antibody, and erlotinib at 2.5 μM and 0.25 μM J: time course K: at 16 minutes graphed as a percentage of α-ragweed control. α-ragweed (□); α-NLRR-1 (▲); Erlotinib 2.5 μM (●); Erlotinib 0.25 μM (x). For flow cytometry, 5,000 to 10,000 events were collected and gated on FSC and SSC.
Figure 11C:
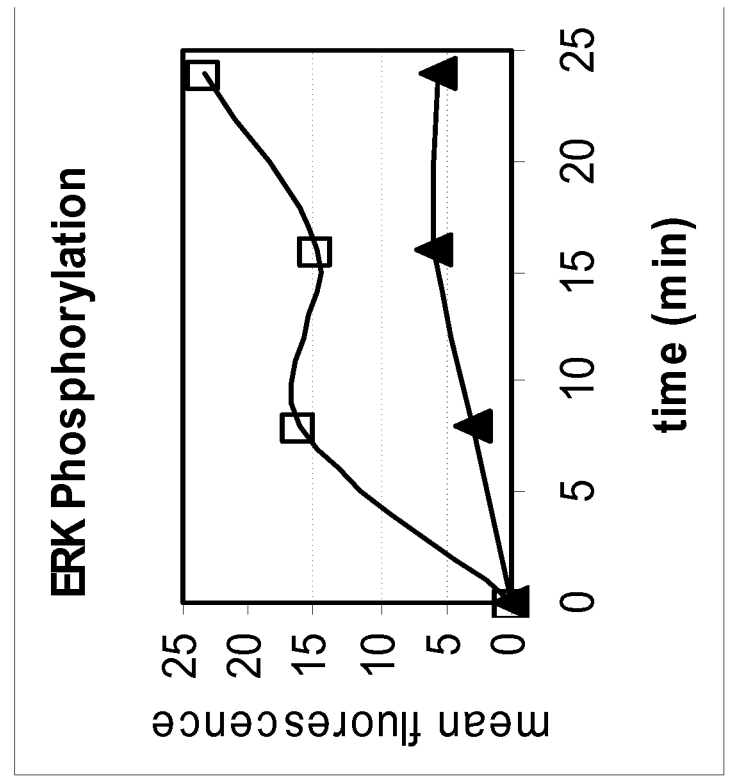
Figure 11B:
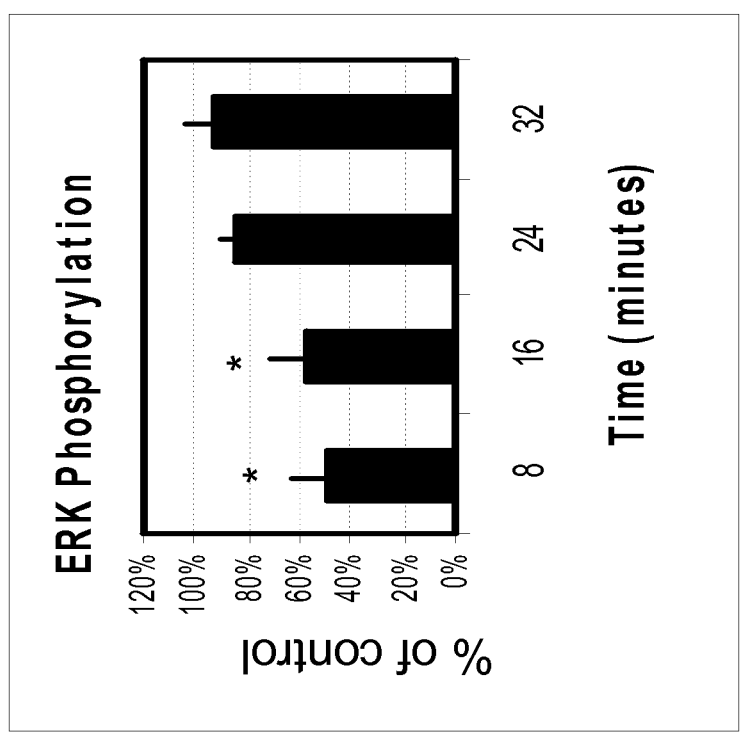

An Anti-NLRR-1 Monoclonal Antibody Attenuates MAP Kinase and P13 Kinase Activation in Tumor Cells As demonstrated herein, NLRR-1 promotes MAP kinase pathway activation, as assessed by phosphorylation of ERK, when transfected into normal cells. To investigate whether NLRR-1 plays a similar role in tumor cells, the lung carcinoma cell line NCI-H2009 was treated with antibodies, stimulated with serum, EGF, or TGFα, and phosphorylation of ERK was assessed quantitatively across a 25 minute interval using flow cytometry. Anti-NLRR-1 monoclonal antibody 3D1 was capable of significantly reducing the magnitude of ERK phosphorylation in response to both serum and TGFα (FIG. 7A, B; FIG. 11) as compared to a control antibody directed against an irrelevant protein (Ragweed). In an assessment of assay robustness, analysis of serum-stimulated cells across several independently conducted assays indicated that the attenuation of ERK phosphorylation was reproducible (FIG. 11B) and also apparent in a different NLRR1-positive cell line, NCI-H520 (FIG. 11C). These data indicate that NLRR-1 could play an important role in MAP kinase pathway activation in response to TGFα and serum stimulation.

Figures 7C, 7D:
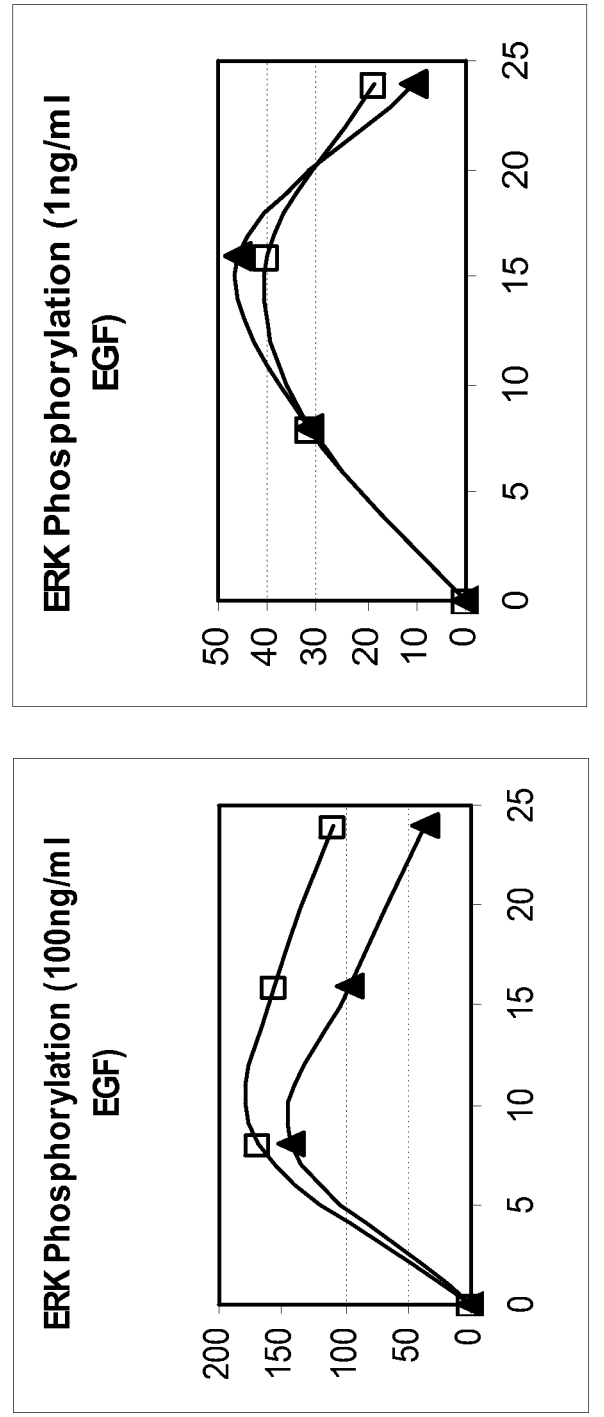
Figure 7F:
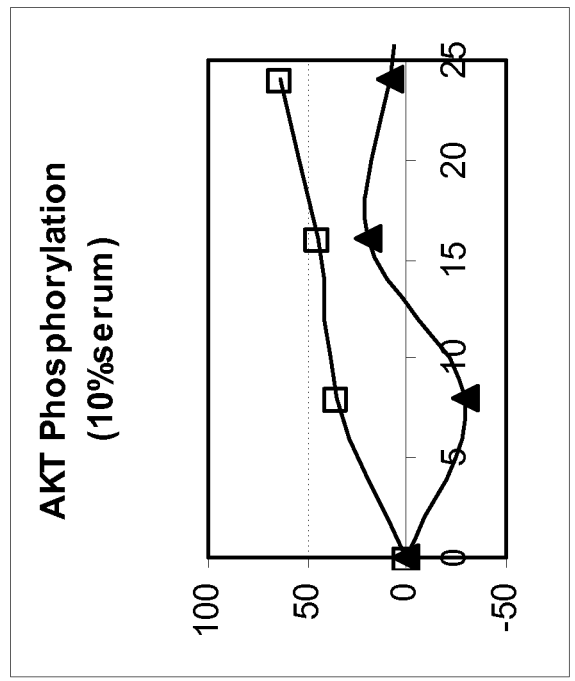
Figure 7E:
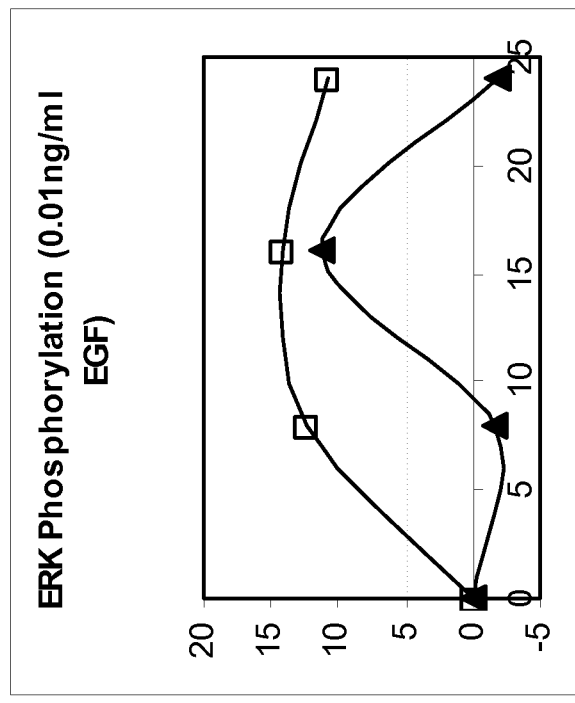

Consistent with the lack of effect seen on ERK activation using EGF in normal cells transfected with NLRR-1, the 3D1 antibody had little or no effect on EGF-mediated signaling in NCI-H2009 at concentrations of 100 ng/ml and 1 ng/ml EGF (FIG. 7C, D). Evidence of delayed and reduced magnitude of ERK activation was only apparent at low EGF concentration (0.1 ng/ml; FIG. 7E). These data suggest that any role NLRR-1 might play in promoting MAP kinase activation in response to EGF is only relevant at low concentrations of EGF. It is possible that this result may nonetheless be physiologically relevant for tumor cells in growth factor-limiting environments in the host, and these data are also consistent with the increased pathway activation promoted by homolog NLRR-3, which was observed at only very low concentrations of EGF (Fukamachi et al., 2002).

Figure 7H:
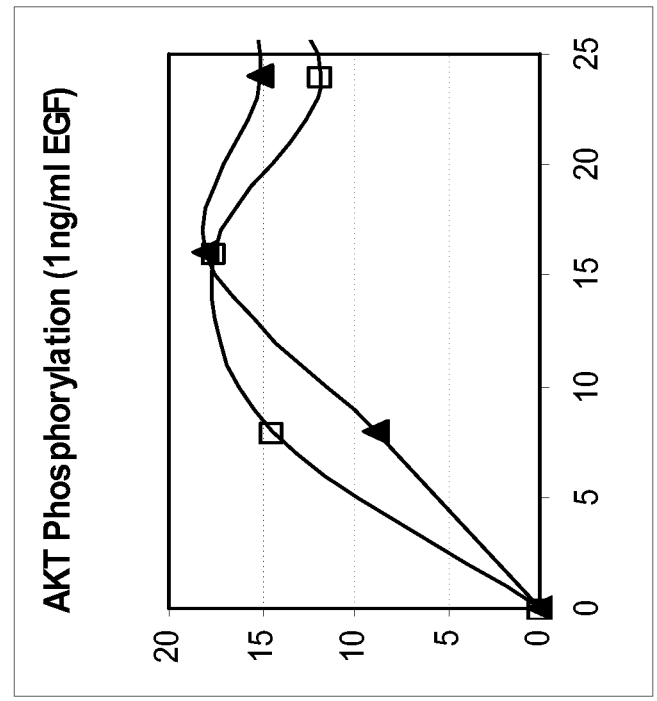
Figure 7G:
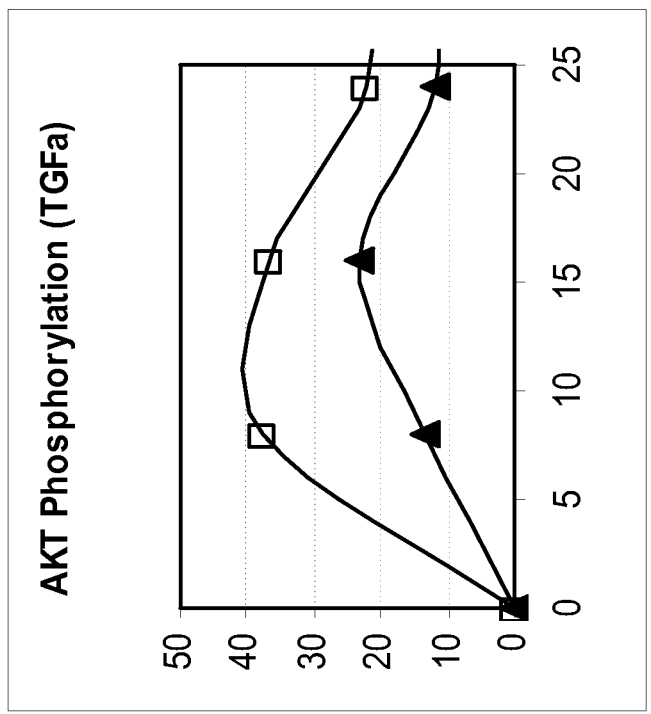

EGFR activation also results in signaling through the PI3 kinase pathway, which can trigger a cascade of responses affecting cell growth, proliferation, survival and motility, that contribute to driving tumor progression (Hennessy et al., 2005; Vivanco and Sawyers, 2002). A possible role for NLRR-1 in promoting PI3 kinase pathway signaling in tumor cells was thus also investigated using the anti-NLRR-1 monoclonal antibody 3D1 and quantitative flow cytometry of phosphorylated AKT upon treatment with 10% serum, TGFa, and EGF. Concordant with the observations for MAP kinase activation, 3D1 reduced the magnitude of AKT phosphorylation in response to stimulation with TGFα or 10% serum (FIG. 7F, G). Again, little blocking effect was seen with EGF stimulation (FIG. 7H) and some evidence of possible inhibition of phosphorylation was detected only at a very low concentration of EGF (0.01 ng/ml, FIG. 7I).

Figures 7I, 7J:
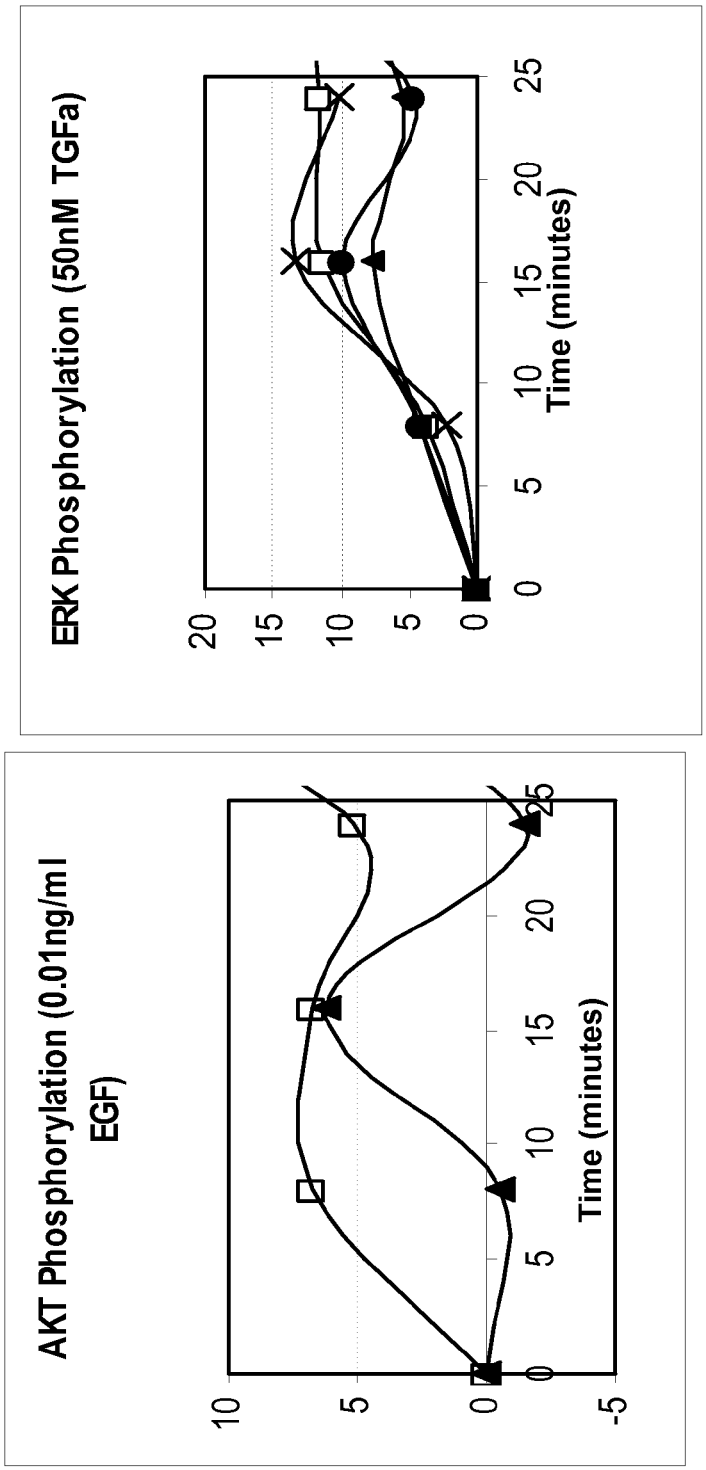
Figure 7K:
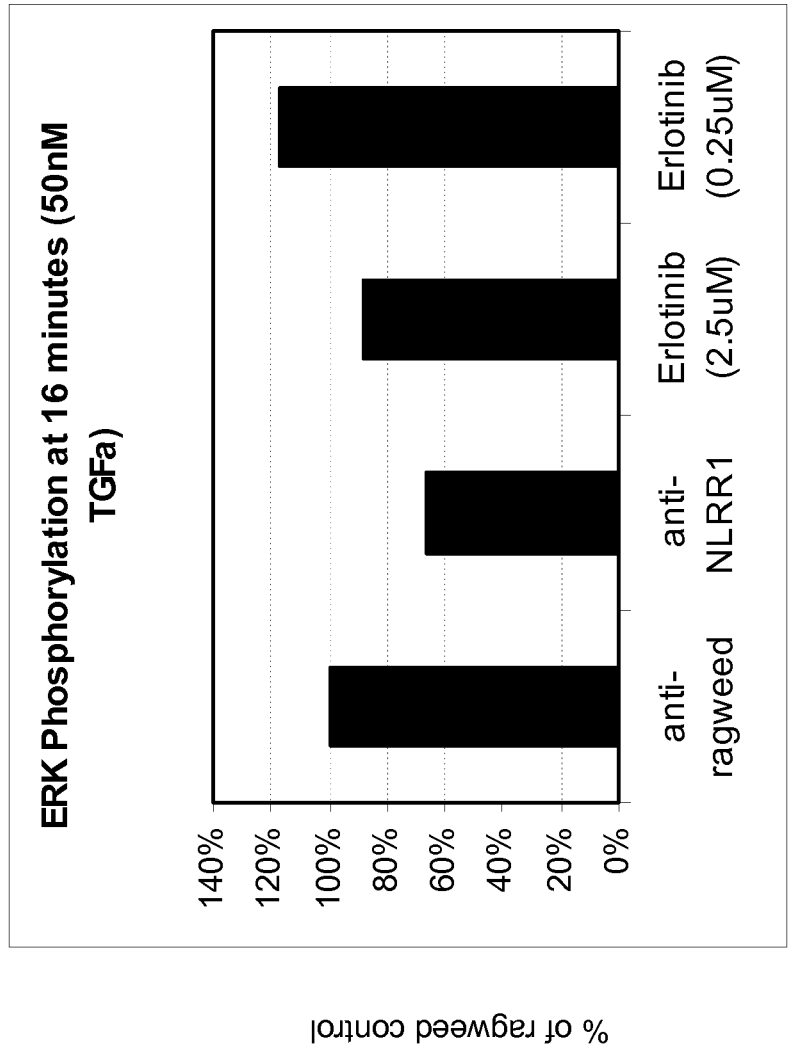

The attenuation of MAP kinase activation observed with the anti NLRR-1 antibody 3D1 was directly compared with that generated by a selective EGFR inhibitor, erlotinib ("Tarceva"). NCI-H2009 cells have been characterized as sensitive to erlotinib, with an $IC_{50}$ of less than or equal to 2 uM (Yauch et al., 2005). NCI-H2009 cells were stimulated with TGFα in the presence of 3D1, a control antibody directed against an irrelevant protein (ragweed) and 0.25 uM or 2.5 uM erlotinib. The 3D1 antibody was capable of attenuating MAP kinase phosphorylation at least as well as 2.5 uM erlotinib (FIG. 7J, K). As targeting NLRR-1 with an antibody produced a similar effect to targeting EGFR directly with a selective kinase inhibitor, these data indicate that NLRR-1 expression is important for pathway activation in this endogenously expressing cell line. The attenuation of MAP kinase activation in NCI-H520 with an NLRR-1 monoclonal antibody (FIG. 11C) indicates that this is also true for an erlotinib-resistant cell line (Yauch et al., 2005).

Example 7

Depletion of NLRR-1 in Lung Tumor Cell Lines Promotes Apoptosis Upon Treatment With the EGFR Inhibitor Erlotinib One contribution of EGFR signaling to tumor cell malignancy is the promotion of cell survival, and selective EGFR inhibitors have been shown to increase apoptosis in tumor cells (Chinnaiyan et al., 2005; Moyer et al., 1997; Ng et al., 2002; Sordella et al., 2004). In colon tumor cells, targeting of both EGFR and ERBB2 with small molecule inhibitors resulted in a synergistic increase in apoptosis (Zhou and Brattain, 2005). Several of the lung tumor cell lines used in this study, which endogenously express NLRR-1, have been classified as resistant to erlotinib, with IC50s of 8 uM or greater (Yauch et al., 2005). Erlotinib has been demonstrated to enhance apoptosis in tumor cells in combination therapy (Chinnaiyan et al., 2005; Ng et al., 2002). As knockdown of NLRR-1 in endogenously expressing tumor cell lines results in increased apoptosis, a study was conducted to determine if changes in sensitivity to apoptosis in the presence of erlotinib might be observed with knockdown of NLRR-1 in these otherwise resistant cell lines.

Figure 8B:
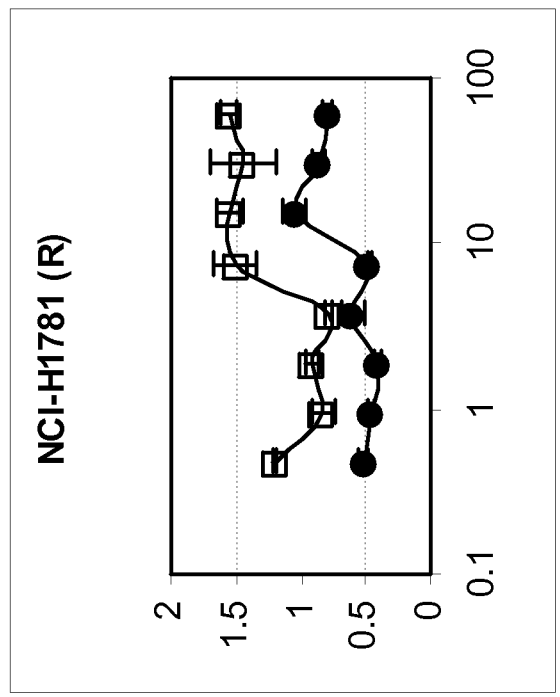
FIG. 8 shows synergy of NLRR-1 siRNA knockdown and erlotinib. Apoptosis in response to the EGFR inhibitor erlotinib was measured in tumor cell lines 8A: NCI-H647 8B: NCI-H1781 8C: NCI-H226, 8D: NCI-H520 8E: NCI-H2009 8F: SK-MES-1 (NLRR-1 negative) with a control siRNA (●)
Figure 8A:
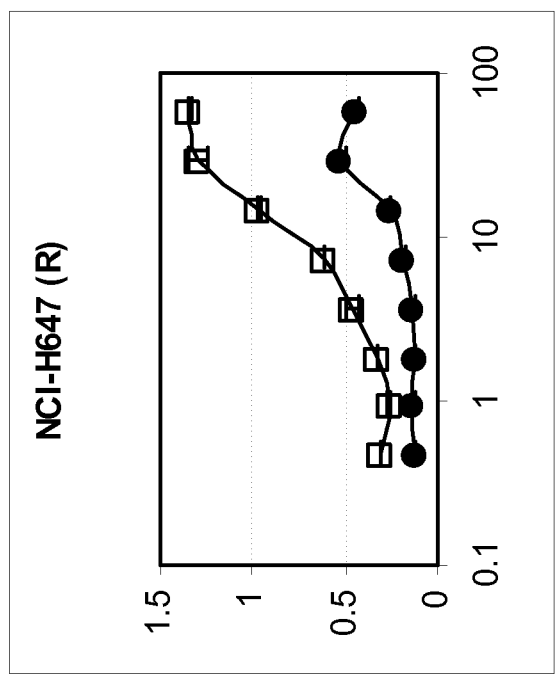
Figures 8C, 8D:
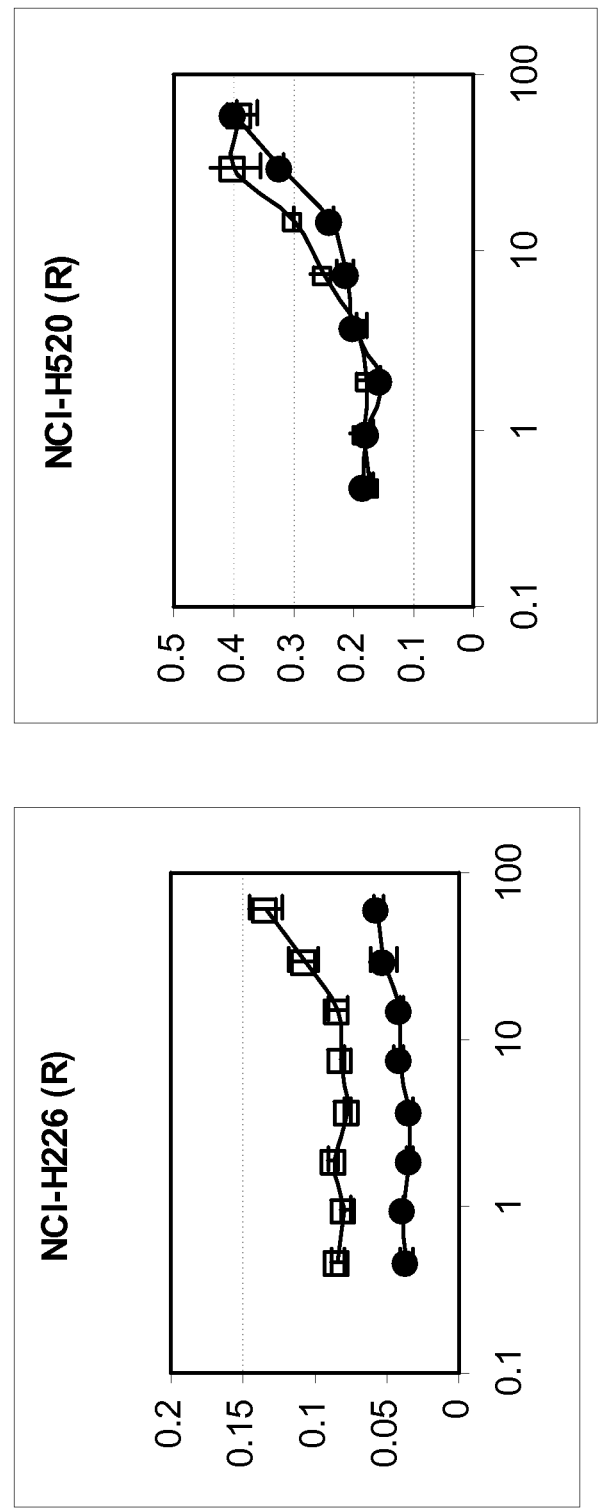

NLRR-1 was depleted using siRNA knockdown and cells were cultured in the presence of increasing concentrations of erlotinib. Several of these cell lines showed an increase in apoptosis as assessed by caspase 3/7 activity (FIG. 8). A significant increase in sensitivity was apparent for the otherwise erlotinib-resistant cell line NCI-H647 (Yauch et al., 2005) (FIG. 8A), and synergy between the NLRR-1 knockdown and erlotinib was observed for resistant cell lines NCI-H1781 (FIG. 8B), NCI-H226 (FIG. 8C), and possibly also, to a lesser degree in NCI-H520 (FIG. 8D). NCI-H2009, which is sensitive to erlotinib (Yauch et al., 2005), did not show any increased apoptosis in NLRR-1-depleted cells (FIG. 8E). As expected, the NLRR-1-negative control tumor cell line SK-MES (erlotinib-sensitive) did not show any increase in apoptosis upon knockdown of NLRR-1 (FIG. 8F). These data support our findings that NLRR-1 plays a significant role in EGFR signaling, and suggest that NLRR-1 could potentially contribute to the insensitivity encountered in some tumors to EGFR kinase inhibitors such as erlotinib.

REFERENCES

Andren, O., Fall, K., Andersson, S., Rubin, M. A., Karlsson, M., Bismar, T. A., Johansson, J., and Mucci, L. (2006a). Muc-1 gene is associated with prostate cancer progression: A 20-year follow-up of a population based study in Sweden. 2006 Prostate Cancer Symposium.

Andren, O., Fall, K., Franzen, L., Andersson, S. O., Johansson, J. E., and Rubin, M. A. (2006b). How well does the Gleason score predict prostate cancer death? A 20-year followup of a population based cohort in Sweden. The Journal of urology 175, 1337-1340.

Aubert, J., Stavridis, M. P., Tweedie, S., O'Reilly, M., Vierlinger, K., Li, M., Ghazal, P., Pratt, T., Mason, J. O., Roy, D., et al. (2003). Screening for mammalian neural genes via fluorescence-activated cell sorter purification of neural precursors from Sox1-gfp knock-in mice. Proc Natl Acad Sci USA 100 Suppl 1, 11836-11841.

Bormann, P., Roth, L. W., Andel, D., Ackermann, M., and Reinhard, E. (1999). zfNLRR, a novel leucine-rich repeat protein is preferentially expressed during regeneration in zebrafish. Mol Cell Neurosci 13, 167-179.

Chinnaiyan, P., Huang, S., Vallabhaneni, G., Armstrong, E., Varambally, S., Tomlins, S. A., Chinnaiyan, A. M., and Harari, P. M. (2005). Mechanisms of enhanced radiation response following epidermal growth factor receptor signaling inhibition by erlotinib (Tarceva). Cancer research 65, 3328-3335.

Dziadziuszko, R., Witta, S. E., Cappuzzo, F., Park, S., Tanaka, K., Danenberg, P. V., Baron, A. E., Crino, L., Franklin, W. A., Bunn, P. A., Jr., et al. (2006). Epidermal growth factor receptor messenger RNA expression, gene dosage, and gefitinib sensitivity in non-small cell lung cancer. Clin Cancer Res 12, 3078-3084.

Eberhard, D. A., Johnson, B. E., Amler, L. C., Goddard, A. D., Heldens, S. L., Herbst, R. S., Ince, W. L., Janne, P. A., Januario, T., Johnson, D. H., et al. (2005). Mutations in the epidermal growth factor receptor and in KRAS are predictive and prognostic indicators in patients with non-small-cell lung cancer treated with chemotherapy alone and in combination with erlotinib. J Clin Oncol 23, 5900-5909.

Ebner, R., and Derynck, R. (1991). Epidermal growth factor and transforming growth factor-alpha: differential intracellular routing and processing of ligand-receptor complexes. Cell regulation 2, 599-612.

El-Obeid, A., Hesselager, G., Westermark, B., and Nister, M. (2002). TGF-alpha-driven tumor growth is inhibited by an EGF receptor tyrosine kinase inhibitor. Biochem Biophys Res Commun 290, 349-358.

Fukamachi, K., Matsuoka, Y., Kitanaka, C., Kuchino, Y., and Tsuda, H. (2001). Rat neuronal leucine-rich repeat protein-3: cloning and regulation of the gene expression. Biochem Biophys Res Commun 287, 257-263.

Fukamachi, K., Matsuoka, Y., Ohno, H., Hamaguchi, T., and Tsuda, H. (2002). Neuronal leucine-rich repeat protein-3 amplifies MAPK activation by epidermal growth factor through a carboxyl-terminal region containing endocytosis motifs. J Biol Chem 277, 43549-43552.

Gleason, D. F., and Mellinger, G. T. (1974). Prediction of prognosis for prostatic adenocarcinoma by combined histological grading and clinical staging. The Journal of urology 111, 58-64.

Haines, B. P., Gupta, R., Michael Jones, C., Summerbell, D., and Rigby, P. W. (2005). The NLRR gene family and mouse development: Modified differential display PCR identifies NLRR-1 as a gene expressed in early somitic myoblasts. Dev Biol 281, 145-159.

Hamano, S., Ohira, M., Isogai, E., Nakada, K., and Nakagawara, A. (2004). Identification of novel human neuronal leucine-rich repeat (hNLRR) family genes and inverse association of expression of Nbla10449/hNLRR-1 and Nbla10677/hNLRR-3 with the prognosis of primary neuroblastomas. Int J Oncol 24, 1457-1466.

Han, S. W., Kim, T. Y., Hwang, P. G., Jeong, S., Kim, J., Choi, I. S., Oh, D. Y., Kim, J. H., Kim, D. W., Chung, D. H., et al. (2005). Predictive and prognostic impact of epidermal growth factor receptor mutation in non-small-cell lung cancer patients treated with gefitinib. J Clin Oncol 23, 2493-2501.

Haugh, J. M., Huang, A. C., Wiley, H. S., Wells, A., and Lauffenburger, D. A. (1999a). Internalized epidermal growth factor receptors participate in the activation of p21 (ras) in fibroblasts. J Biol Chem 274, 34350-34360.

Haugh, J. M., Schooler, K., Wells, A., Wiley, H. S., and Lauffenburger, D. A. (1999b). Effect of epidermal growth factor receptor internalization on regulation of the phospholipase C-gammal signaling pathway. J Biol Chem 274, 8958-8965.

Hayata, T., Uochi, T., and Asashima, M. (1998). Molecular cloning of XNLRR-1, a Xenopus homolog of mouse neuronal leucine-rich repeat protein expressed in the developing Xenopus nervous system. Gene 221, 159-166.

Hennessy, B. T., Smith, D. L., Ram, P. T., Lu, Y., and Mills, G. B. (2005). Exploiting the PI3K/AKT pathway for cancer drug discovery. Nature reviews 4, 988-1004.

Jhappan, C., Stahle, C., Harkins, R. N., Fausto, N., Smith, G. H., and Merlino, G. T. (1990). TGF alpha overexpression in transgenic mice induces liver neoplasia and abnormal development of the mammary gland and pancreas. Cell 61, 1137-1146.

Jiang, D., Yang, H., Willson, J. K., Liang, J., Humphrey, L. E., Zborowska, E., Wang, D., Foster, J., Fan, R., and Brattain, M. G. (1998). Autocrine transforming growth factor alpha provides a growth advantage to malignant cells by facilitating re-entry into the cell cycle from suboptimal growth states. J Biol Chem 273, 31471-31479.

Lapointe, J., Li, C., Higgins, J. P., van de Rijn, M., Bair, E., Montgomery, K., Ferrari, M., Egevad, L., Rayford, W., Bergerheim, U., et al. (2004). Gene expression profiling identifies clinically relevant subtypes of prostate cancer. Proc Natl Acad Sci USA 101, 811-816.

Levkowitz, G., Waterman, H., Zamir, E., Kam, Z., Oved, S., Langdon, W. Y., Beguinot, L., Geiger, B., and Yarden, Y. (1998). c-Cbl/Sli-1 regulates endocytic sorting and ubiquitination of the epidermal growth factor receptor. Genes & development 12, 3663-3674.

Lynch, T. J., Bell, D. W., Sordella, R., Gurubhagavatula, S., Okimoto, R. A., Brannigan, B. W., Harris, P. L., Haserlat, S. M., Supko, J. G., Haluska, F. G., et al. (2004). Activating mutations in the epidermal growth factor receptor underlying responsiveness of non-small-cell lung cancer to gefitinib. N Engl J Med 350, 2129-2139.

Maeda, K., Kato, Y., and Sugiyama, Y. (2002). pH-dependent receptor/ligand dissociation as a determining factor for intracellular sorting of ligands for epidermal growth factor receptors in rat hepatocytes. J Control Release 82, 71-82.

Martinez-Arca, S., Bech-Serra, J. J., Hurtado-Kuttner, M., Borroto, A., and Arribas, J. (2005). Recycling of cell surface pro-transforming growth factor-{alpha} regulates epidermal growth factor receptor activation. J Biol Chem 280, 36970-36977.

Moyer, J. D., Barbacci, E. G., Iwata, K. K., Arnold, L., Boman, B., Cunningham, A., DiOrio, C., Doty, J., Morin, M. J., Moyer, M. P., et al. (1997). Induction of apoptosis and cell cycle arrest by CP-358,774, an inhibitor of epidermal growth factor receptor tyrosine kinase. Cancer research 57, 4838-4848.

Ng, S. S., Tsao, M. S., Nicklee, T., and Hedley, D. W. (2002). Effects of the epidermal growth factor receptor inhibitor OSI-774, Tarceva, on downstream signaling pathways and apoptosis in human pancreatic adenocarcinoma. Molecular cancer therapeutics 1, 777-783.

O'Dwyer P, J., and Benson, A. B., 3rd (2002). Epidermal growth factor receptor-targeted therapy in colorectal cancer. Semin Oncol 29, 10-17.

Oliveira, S., van Bergen en Henegouwen, P. M., Storm, G., and Schiffelers, R. M. (2006). Molecular biology of epidermal growth factor receptor inhibition for cancer therapy. Expert opinion on biological therapy 6, 605-617.

Paez, J. G., Janne, P. A., Lee, J. C., Tracy, S., Greulich, H., Gabriel, S., Herman, P., Kaye, F. J., Lindeman, N., Boggon, T. J., et al. (2004). EGFR mutations in lung cancer: correlation with clinical response to gefitinib therapy. Science 304, 1497-1500.

Qian, X., Karpova, T., Sheppard, A. M., McNally, J., and Lowy, D. R. (2004). E-cadherin-mediated adhesion inhibits ligand-dependent activation of diverse receptor tyrosine kinases. The EMBO journal 23, 1739-1748.

Sato, Y., Takahashi, M., Shibukawa, Y., Jain, S. K., Hamaoka, R., Miyagawa, J., Yaginuma, Y., Honke, K., Ishikawa, M., and Taniguchi, N. (2001). Overexpression of N-acetylglucosaminyltransferase III enhances the epidermal growth factor-induced phosphorylation of ERK in HeLaS3 cells by up-regulation of the internalization rate of the receptors. J Biol Chem 276, 11956-11962.

Scher, H. I., Sarkis, A., Reuter, V., Cohen, D., Netto, G., Petrylak, D., Lianes, P., Fuks, Z., Mendelsohn, J., and Cordon-Cardo, C. (1995). Changing pattern of expression of the epidermal growth factor receptor and transforming growth factor alpha in the progression of prostatic neoplasms. Clin Cancer Res 1, 545-550.

Schoeberl, B., Eichler-Jonsson, C., Gilles, E. D., and Muller, G. (2002). Computational modeling of the dynamics of the MAP kinase cascade activated by surface and internalized EGF receptors. Nat Biotechnol 20, 370-375.

Sebastian, S., Settleman, J., Reshkin, S. J., Azzariti, A., Bellizzi, A., and Paradiso, A. (2006). The complexity of targeting EGFR signalling in cancer: from expression to turnover. Biochimica et biophysica acta 1766, 120-139.

Shepherd, F. A., Rodrigues Pereira, J., Ciuleanu, T., Tan, E. H., Hirsh, V., Thongprasert, S., Campos, D., Maoleekoonpiroj, S., Smylie, M., Martins, R., et al. (2005). Erlotinib in previously treated non-small-cell lung cancer. N Engl J Med 353, 123-132.

Sordella, R., Bell, D. W., Haber, D. A., and Settleman, J. (2004). Gefitinib-sensitizing EGFR mutations in lung cancer activate anti-apoptotic pathways. Science 305, 1163-1167.

Tackels-Horne, D., Goodman, M. D., Williams, A. J., Wilson, D. J., Eskandari, T., Vogt, L. M., Boland, J. F., Scherf, U., and Vockley, J. G. (2001). Identification of differentially expressed genes in hepatocellular carcinoma and metastatic liver tumors by oligonucleotide expression profiling. Cancer 92, 395-405.

Taguchi, A., Wanaka, A., Mori, T., Matsumoto, K., Imai, Y., Tagaki, T., and Tohyama, M. (1996). Molecular cloning of novel leucine-rich repeat proteins and their expression in the developing mouse nervous system. Brain Res Mol Brain Res 35, 31-40.

Taniguchi, H., Tohyama, M., and Takagi, T. (1996). Cloning and expression of a novel gene for a protein with leucine-rich repeats in the developing mouse nervous system. Brain Res Mol Brain Res 36, 45-52.

Tsao, M. S., Sakurada, A., Cutz, J. C., Zhu, C. Q., Kamel-Reid, S., Squire, J., Lorimer, I., Zhang, T., Liu, N., Daneshmand, M., et al. (2005). Erlotinib in lung cancer—molecular and clinical predictors of outcome. N Engl J Med 353, 133-144.

Vivanco, I., and Sawyers, C. L. (2002). The phosphatidylinositol 3-Kinase AKT pathway in human cancer. Nat Rev Cancer 2, 489-501.

Wang, D., Li, W., Jiang, W., Humphrey, L. E., Howell, G. M., and Brattain, M. G. (1998). Autocrine TGFalpha expression in the regulation of initiation of human colon carcinoma growth. J Cell Physiol 177, 387-395.

Wang, Y., Pennock, S., Chen, X., and Wang, Z. (2002). Endosomal signaling of epidermal growth factor receptor stimulates signal transduction pathways leading to cell survival. Mol Cell Biol 22, 7279-7290.

Wells, A. (1999). EGF receptor. The international journal of biochemistry & cell biology 31, 637-643.

Yauch, R. L., Januario, T., Eberhard, D. A., Cavet, G., Zhu, W., Fu, L., Pham, T. Q., Soriano, R., Stinson, J., Seshagiri, S., et al. (2005). Epithelial versus mesenchymal phenotype determines in vitro sensitivity and predicts clinical activity of erlotinib in lung cancer patients. Clin Cancer Res 11, 8686-8698.

Zhou, Y., and Brattain, M. G. (2005). Synergy of epidermal growth factor receptor kinase inhibitor AG1478 and ErbB2 kinase inhibitor AG879 in human colon carcinoma cells is associated with induction of apoptosis. Cancer research 65, 5848-5856.

We claim:

1. A method of inhibiting the growth of tumor cells in a subject, comprising administering to the subject a therapeutically effective amount of a Neuronal Leucine Rich Repeat Protein-1 (NLRR-1) antagonist and a therapeutically effect amount of small molecule EGFR antagonist, wherein the NLRR-1 antagonist is an anti-NLRR-1 antibody or an antigen binding fragment thereof, and wherein the tumor cells are resistant to the small molecule EGFR antagonist.

2. The method of claim 1, wherein the small molecule EGFR antagonist is erlotinib.

3. The method of claim 1, wherein the anti-NLRR-1 antibody is a monoclonal antibody.

4. The method of claim 3, wherein the monoclonal antibody is 3D1.6.9 produced from hybridoma cells having ATCC accession number PTA-8732.

5. The method of claim 1, wherein the anti-NLRR-1 antibody competes for binding with the monoclonal antibody 3D1.6.9 produced from hybridoma cells having ATCC accession number PTA-8732.

6. The method of claim 1, wherein the anti-NLRR-1 antibody is a chimeric, human, or humanized antibody.

7. The method of claim 6, wherein the chimeric or humanized antibody comprises all six CDRs of the monoclonal antibody 3D1.6.9 produced from hybridoma cells having ATCC accession number PTA-8732.

8. The method of claim 1, wherein Epidermal Growth Factor Receptor (EGFR) is not amplified in the tumor cells.

9. A method for treating cancer in a subject comprising administering to the subject an effective amount of a Neuronal Leucine Rich Repeat Protein-1 (NLRR-1) antagonist and a therapeutically effect amount of small molecule EGFR antagonist, wherein the NLRR-1 antagonist is an anti-NLRR-1 antibody or an antigen binding fragment thereof, and wherein the cancer is resistant to the small molecule EGFR antagonist.

10. The method of claim 9, wherein the small molecule EGFR antagonist is erlotinib.

11. The method of claim 9, wherein the anti-NLRR-1 antibody is a monoclonal antibody.

12. The method of claim 11, wherein the monoclonal antibody is 3D1.6.9 produced from hybridoma cells having ATCC accession number PTA-8732.

13. The method of claim 9, wherein the anti-NLRR-1 antibody competes for binding with the monoclonal antibody 3D1.6.9 produced from hybridoma cells having ATCC accession number PTA-8732.

14. The method of claim 9, wherein the anti-NLRR-1 antibody is a chimeric, human, or humanized antibody.

15. The method of claim 14, wherein the chimeric or humanized antibody comprises all six CDRs of the monoclonal antibody 3D1.6.9 produced from hybridoma cells having ATCC accession number PTA-8732.

16. The method of claim 9, wherein Epidermal Growth Factor Receptor (EGFR) is not amplified in the tumor cells.

* * * * *

SEQUENCE LISTING

<160> NUMBER OF SEQ ID NOS: 12

<210> SEQ ID NO 1
<211> LENGTH: 712
<212> TYPE: PRT
<213> ORGANISM: Homo sapiens

<400> SEQUENCE: 1

Met Ala Arg Met Ser Phe Val Ile Ala Ala Cys Gln Leu Val Leu Gly
1               5                   10                  15

Leu Leu Met Thr Ser Leu Thr Glu Ser Ser Ile Gln Asn Ser Glu Cys
            20                  25                  30

Pro Gln Leu Cys Val Cys Glu Ile Arg Pro Trp Phe Thr Pro Gln Ser
        35                  40                  45

Thr Tyr Arg Glu Ala Thr Thr Val Asp Cys Asn Asp Leu Arg Leu Thr
    50                  55                  60

Arg Ile Pro Ser Asn Leu Ser Ser Asp Thr Gln Val Leu Leu Leu Gln
65                  70                  75                  80

Ser Asn Asn Ile Ala Lys Thr Val Asp Glu Leu Gln Gln Leu Phe Asn
                85                  90                  95

Leu Thr Glu Leu Asp Phe Ser Gln Asn Asn Phe Thr Asn Ile Lys Glu
            100                 105                 110

Val Gly Leu Ala Asn Leu Thr Gln Leu Thr Thr Leu His Leu Glu Glu
        115                 120                 125

Asn Gln Ile Thr Glu Met Thr Asp Tyr Cys Leu Gln Asp Leu Ser Asn
    130                 135                 140

Leu Gln Glu Leu Tyr Ile Asn His Asn Gln Ile Ser Thr Ile Ser Ala
145                 150                 155                 160

His Ala Phe Ala Gly Leu Lys Asn Leu Leu Arg Leu His Leu Asn Ser
                165                 170                 175

Asn Lys Leu Lys Val Ile Asp Ser Arg Trp Phe Asp Ser Thr Pro Asn
            180                 185                 190

Leu Glu Ile Leu Met Ile Gly Glu Asn Pro Val Ile Gly Ile Leu Asp
        195                 200                 205

Met Asn Phe Lys Pro Leu Ala Asn Leu Arg Ser Leu Val Leu Ala Gly
    210                 215                 220

Met Tyr Leu Thr Asp Ile Pro Gly Asn Ala Leu Val Gly Leu Asp Ser
225                 230                 235                 240

Leu Glu Ser Leu Ser Phe Tyr Asp Asn Lys Leu Val Lys Val Pro Gln
                245                 250                 255

Leu Ala Gln Lys Val Pro Asn Leu Lys Phe Leu Asp Leu Asn Lys Asn
            260                 265                 270

Pro Ile His Lys Ile Gln Glu Gly Asp Phe Lys Asn Met Leu Arg Leu
        275                 280                 285

Lys Glu Leu Gly Ile Asn Asn Met Gly Glu Leu Val Ser Val Asp Arg
    290                 295                 300

Tyr Ala Leu Asp Asn Leu Pro Glu Leu Thr Lys Leu Glu Ala Thr Asn
305                 310                 315                 320

Asn Pro Lys Leu Ser Tyr Ile His Arg Leu Ala Phe Arg Ser Val Pro
                325                 330                 335

Ala Leu Glu Ser Leu Met Leu Asn Asn Asn Ala Leu Asn Ala Ile Tyr
            340                 345                 350

Gln Lys Thr Val Glu Ser Leu Pro Asn Leu Arg Glu Ile Ser Ile His
        355                 360                 365

Ser Asn Pro Leu Arg Cys Asp Cys Val Ile His Trp Ile Asn Ser Asn
370                 375                 380

Lys Thr Asn Ile Arg Phe Met Glu Pro Leu Ser Met Phe Cys Ala Met
385                 390                 395                 400

Pro Pro Glu Tyr Lys Gly His Gln Val Lys Glu Val Leu Gln Asp Ser
                405                 410                 415

Ser Glu Gln Cys Leu Pro Met Ile Ser His Asp Ser Phe Pro Asn Arg
                420                 425                 430

Leu Asn Val Asp Ile Gly Thr Thr Val Phe Leu Asp Cys Arg Ala Met
            435                 440                 445

Ala Glu Pro Glu Pro Glu Ile Tyr Trp Val Thr Pro Ile Gly Asn Lys
450                 455                 460

Ile Thr Val Glu Thr Leu Ser Asp Lys Tyr Lys Leu Ser Ser Glu Gly
465                 470                 475                 480

Thr Leu Glu Ile Ser Asn Ile Gln Ile Glu Asp Ser Gly Arg Tyr Thr
                485                 490                 495

Cys Val Ala Gln Asn Val Gln Gly Ala Asp Thr Arg Val Ala Thr Ile
                500                 505                 510

Lys Val Asn Gly Thr Leu Leu Asp Gly Thr Gln Val Leu Lys Ile Tyr
            515                 520                 525

Val Lys Gln Thr Glu Ser His Ser Ile Leu Val Ser Trp Lys Val Asn
530                 535                 540

Ser Asn Val Met Thr Ser Asn Leu Lys Ser Ser Ala Thr Met Lys Ile
545                 550                 555                 560

Asp Asn Pro His Ile Thr Tyr Thr Ala Arg Val Pro Val Asp Val His
                565                 570                 575

Glu Tyr Asn Leu Thr His Leu Gln Pro Ser Thr Asp Tyr Glu Val Cys
                580                 585                 590

Leu Thr Val Ser Asn Ile His Gln Thr Gln Lys Ser Cys Val Asn Val
            595                 600                 605

Thr Thr Lys Asn Ala Ala Phe Ala Val Asp Ile Ser Asp Gln Glu Thr
610                 615                 620

Ser Thr Ala Leu Ala Ala Val Met Gly Ser Met Phe Ala Val Ile Ser
625                 630                 635                 640

Leu Ala Ser Ile Ala Val Tyr Phe Ala Lys Arg Phe Lys Arg Lys Asn
                645                 650                 655

Tyr His His Ser Leu Lys Lys Tyr Met Gln Lys Thr Ser Ser Ile Pro
                660                 665                 670

Leu Asn Glu Leu Tyr Pro Pro Leu Ile Asn Leu Trp Glu Gly Asp Ser
            675                 680                 685

Glu Lys Asp Lys Asp Gly Ser Ala Asp Thr Lys Pro Thr Gln Val Asp
690                 695                 700

Thr Ser Arg Ser Tyr Tyr Met Trp
705                 710

<210> SEQ ID NO 2
<211> LENGTH: 23
<212> TYPE: DNA
<213> ORGANISM: ARTIFICIAL SEQUENCE
<220> FEATURE:
<223> OTHER INFORMATION: PRIMER

<400> SEQUENCE: 2
tcaatcccac taaatgagct gta                                           23

```
<210> SEQ ID NO 3
<211> LENGTH: 22
<212> TYPE: DNA
<213> ORGANISM: ARTIFICIAL SEQUENCE
<220> FEATURE:
<223> OTHER INFORMATION: PRIMER

<400> SEQUENCE: 3
gtctgcagaa ccatctttgt ct                                              22

<210> SEQ ID NO 4
<211> LENGTH: 26
<212> TYPE: DNA
<213> ORGANISM: ARTIFICIAL SEQUENCE
<220> FEATURE:
<223> OTHER INFORMATION: PROBE

<400> SEQUENCE: 4
ccaccactca ttaacctctg ggaagg                                          26

<210> SEQ ID NO 5
<211> LENGTH: 18
<212> TYPE: DNA
<213> ORGANISM: ARTIFICIAL SEQUENCE
<220> FEATURE:
<223> OTHER INFORMATION: PRIMER

<400> SEQUENCE: 5
tggcagcagc ctctctta                                                   18

<210> SEQ ID NO 6
<211> LENGTH: 19
<212> TYPE: DNA
<213> ORGANISM: ARTIFICIAL SEQUENCE
<220> FEATURE:
<223> OTHER INFORMATION: PRIMER

<400> SEQUENCE: 6
cccctacaag ttggcagaa                                                  19

<210> SEQ ID NO 7
<211> LENGTH: 21
<212> TYPE: DNA
<213> ORGANISM: ARTIFICIAL SEQUENCE
<220> FEATURE:
<223> OTHER INFORMATION: PROBE

<400> SEQUENCE: 7
cacaaaccca gcagtggcag c                                               21

<210> SEQ ID NO 8
<211> LENGTH: 20
<212> TYPE: DNA
<213> ORGANISM: ARTIFICIAL SEQUENCE
<220> FEATURE:
<223> OTHER INFORMATION: PRIMER

<400> SEQUENCE: 8
gcggattctc atggaacaca                                                 20

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: PRIMER
```

```
<400> SEQUENCE: 9
ggtcagccag gagcttcttg                                           20

<210> SEQ ID NO 10
<211> LENGTH: 25
<212> TYPE: DNA
<213> ORGANISM: ARTIFICIAL SEQUENCE
<220> FEATURE:
<223> OTHER INFORMATION: PROBE

<400> SEQUENCE: 10
cacaagctga aggcagacaa ggccc                                     25

<210> SEQ ID NO 11
<211> LENGTH: 21
<212> TYPE: RNA
<213> ORGANISM: ARTIFICIAL SEQUENCE
<220> FEATURE:
<223> OTHER INFORMATION: siRNA

<400> SEQUENCE: 11
gccagaaccu gaaauuuacu u                                         21

<210> SEQ ID NO 12
<211> LENGTH: 21
<212> TYPE: RNA
<213> ORGANISM: ARTIFICIAL SEQUENCE
<220> FEATURE:
<223> OTHER INFORMATION: siRNA

<400> SEQUENCE: 12
guaaauuuca gguucuggcu u                                         21
```